United States Patent
Amiji et al.

(10) Patent No.: US 12,121,608 B2
(45) Date of Patent: Oct. 22, 2024

(54) BIODEGRADABLE IMPLANT FOR SUSTAINED TRANS-NASAL DELIVERY OF THERAPEUTIC AGENTS TO THE BRAIN

(71) Applicants: Northeastern University, Boston, MA (US); Massachusetts Eye and Ear Infirmary, Boston, MA (US)

(72) Inventors: Mansoor M. Amiji, Attleboro, MA (US); Smrithi Padmakumar, Brighton, MA (US); Benjamin S. Bleier, Boston, MA (US)

(73) Assignees: Northeastern University, Boston, MA (US); Massachusetts Eye and Ear Infirmary, Boston, MA (US)

( * ) Notice: Subject to any disclaimer, the term of this patent is extended or adjusted under 35 U.S.C. 154(b) by 225 days.

(21) Appl. No.: 17/338,505

(22) Filed: Jun. 3, 2021

(65) Prior Publication Data

US 2021/0378947 A1 Dec. 9, 2021

Related U.S. Application Data

(60) Provisional application No. 63/034,096, filed on Jun. 3, 2020.

(51) Int. Cl.
*A61K 9/00* (2006.01)
*A61K 47/34* (2017.01)

(52) U.S. Cl.
CPC .......... *A61K 9/0004* (2013.01); *A61K 9/0043* (2013.01); *A61K 47/34* (2013.01)

(58) Field of Classification Search
CPC ..... A61K 9/0004; A61K 47/34; A61K 9/0043
See application file for complete search history.

(56) References Cited

U.S. PATENT DOCUMENTS

| | | | |
|---|---|---|---|
| 2002/0068080 A1 | 6/2002 | Lerner | |
| 2004/0219214 A1* | 11/2004 | Gravett | A61P 9/14 424/484 |
| 2005/0142162 A1* | 6/2005 | Hunter | A61L 31/16 424/423 |
| 2008/0319424 A1 | 12/2008 | Muni et al. | |
| 2014/0099709 A1* | 4/2014 | Presnell | A61L 27/3886 435/325 |

FOREIGN PATENT DOCUMENTS

| | | | |
|---|---|---|---|
| WO | 2005089659 A1 | 9/2005 | |
| WO | WO-2007111636 A2 * | 10/2007 | A61B 17/24 |
| WO | 2008045242 A2 | 4/2008 | |

(Continued)

OTHER PUBLICATIONS

Illum Lisbeth et al., (KR 20110056516 A), Eng. Trans (Year: 2011).*

(Continued)

*Primary Examiner* — Blessing M Fubara
(74) *Attorney, Agent, or Firm* — Verrill Dana, LLP

(57) ABSTRACT

A method of delivering a therapeutic agent into the central nervous system through the blood-brain barrier includes implanting an implant within the submucosal space of the olfactory epithelium. The implant can provide sustained drug delivery to the brain. The implant can be placed using a minimally invasive surgical approach.

17 Claims, 38 Drawing Sheets

Specification includes a Sequence Listing.

(56) References Cited

FOREIGN PATENT DOCUMENTS

WO    2019157259 A1    8/2019

OTHER PUBLICATIONS

National Institute on Aging, Basics of Alzheimer's Disease and Dementia, 1018 (Year: 2018).*

Güney et al., "Thermoplastic PCL-b-PEG-b-PCL and HDI Polyurethanes for Extrusion-Based 3D-Printing of Tough Hydrogels", Bioengineering (Basel). Nov. 14, 2018;5(4):99. doi: 10.3390/bioengineering5040099. PMID: 30441879; PMCID: PMC6316089 14 pages.

Shaukat et al., "Evaluation of Different Polymers in 3D Printing Technologies", BASF Corporation (2019), 12 pages.

Padmakumar et al., "Osmotic core-shell polymeric implant for sustained BDNF AntagoNAT delivery in CNS using minimally invasive nasal depot (MIND) approach", Biomaterials, 2021, 34 pages.

Padmakumar et al., "Minimally Invasive Nasal Depot (MIND) technique for direct BDNF AntagnoNAT delivery to the brain", Journal of Controlled Release 331, (2021), pp. 176-186.

Cohen-Pfeffer et al., "Intracerebroventricular Delivery as a Safe, Long-Term Route of Drug Administration", Pediatr Neurol., 67, 23-35-(2017).

Slavc et al., "Best practices for the use of intracerebroventricular drug delivery devices", Molecular Genetics and Metabolism, 124, 184-188 (2018).

Hanson et al., "Intranasal delivery bypasses the blood-brain barrier to target therapeutic agents to the central nervous system and treat neurodegenerative disease", BMC Neuroscience, 9, S5 (2008), pp. 1-4.

Tan et al., "Injectable, Biodegradable Hydrogels for Tissue Engineering Applications", Materials, 3, (2010), 1746-1767.

Gioffredi et al., "Pluronic F127 hydrogel characterization and biofabrication in cellularized constructs for tissue engineering applications.", Procedia CIRP 49, 125-132 (2016).

Manoukian et al., "Biodegradable Polymeric Injectable Implants for Long-Term Delivery of Contraceptive Drugs", J. Appl. Polym. Sci. Apr. 2018; 135(14): pp. 1-23.

Amjad et al., "Current Practices for Outpatient Initiation of Levodopa-Carbidopa Intestinal Gel for Management of Advanced Parkinson's Disease in the United States", Adv. Ther. (2019) 36:2233-2246.

Gänger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, 10, 116. pp. 1-28.

Shantha, "CNS Delivery—Bypassing the BBB: Drug Delivery From the Olfactory Mucosa to the CNS", Drug Development & Delivery, 17, 32-37 (2017).

Lv et al., "Enhanced permeation performance of cellulose acetate ultrafiltration membrane by incorporation of Pluronic F127.", J. Membr. Sci. 7 (2007), pp. 68-74.

Falath et al., "Highly improved reverse osmosis performance of novel PVA/DGEBA cross-linked membranes by incorporation of Pluronic F-127 and MWCNTs for water desalination", Desalination 397 (2016) pp. 53-66.

Gilbert et al., "Drug release from Pluronic F-127 gels", Int. J. Pharm. 32, pp. 223-228 (1986).

Guzmán et al., "Polyoxyethylene-polyoxypropylene block copolymer gels as sustained release vehicles for subcutaneous drug administration", Int. J. Pharm. 80, 119-127 (1992).

Castren et al., "Brain-derived neurotrophic factor messenger RNA is expressed in the septum, hypothalamus and in adrenergic brain stem nuclei of adult rat brain and is increased by osmotic stimulation in the paraventricular nucleus", Neuroscience vol. 64, No. 1, pp. 71-80 (1995).

* cited by examiner

Capsule-like implants

Tablet-like implants

Sample_1 3.0kV 8.4mm x100 SE(M) 8/12/2020  500um

LOW MAGNIFICATION

Sample_1 3.0kV 8.1mm x25.0 SE(M) 8/12/2020  2.00um

HIGH MAGNIFICATION

Rat submucosal space after nasal bone removal

Bilateral flaps elevated to expose nasal bone

Skin closure by continuous suturing

Implant placed in the cavity

BIODEGRADABLE IMPLANT FOR SUSTAINED TRANS-NASAL DELIVERY OF THERAPEUTIC AGENTS TO THE BRAIN

CROSS-REFERENCE TO RELATED APPLICATIONS

This application claims priority to U.S. Provisional Application No. 63/034,096, filed 3 Jun. 2020, which is incorporated by reference herein in its entirety.

STATEMENT REGARDING FEDERALLY SPONSORED RESEARCH OR DEVELOPMENT

This invention was made with government support under Grant Number R01NS108968 awarded by the National Institutes of Health. The government has certain rights in the invention.

BACKGROUND

Central nervous system (CNS) diseases refer to those groups of neurological disorders particularly affecting the CNS, including the brain and spinal cord. They can arise due to multiple factors such as neurodegeneration, infections leading to potential damage, trauma, metabolic disorders, tumor, and stroke. Common symptoms of CNS diseases are associated with the loss of intact coordination between the nervous system circuits, which results in disruptions of motor activities, such as tremors and ataxias, and non-motor activities, such as dementia, cognitive decline, and behavioral disturbances. The progressive loss or depletion of neurons producing certain neurotransmitters and belonging to particular brain regions leads to diseases such as Parkinson's disease and Alzheimer's disease. Alzheimer's disease and Parkinson's disease affect nearly 5 million and 1 million of the current American population respectively, and their incidences increase with the aging population. These diseases have been considered as incurable, and the existing therapeutic strategies are targeted to relieve the symptoms. Many reports indicate that the common neurological diseases pose a staggering financial burden annually to the American healthcare system, totaling up to $800 billion per year. These situations underscore the need for developing more approaches to prevent and effectively treat CNS disorders.

Delivering therapeutics across the blood-brain barrier (BBB) to the CNS, particularly biotherapeutics having a high molecular size, is one of the biggest challenges in treating CNS disorders today. Therapeutic agents often include charge, including multiple charges per molecule, or a degree of polarity that hinders passage through the BBB. Methods and delivery devices are needed to enhance delivery of therapeutic agents across the BBB.

SUMMARY

A long-acting drug delivery implant is provided by the present technology. The implant can deliver a large variety of therapeutic agents through bypassing the blood-brain barrier to the brain or other parts of the CNS using the trans-nasal approach. The implant can be placed into nasal mucosa using a minimally invasive, trans-nasal surgical approach.

An aspect of the present technology is an implant for trans-nasal delivery of one or more therapeutic agents. The implant includes a support body that is formed from a first biodegradable polymer and contains a reservoir. The reservoir contains a polymer matrix formed from a second biodegradable polymer and a therapeutic agent which is embedded in the polymer matrix. Preferably the polymer matrix is a gel, such as an osmotic hydrogel that swells upon contact with a physiological fluid, such as extracellular fluid present in the nasal mucosa where the implant is placed. Osmotic swelling promotes the release of the therapeutic agent from the implant. The implant is biocompatible and biodegradable.

Another aspect of the present technology is a method of sustained delivery of a therapeutic agent to the central nervous system (CNS) of a subject in need thereof, such as a human, mammalian, or other animal subject. The method includes the steps of: (a) providing the implant described above; and (b) placing the implant into a submucosal space of an olfactory epithelium of the subject. Step (b) preferably is carried out using a minimally invasive surgical procedure such as the minimally invasive nasal depot (MIND) surgical approach which is described in WO2019157259A1. After placement in the subject, the therapeutic agent is released from the implant and enters the CNS of the subject over a sustained period of time.

Yet another aspect of the technology is a kit for delivering a therapeutic agent to the CNS of a subject. The kit contains the implant described above as well as instructions for implanting the implant into a submucosal space of an olfactory epithelium of the subject. The kit can optionally include one or more solutions, reagents, or devices, such as surgical devices, which may be adapted for use with the particular implant of the kit, for use during placement of the implant.

The technology can be further summarized in the following list of features.

1. An implant for trans-nasal delivery of one or more therapeutic agents, the implant comprising:
   a support body comprising a first biodegradable polymer, the support body containing a reservoir; and
   a polymer matrix comprising a second biodegradable polymer and a therapeutic agent, the polymer matrix disposed in the reservoir.
2. The implant of feature 1, wherein the first biodegradable polymer is a natural or synthetic polymer selected from the group consisting of gelatin, chitosan, cellulose or cellulose derivatives, poly(ε-caprolactone) (PCL), polyethylene glycol (PEG), poly(lactic-co-glycolic acid) (PLGA), polylactic acid (PLA), polyglycolide, PEG-PLA diblock copolymer, PEG-PLGA diblock copolymer, PEG-PCL diblock copolymer, PCL-b-PEG-b-PCL co-polymer, and combinations thereof.
3. The implant of feature 1 or 2, wherein the second biodegradable polymer is selected from the group consisting of polypropylene glycol (PPG), polyethylene glycol (PEG), polyacrylic acid, polyacrylamide, poly(N-isopropylacrylamide), polyethylene oxide-polypropylene oxide-polyethylene oxide (PEO-PPO-PEO) triblock copolymer, hyaluronic acid, polyethylene oxide, polypropylene oxide, alginic acid, chitosan, and combinations thereof.
4. The implant of any of the preceding features, wherein the polymer matrix is a gel.
5. The implant of feature 4, wherein the gel functions as an osmotic hydrogel.
6. The implant of any of the preceding features, wherein the support body comprises one or more openings or pores through which the polymer matrix is exposed to a fluid outside the implant when the implant is placed in a subject.

7. The implant of feature 6, wherein the support body comprises pores and the pores have an average diameter in the range from about 0.1 μm to about 100 μm.

8. The implant of any of the preceding features, wherein the implant has a core-shell structure, wherein the core comprises or consists of the polymer matrix and the shell surrounding or partially surrounding the core comprises or consists of the first biodegradable polymer.

9. The implant of any of the preceding features, wherein the first biodegradable polymer is hydrophobic.

10. The implant of any of the preceding features, wherein the second biodegradable polymer is hydrophilic.

11. The implant of any of the preceding features, wherein the second biodegradable polymer is PEG having an average molecular weight (Mn) in the range from about 750 Da to about 14000 Da.

12. The implant of any of the preceding features, wherein the therapeutic agent is a small molecule drug, a growth factor, a natural antisense transcript inhibitor, mRNA, a nutrient, a memory enhancing agent, a stimulant, an oligopeptide, a protein, an oligonucleotide, a tumor-targeting ligand, an antibody, an aptamer, a cell adhesion molecule, or a combination thereof.

13. The implant of any of the preceding features that is configured for implantation in a human subject within an olfactory sub-epithelium of the subject or within a submucosal space of an olfactory epithelium of the subject.

14. The implant of any of the preceding features that is capable of releasing the therapeutic agent into a central nervous system of a human subject.

15. The implant of any of the preceding features, wherein the biodegradable polymer biodegrades after an implantation into a nasal cavity of a subject for a duration in the range from about 1 day to about 365 days.

16. A method of sustained delivery of a therapeutic agent to a central nervous system (CNS) of a subject in need thereof, the method comprising:
  (a) providing the implant of any of the preceding features; and
  (b) placing the implant into a submucosal space of an olfactory epithelium of the subject;
  whereby the therapeutic agent is released from the implant and enters the CNS of the subject over a period of time.

17. The method of feature 16, wherein the therapeutic agent released by the implant bypasses a blood brain barrier of the subject.

18. The method of feature 16 or 17, wherein the period of time is greater than about 30 minutes, or greater than about 1 hour, or greater than about 1 day, or greater than about 7 days, or greater than about 30 days, or greater than about 1 year.

19. The method of any of features 16-18, wherein the release comprises diffusion of the therapeutic agent out of said polymer matrix and into the submucosal space.

20. The method of any of features 16-19, wherein the therapeutic agent is at least partially soluble in cerebrospinal fluid of the subject.

21. The method of any of features 16-20, wherein the therapeutic agent enters the CNS by diffusion through olfactory epithelium of the subject.

22. The method of any of features 16-21, wherein the therapeutic agent diffuses to a brain region selected from the group consisting of olfactory bulb, striatum, hippocampus, substantia nigra, cerebellum, and combinations thereof.

23. The method of any of features 16-22, wherein the polymer matrix comprises an osmotic hydrogel and the osmotic hydrogel swells when the implant is implanted in the subject.

24. The method of any of features 16-23, wherein step (b) comprises performing a surgical procedure on the subject.

25. The method of feature 24, wherein the surgical method does not comprise entering the CNS of the subject by crossing dura mater.

26. The method of any of features 16-23, wherein the implant is implanted into the nasal mucosa of the subject by a method comprising use of a catheter, an endoscope, a minimally invasive nasal depot surgical procedure, or a combination thereof.

27. The method of any of features 16-26, wherein the method aids in treatment or prevention of a disease or disorder of the CNS of the subject.

28. The method of feature 27, wherein the central nervous system disease or disorder is selected from the group consisting of neurodegeneration, an aging associated disease, an infection, nerve damage, trauma, tremors, ataxia, dementia, cognitive decline, a behavioral disturbance, a metabolic disorder, a tumor, a stroke, Parkinson's disease, and Alzheimer's disease.

29. The method of any of features 16-28, wherein the therapeutic agent does not contact a peripheral circulatory system of the subject.

30. The method of feature 29, wherein a systemic side effect caused by the therapeutic agent is reduced compared with delivery of the therapeutic agent by a method that allows contacting the therapeutic agent with the peripheral circulatory system of the subject.

31. The method of any of features 16-30, wherein the implant does not elicit an immune response in the subject.

32. A method of manufacturing the implant of any of features 1-15, the method comprising forming a biodegradable polymer in a shape of the support body.

33. The method of feature 32, further comprising filling the reservoir of the implant with the polymer matrix comprising the therapeutic agent or a composition that forms the polymer matrix comprising the therapeutic agent, and optionally sealing the reservoir with a biodegradable polymer material.

34. The method of feature 32 or feature 33, further comprising mixing the therapeutic agent with a biodegradable polymer to form the polymer matrix or a composition used to form the polymer matrix.

35. The method of any of features 32-34, wherein the method comprises one or more of molding, dip coating, extrusion, 2D printing or 3D printing.

36 The method of feature 35, wherein the method comprises 3D printing and the biodegradable polymer comprises a poly(ε-caprolactone)-b-poly(ethylene glycol)-b-poly(ε-caprolactone) co-polymer.

37. A kit for delivering a therapeutic agent to the CNS of a subject, the kit comprising the implant of any of features 1-15, instructions for implanting the implant into a region of an olfactory epithelium of a subject, and optionally one or more solutions, reagents, or devices for use during implantation of the implant.

As used herein, the term "about" refers to a range of within plus or minus 10%, 5%, 1%, or 0.5% of the stated value.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expression "consisting of" or "consisting essentially of".

BRIEF DESCRIPTION OF THE DRAWINGS

FIG. 15A shows exposure of nasal bones after the elevation of bilateral skin flaps post-midline sagittal incision. FIG. 15B shows high speed drill-aided removal of nasal bone for formation of a subcutaneous cavity within the submucosal space. FIG. 15C shows placing of BDNF AT core-shell implant within the cavity. FIG. 15D shows closure of skin incision with nylon sutures.

FIG. 16A provides an illustration showing the location site of implant with various sub-regions of interest in rat brain. FIGS. 16B-16F show BDNF AT levels in tissues of these sub-regions at different time points such as 4, 7, 14, 21 and 28 days, quantified by BDNF AT hybridisation assay (n=4 rats/time point, AT levels represented as mean±SEM).

In FIG. 24C, the position of this depot is directly anatomically analogous to the submucosal space occupied by the depot in the human nose depicted in FIG. 24A.

DETAILED DESCRIPTION

Figure 1A:
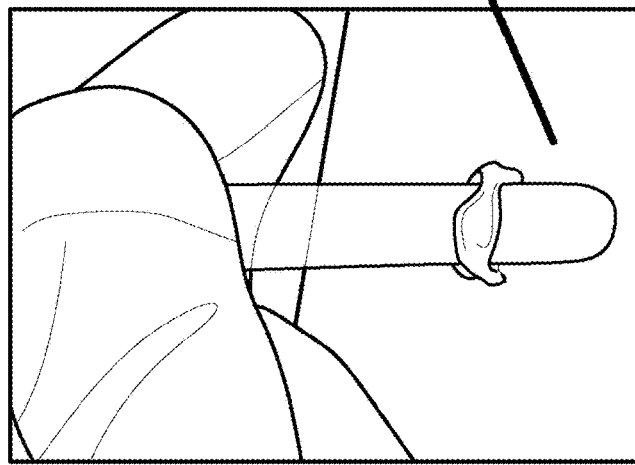
FIG. 1A shows an image of an implant biodegradable polymer shell formed by dip-coating of a glass rod into the polymer.
Figure 1B:
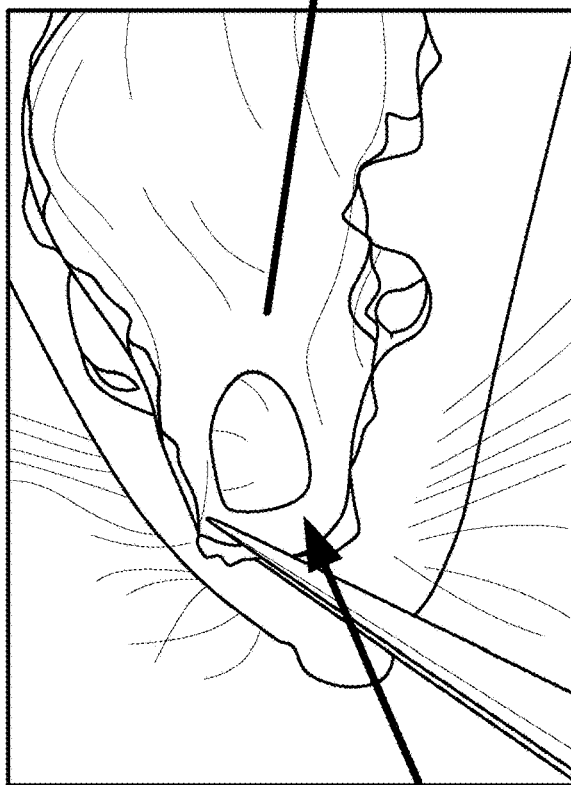
FIG. 1B shows an image of an implant during extraction from a Sprague Dawley rat after euthanasia.
Figure 1C:
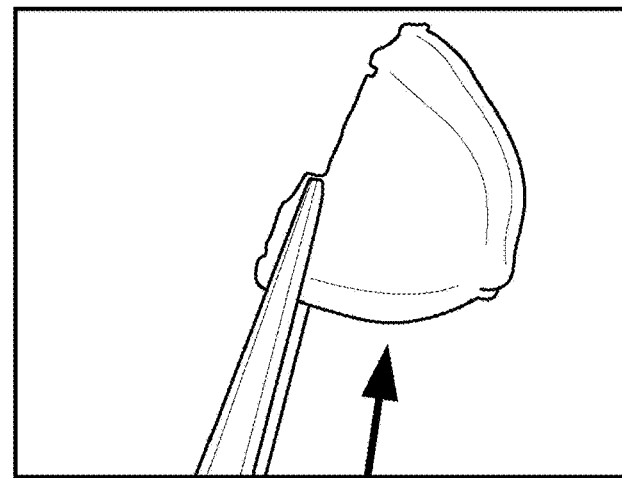
FIG. 1C shows an image of an implant retrieved after extraction from a Sprague Dawley rat.

The present technology provides intranasal implants for trans-nasal delivery of therapeutic agents across the blood brain barrier (BBB). Previous methods of drug delivery across the BBB, such as highly invasive intrathecal (IT) or intracerebroventricular (ICV) routes that physically breach the BBB, involve high risks and potentially serious complications. The present trans-nasal drug delivery strategies exploit the diffusion of therapeutics through the olfactory mucosa, which is safer and less invasive in comparison to the invasive procedures currently employed in clinics. The implants of the present technology include biodegradable polymers for enabling the controlled and sustained trans-mucosal delivery of therapeutics including small molecule drugs (e.g., chemical compounds having a molecular weight of 1500 Daltons or less), peptides, proteins, nucleic acid molecules such as oligonucleotides, and growth factors for treatment of CNS disorders. Deliverable therapeutic molecules can include biomolecules such as nucleic acids (e.g., mRNA, siRNA, antisense oligonucleotides, etc), peptides, and proteins including antibodies. Therapeutic agents can be delivered into the brain continuously through this approach. The implants are biodegradable and biocompatible, and can be used for eluting such therapeutic agents for prolonged durations. The implants can be fabricated in desired dimensions by microfabrication techniques, and they can be surgically implanted within the nasal mucosal cavity with a minimally invasive, simple surgical procedure, such as the procedure referred to herein as the minimally invasive nasal depot (MIND) surgical approach which is described in WO2019157259A1 (hereby incorporated by reference).

The size and shape of the implants can be configured as needed depending on the type of drug(s), therapeutic indication, duration, etc. In some examples, the implants can have cylindrical or semi-cylindrical shapes having an internal space that is in a range from about 1 mm to about 10 mm internal diameter. In another example, the implants can be provided as a plurality or set of implants for simultaneous or sequential implantation. Each implant can be tailored for a specific duration of release and biodegradation based on the dimensions and molecular weight, crosslinking, or type of biodegradable polymer used. This versatility can be useful for the development of delivery systems for a broad spectrum of payloads in the treatment of CNS diseases. Implants can be fabricated using the processes known to a person of ordinary skill in the art including microfabrication, 3D printing, injection molding and others.

As an example, the present technology can deliver Brain-Derived Neurotrophic Factor (BDNF) (14 kDa) across the BBB. The strategy can employ delivery of ATs (oligonucleotides or antisense oligonucleotides) that inhibit natural antisense transcripts (NAT's). These ATs can upregulate endogenous BDNF expression, but even delivery of these ATs through the BBB is a huge challenge. The existence of the BBB, hindering the penetration of therapeutics and restricting the overall drug uptake, is the major limiting factor for the development, successful translation, and clinical adoption of many treatment strategies for CNS diseases. Therefore, novel techniques and platforms enabling the permanent bypassing of BBB and delivering therapeutics to the CNS have enormous potential.

Figure 10A:
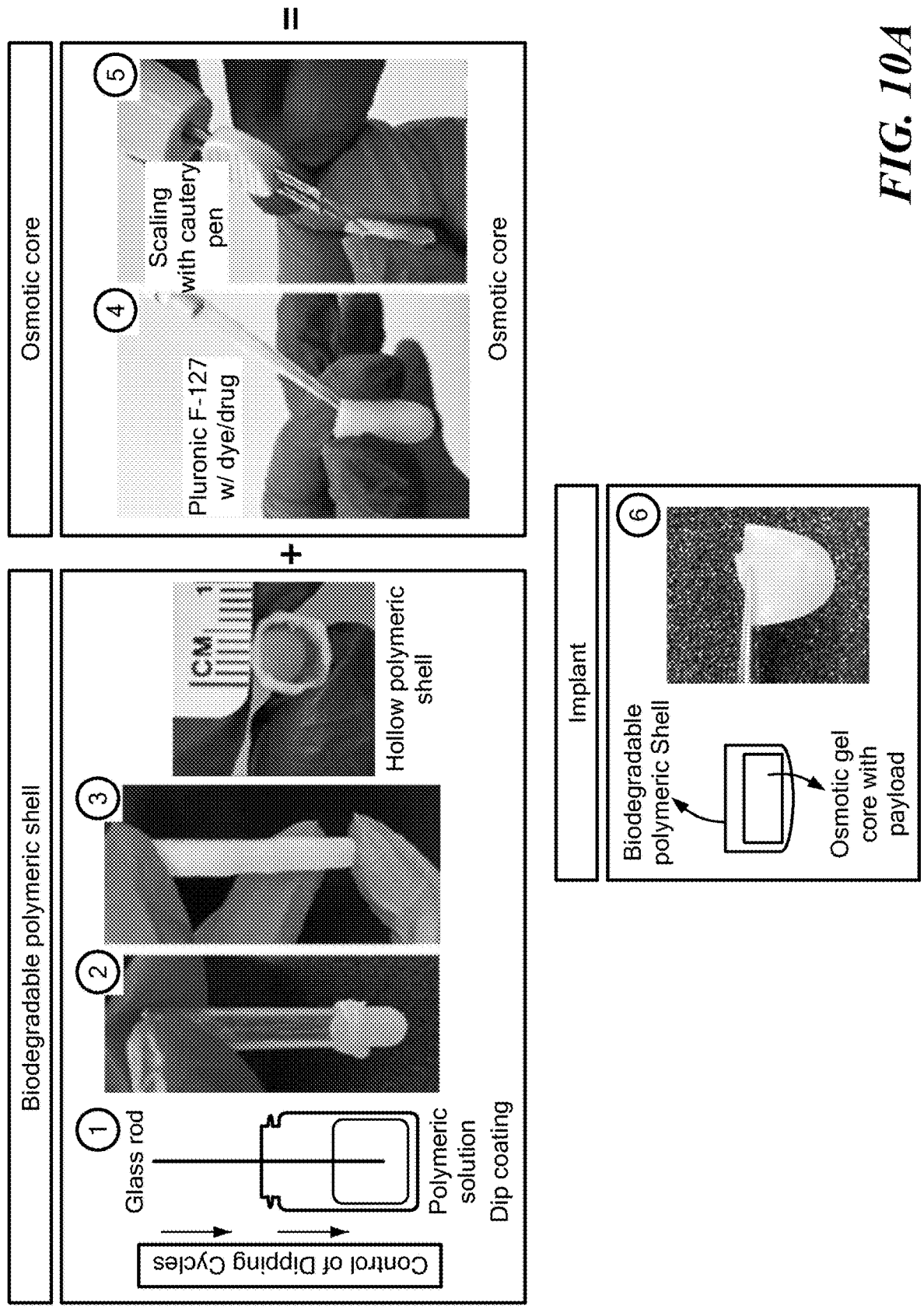
FIG. 10A shows an example of (1) fabrication of a biodegradable polymeric shell: (1) a lubricated cylindrical glass rod acting as the coating substrate is dipped into a concentrated PCL-TFE solution for 9-10 cycles and vacuum dried; (2) the PCL shell is peeled off from the substrate rod such that it forms a (3) hollow reservoir; (4) Pluronic F-127 solution with a dye/drug corresponding to an in vivo dose is pipetted into the hollow shell; (5) the shell is then shortened and its open end is sealed with heat using a cautery pen; (6) the core-shell implant, including an osmotic core entrapping the payload enclosed within a biodegradable shell.

In an example, a polycaprolactone (PCL)-based implant is developed, and in vivo studies are carried out in rats using Brain-Derived Neurotrophic Factor (BDNF) upregulating molecule, called AntagoNAT (AT). The technology can utilize different kinds of implants, which include polymeric cast films, 3D printed implants, electrospun fibrous implants, and injectables, entrapping various therapeutic agents. For a trans-nasal CNS delivery approach, the technology can include a polymeric implant of a core-sheath geometry made by a dip-coating technique, for example, as depicted at the left of FIG. 10A, where a glass rod is depicted dip-coated into a polymeric solution.

Figure 4:
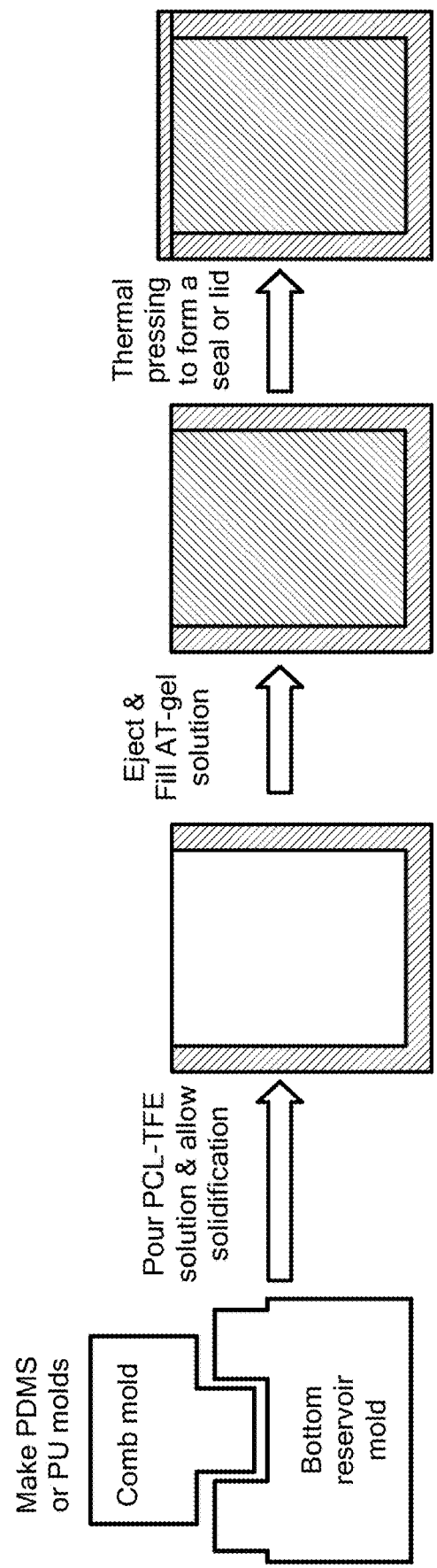
FIG. 4 is a schematic illustration of a microfabrication technique including a form of injection molding, employing the construction of a cavity or mold that matches the shape of the reservoir or device to be made.
Figure 10B:
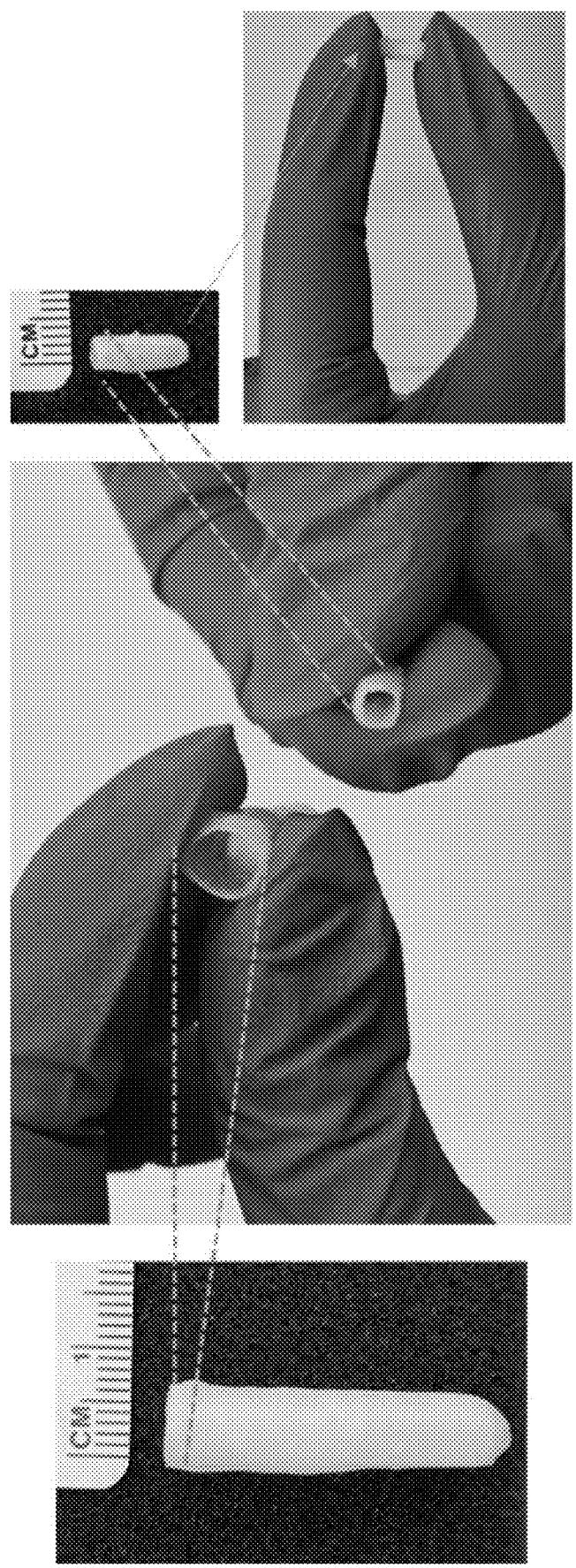
FIG. 10B shows images illustrating flexibility of implant dimensions by control of fabrication parameters. Poly(ε-caprolactone) shells with inner diameters in the range of about 2 mm to about 5 mm are illustrated.
Figure 14:
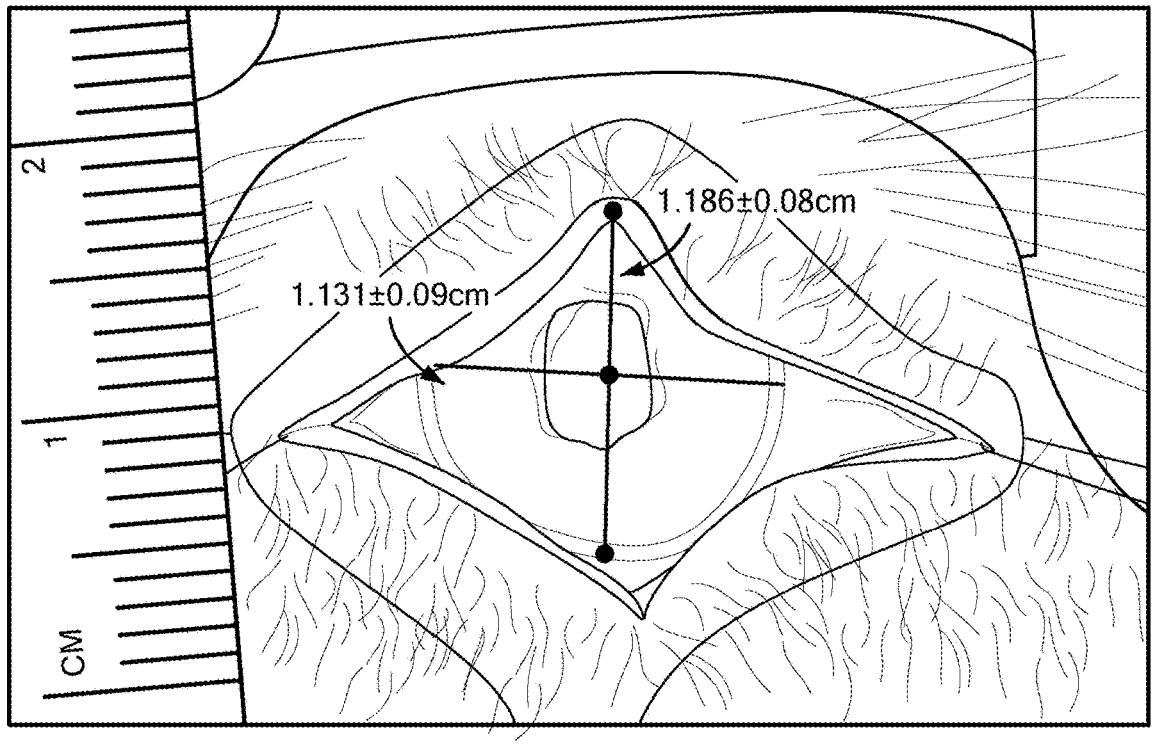
FIG. 14 illustrates example dimensions of the rat submucosal space formed by a MIND (Minimally Invasive Nasal Depot) surgical technique as applied to Sprague Dawley rats. The dimensions were measured with Image J software taking an average of five independent measurements.
Figure 15B:
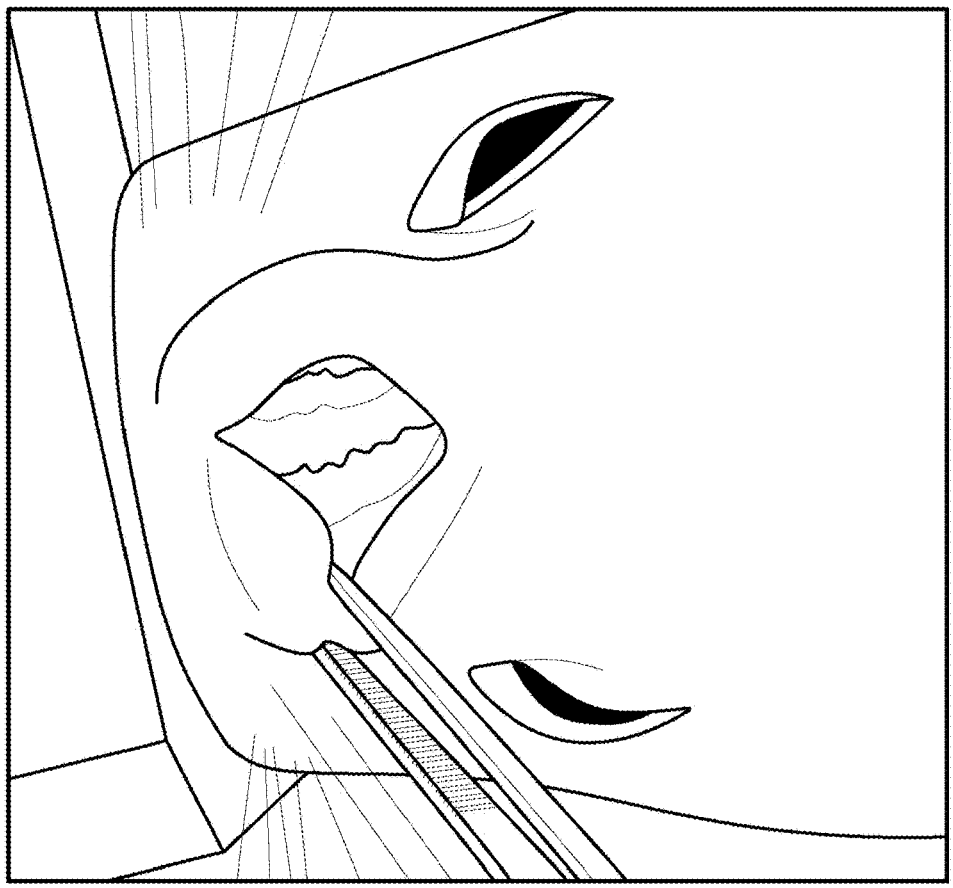
FIGS. 15A-15D show images of in vivo administration of BDNF AntagoNAT (AT) core-shell implant by MIND technique to the submucosal space of naïve Sprague Dawley rats.

The dip-coating techniques can be upscaled by methods of microfabrication. An example of a microfabrication is depicted in FIG. 4, wherein a bottom reservoir mold or an injection mold can be used to fabricate a core-sheath geometry, which is ejected from the mold and filled with a therapeutic agent. To demonstrate the technology, as a first step, a polymeric hollow sheath-like reservoir can be formed by a dip-coating technique (FIG. 10A, left) into which 30% (w/v) Pluronic F127 solution mixed with a drug (therapeutic) solution is filled as a core component (FIG. 10A, center). For this demonstration, poly (ε-caprolactone) (PCL), FDA approved biodegradable polymer with a molecular weight of 50 kDa is chosen as the polymer, owing to its prolonged and slow degradation profile. A polymeric solution of 14 w/v % concentration is prepared by dissolving PCL in 2,2,2-trifluoroethanol (2,2,2-TFE) solvent to form a homogenous solution (coating solution). A cylindrical rod with an average diameter of about 4-5 mm is then dipped into the coating solution, such that 3-4 cm of the rod is completely dipped onto the solution. Dipping cycles can be continued with a 1-2 minute dipping cycle followed by a 30 minute drying in room temperature (about 25° C.), repeated 9 times, so as to form a sheath-like hollow reservoir (FIG. 10B). The hollow reservoir, with a wall thickness in the range of about 0.1 mm-2 mm and one end closed can be easily peeled off or removed from the rod, and it is subjected to overnight drying in vacuum for residual solvent removal. This PCL sheath hollow reservoir can be filled with an appropriate volume of BDNF AntagoNAT (an example oligonucleotide used for therapy of Parkinson's disease for BDNF upregulation) entrapped Pluronic gel corresponding to an animal (rat) dose of 0.15 mg/kg (FIG. 10A, center). The open ends of the sheath reservoir just above the volume of gel can be compressed and sealed with heat (FIG. 10A, center). The size of the implants, depending upon the manufacturing technique used, is not limited and can be planned to fit into a submucosal space of an olfactory epithelium for trans-nasal implant applications. For example, FIG. 14 illustrates example dimensions of a rat submucosal space before an implant is deposited in the space. The overall length of this example implant (FIG. 10A, right; FIG. 15C) having a dip-coated PCL sheath and BDNF AntagoNAT-gel core in the form of a small compressed cylinder can be about 1 cm or less.

This example implant can release the therapeutic, BDNF AntagoNAT, continuously in a prolonged manner by one or both of two mechanisms: 1) diffusion of AT in gel through the pores of hydrophobic PCL sheath; and 2) degradation of PCL sheath at later time points enabling enhanced AT release. In this example, these implants are UV sterilized and implanted into the mucosal cavity of rats (FIG. 15A) by a surgical technique of removing the nasal bone (FIG. 15B) and exposing the olfactory mucosa for implantation (FIG. 15C). The animals are healthy throughout the study period with no visible signs of inflammation or infection (e.g., FIG. 22).

Figure 2:
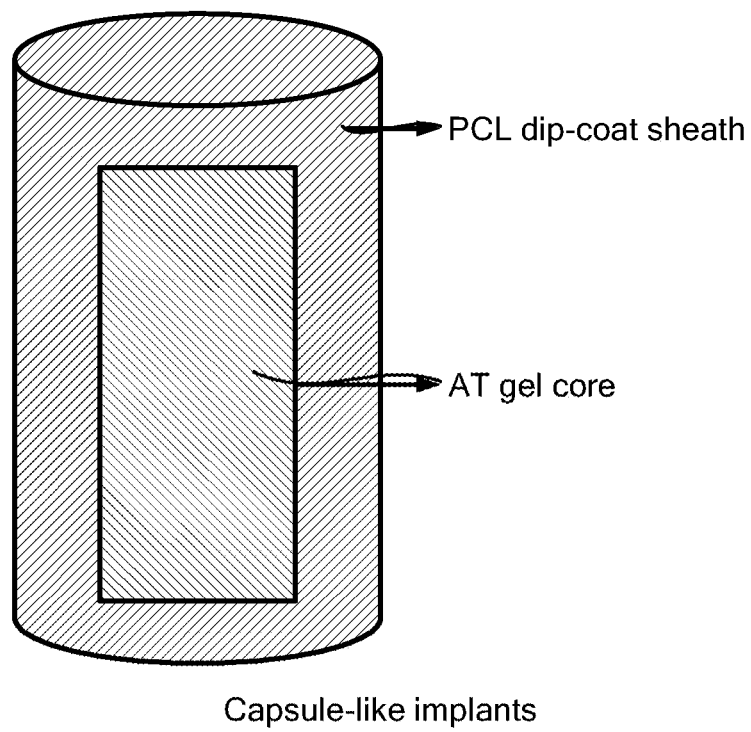
FIG. 2 is a schematic illustration of an embodiment of a capsule-like implant including a polycaprolactone (PCL)-based dip-coat sheath and an AntagoNAT (AT) gel core.

An implant as described herein can be fabricated by a variety of techniques. FIG. 2 illustrates a capsule-like implant having a support body in the form of an outer sheath surrounding an inner core or reservoir. The sheath can be formed of a biodegradable polymer (such as PCL in this example). The sheath can optionally include pores, depending on the polymer compositions used. The core or reservoir can be filled with a therapeutic agent. The therapeutic agent can include a gel (such as AT gel in this example).

Figure 3:
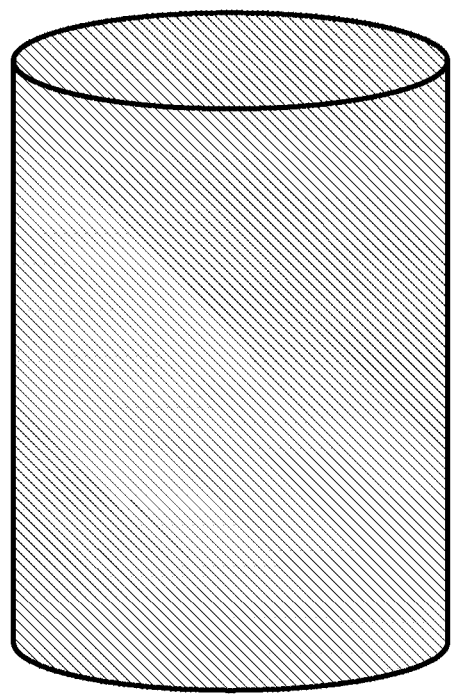
FIG. 3 is a schematic illustration of an example of a tablet-like implant.

FIG. 3 is a schematic illustration of a tablet-like implant. The implant can provide a support body in the form of a matrix of a biodegradable polymer and a therapeutic agent supported by or within the matrix. The matrix can include a polymer network that releases a therapeutic agent as the biodegradable polymer decomposes over time, after implantation.

Manufacturing techniques utilized to produce the implants can be any suitable techniques in the art. The techniques can optionally include customized sizes and shapes, sterilization, irradiation (e.g., to change crosslinking and/or hydrophilicity/hydrophobicity of a polymer). FIG. 4 illustrates a microfabrication technique of molding a support body and filling the reservoir of the support body with a therapeutic agent. This example is a form of injection molding employing the construction of a cavity or mold that matches the shape of the reservoir or device to be made. At the right of FIG. 4, a seal is formed over the AT-gel solution.

Figure 5:
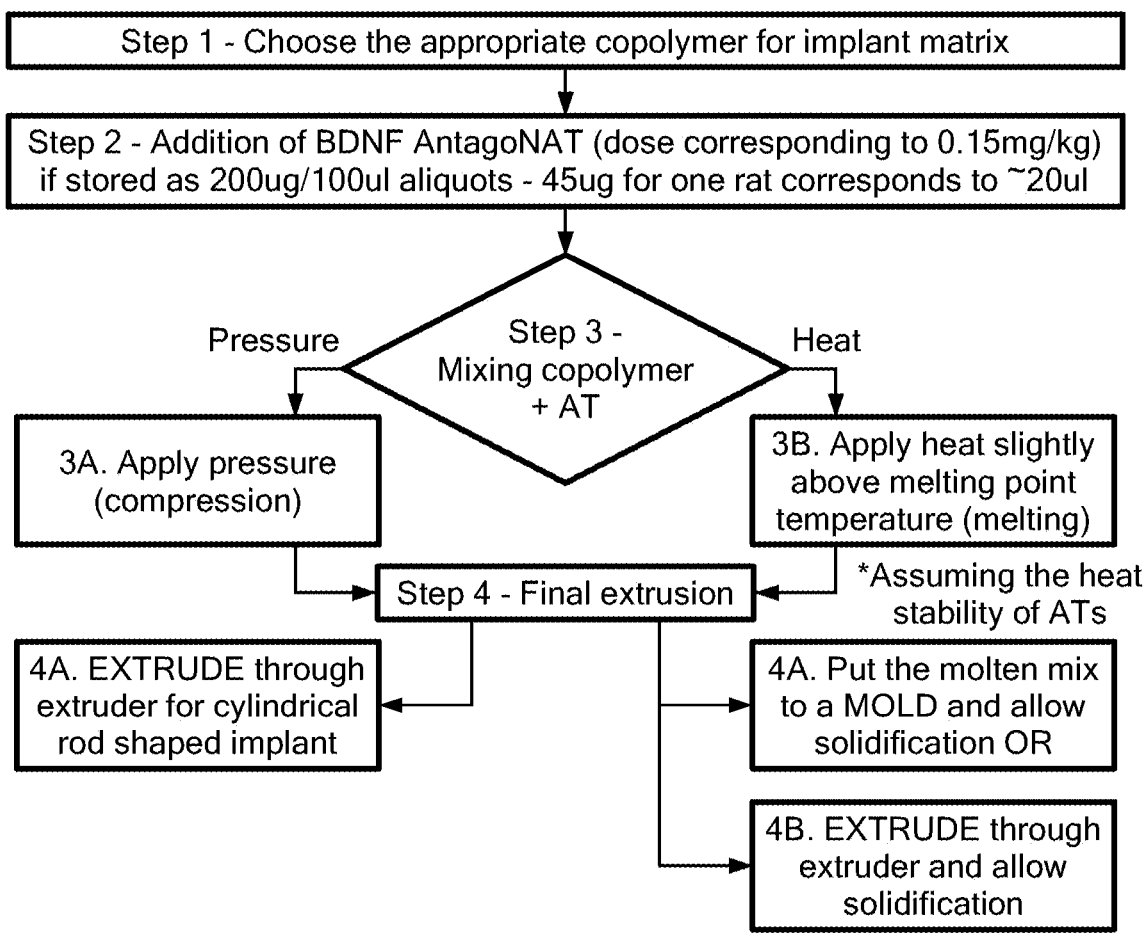
FIG. 5 is a schematic illustration of steps of a fabrication of a hydrogel based cylindrical (tablet type) implant.

FIG. 5 illustrates example techniques of fabricating a hydrogel based cylindrical (tablet type) implant, in which a biodegradable polymer(s) and a therapeutic agent(s) are mixed. The mixture can be compressed and/or heated, and can be formed into the implant by, for example, extrusion, molding, 3D printing, or a combination thereof.

Other fabrication techniques can include use of 3D printing technologies such as stereolithography (SLA) printer or thermal inkjet printer to electrically heat a printhead to produce air pressure pulses to force vapor droplets from a nozzle. An acoustic printer can use pulses formed by piezoelectric or ultrasound pressure. A microextrusion printer can use pneumatic or mechanical (piston or screw) dispensing systems to extrude continuous beads and/or cells. A laser-assisted printer can use a laser focused on an absorbing substrate to generate pressures that propel a material containing cells onto a collector substrate.

Figures 6, 7:
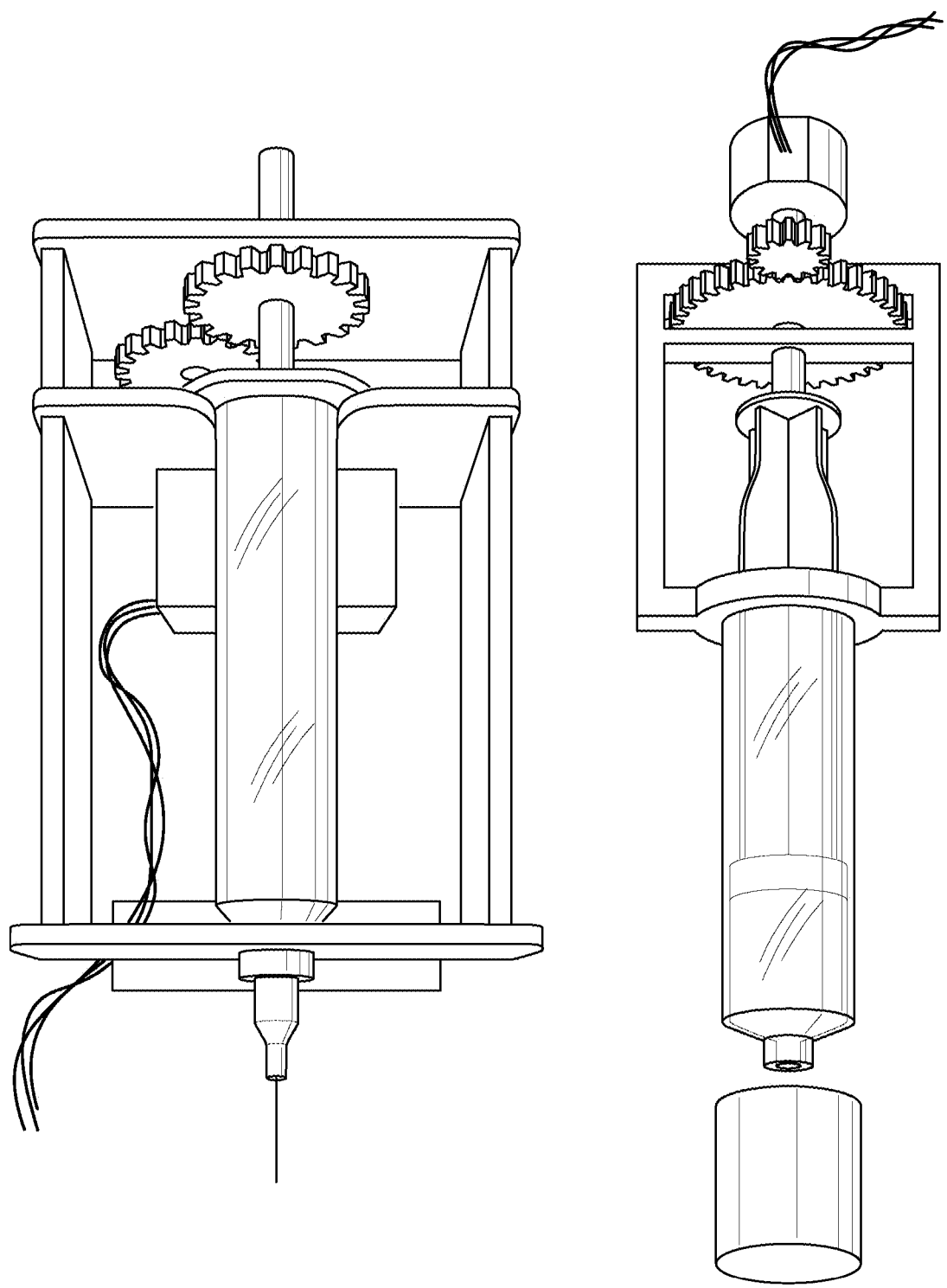
FIG. 6 is an illustration of a solder paste type extruder that can be used for fabrication of implants.
FIG. 7 illustrates a thick paste extrusion device that can be used for fabrication of implants.
Figure 8:
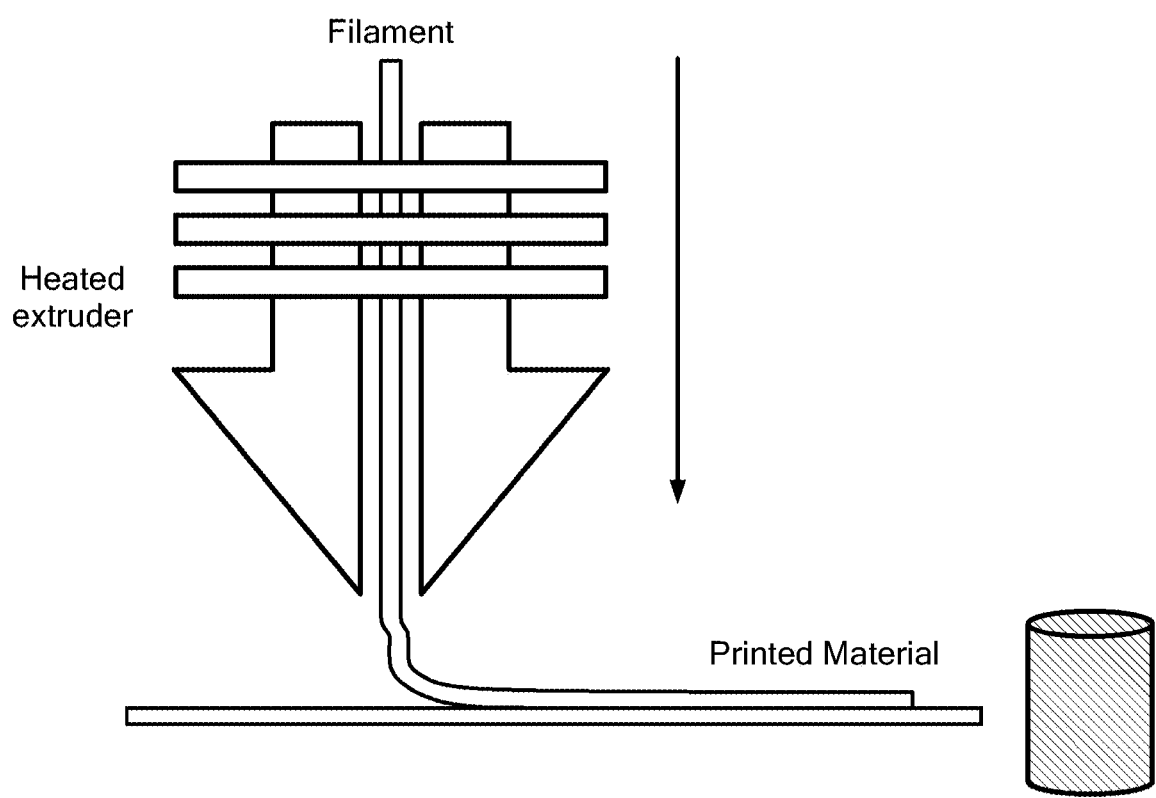
FIG. 8 illustrates a fused deposition 3D modeling printer that can be utilized for fabrication of implants.
Figure 9:
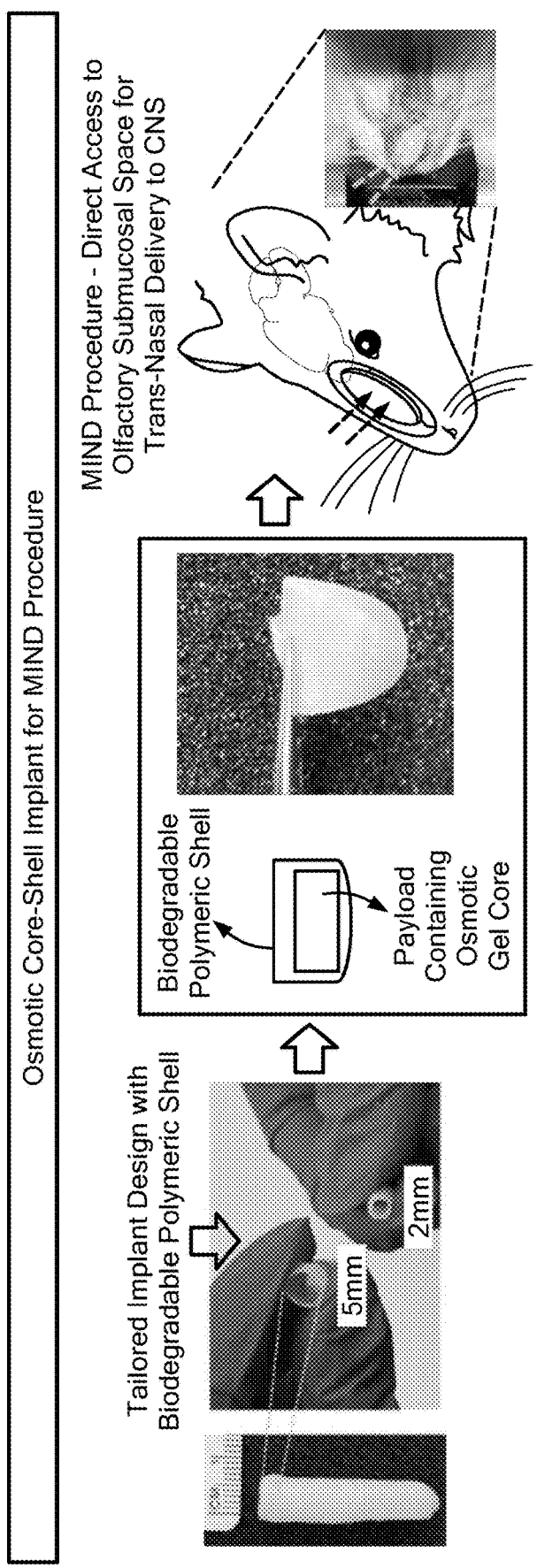
FIG. 9 shows an example of formation of a biodegradable polymeric shell (left), addition of a payload to the shell (center), and implantation in an olfactory submucosal space (right).

Examples of PEG PCL copolymers usable in 3D printing are described in Güney, et al., 2018, which is incorporated by reference herein in its entirety; and Shaukat, et al., 2019, which is incorporated by reference herein in its entirety. For example, poly(ε-caprolactone)-b-poly(ethylene glycol)-b-poly(ε-caprolactone) co-polymers, optionally end-terminated with thermoplastic polyurethane (TPU), can be utilized for fused deposition modelling by extruding the polymers into filaments. In these example co-polymers, the number average molecular weights (Mn) of the poly(ethylene glycol) (PEG) can have a molecular weight in the range from about 5 kilodaltons (kDa) to about 15 kDa, while providing a 3D printer extrusion temperature of less than about 180° C. The Mn of the entire length of the co-polymer can be less than about 30 kDa-50 kDa. FIG. 6 illustrates an example of an extrusion device. FIG. 7 is an illustration of a thick paste extruder for 2D or 3D printing. FIG. 8 is an illustration of a fused deposition 3D modeling printer that can be utilized to form implants. The implants can be fabricated with various 2D and 3D printing techniques for the fabrication of hydrogel based cylindrical (tablet type) implants, employing components of inkjet, micro-extrusion, and laser-assisted bioprinters. A filament including the polymers can be formed using, for example, an extruder depicted in FIG. 6 or FIG. 7. The filament can be supplied as illustrated at the top of FIG. 8 to a heated extruder, which is controlled by printing software to form an implant having a desired shape.

First biodegradable polymers that can be used for fabrication of the support body of the implant can include or be fabricated entirely from natural, synthetic, and semi-synthetic polymer types. Natural polymers include different types of gelatin and their derivatives, chitosans and their derivatives, starches and their derivatives, celluloses and their derivatives and so on. Synthetic biodegradable polymers can be either commercially available or synthesized specifically for this application. Specific examples include poly(D,L-lactide-co-glycolide) (PLGA) and its copolymers, PCL and its copolymers, polydioxanones, polyanhydrides, polyorthoesters and others known to those skilled in the art.

A specific example of a suitable first biodegradable polymer is poly(ethylene glycol)-block-poly(ε-caprolactone) methyl ether. In an example, a polyether (e.g., PEG) can be utilized with another polymer or a polyester. Suitable PEG diblock copolymers based on examples of molecular weight, melting point, and degradation time frame can include the following shown in Table 1, Table 2, and Table 3:

TABLE 1

| PEG-PLA Diblock Copolymers | | |
|---|---|---|
| PEG-PLA Diblock Copolymers | Melting Point | Degradation Time |
| Carboxylic acid-poly(ethylene glycol)-b-poly(D,L lactide) PEG average Mn 5,000, PDLA average Mn 16,000 | NA | NA |
| Poly(ethylene glycol) methyl ether-block-poly(D,L lactide) PEG average Mn 2,000, PDLLA average Mn 2,000 | 244-248° C. | 2-4 weeks |
| Poly(ethylene glycol) methyl ether-block-poly(D,L lactide)-block-decane PEG average Mn 2,000, PDLLA average Mn 2,000 | 29-33° C. | 2-5 weeks |
| Poly(ethylene glycol)-block-polylactide methyl ether PEG average Mn 750, PLA average Mn 1,000 | NA | NA |

TABLE 1-continued

PEG-PLA Diblock Copolymers

| PEG-PLA Diblock Copolymers | Melting Point | Degradation Time |
|---|---|---|
| Poly(ethylene glycol)-block-polylactide methyl ether PEG average Mn 350, PLA average Mn 1,000 | NA | NA |
| Poly(ethylene oxide)-block-polylactide, 4-arm poly(ethylene oxide) Mn ~2,500, PLA average Mn ~3,500 | NA | NA |
| Poly(L-lactide)-block-poly(ethylene glycol)methyl ether PLLA average Mn ~5,000, PEG average Mn ~5,000 | 141° C. (peak) | NA |

TABLE 2

PEG-PLGA Diblock Copolymers

| PEG-PLGA Diblock Copolymers | Melting Point | Degradation Time |
|---|---|---|
| Carboxylic acid-poly(ethylene glycol)-b-poly(lactide-co-glycolide) PEG average Mn 5,000, PLGA average Mn 20,000, lactide:glycolide 50:50 | NA | NA |
| N-Hydroxysuccinimide ester-poly(ethylene glycol)-b-poly(D,L lactide) PEG average Mn 5,000, PDLA average Mn 16,000 | NA | NA |
| Poly(ethylene glycol) methyl ether-block-poly(lactide-co-glycolide) PEG average Mn 5,000, PLGA Mn 15,000, lactide:glycolide 50:50 | NA | NA |
| Poly(ethylene glycol) methyl ether-block-poly(lactide-co-glycolide) PEG average Mn 5,000, PLGA Mn 20,000, lactide:glycolide 50:50 | NA | NA |
| Poly(ethylene glycol) methyl ether-block-poly(lactide-co-glycolide) PEG average Mn 5,000, PLGA Mn 10,000, lactide:glycolide 50:50 | NA | NA |
| Poly(ethylene glycol) methyl ether-block-poly(lactide-co-glycolide) PEG average Mn 5,000, PLGA Mn 5,000, lactide:glycolide 50:50 | NA | NA |
| Poly(ethylene glycol) methyl ether-block-poly(lactide-co-glycolide) PEG average Mn 5,000, PLGA Mn 10,000, lactide:glycolide 80:20 | NA | NA |
| Poly(ethylene glycol) methyl ether-block-poly(lactide-co-glycolide) PEG average Mn 5,000, PLGA Mn 5,000, lactide:glycolide 80:20 | NA | NA |
| Poly(ethylene glycol) methyl ether-block-poly(lactide-co-glycolide) PEG average Mn 2,000, PLGA Mn 10,000, lactide:glycolide 80:20 | NA | NA |
| Poly(ethylene glycol) methyl ether-block-poly(L-lactide-co-glycolide) PEG average Mn 5,000, PLGA average Mn 25,000, lactide:glycolide 50:50 | NA | NA |
| Poly(ethylene glycol) methyl ether-block-poly(lactide-co-glycolide) PEG average Mn 5,000, PLGA Mn 55,000 | 254-259° C. | 1-4 weeks |
| Poly(ethylene glycol) methyl ether-block-poly(lactide-co-glycolide) PEG average Mn 5,000, PLGA Mn 7,000 | 38-43° C. | 1-4 weeks |
| Poly(ethylene glycol) methyl ether-block-poly(lactide-co-glycolide) PEG average Mn 2,000, PLGA average Mn 11,500 | 298-303° C. | 1-4 weeks |
| Poly(ethylene glycol) methyl ether-block-poly(lactide-co-glycolide) PEG Mn 2,000, PLGA Mn 4,500 | 241-246° C. | 1-4 weeks |
| Poly(ethylene glycol) methyl ether-block-poly(lactide-co-glycolide) PEG average Mn 2,000, PLGA Mn 3,000, lactide:glycolide 50:50 | NA | NA |
| Poly(ethylene glycol) methyl ether-block-poly(lactide-co-glycolide) PEG average Mn 5,000, PLGA Mn 5,000, lactide:glycolide 80:20 | NA | NA |
| Poly(ethylene glycol) methyl ether-block-poly(lactide-co-glycolide) PEG average Mn 5,000, PLGA Mn 15,000, lactide:glycolide 80:20 | NA | NA |
| Poly(D,L-lactide-co-glycolide)(50:50)-b-poly(ethylene glycol) 10k-2k | NA | NA |
| Poly(lactide-co-glycolide)-b-poly(ethylene glycol)-b-poly(lactide-co-glycolide) average Mn (1,600-1,500-1,600), lactide:glycolide 75:25 | NA | NA |
| Poly(lactide-co-glycolide)-b-poly(ethylene glycol)-b-poly(lactide-co-glycolide) average Mn (1,700-1,500-1,700), lactide:glycolide (95:5) | NA | NA |
| Poly(D,L-lactide-b-glycolide) lactide:glycolide 50:50 amine terminated, average Mn 5,000 | NA | NA |

TABLE 3

PEG-PCL Diblock Copolymers

| PEG-PCL Diblock Copolymers | Melting Point | Degradation Time |
|---|---|---|
| Allyl-poly(ethylene glycol)-b-poly(ε-caprolactone) PEG average Mn 5,000, PCL average Mn 5,000 | NA | NA |
| Amine-poly(ethylene glycol)-b-poly(ε-caprolactone) PEG average Mn 5,000, PCL average Mn 5,000 | NA | NA |
| Carboxylic acid-poly(ethylene glycol)-b-poly(ε-caprolactone) PEG average Mn 5000, PCL average Mn 5000 | NA | NA |

TABLE 3-continued

PEG-PCL Diblock Copolymers

| PEG-PCL Diblock Copolymers | Melting Point | Degradation Time |
|---|---|---|
| N-Hydroxysuccinimide ester-poly(ethylene glycol)-b-poly(ε-caprolactone) PEG average Mn 5,000, PCL average Mn 5,000 | NA | NA |
| Poly(ethylene glycol) methyl ether-block-poly(ε-caprolactone) PEG average Mn 5,000, PCL average Mn 25,000, PDI ≤1.6 | NA | NA |
| * Poly(ethylene glycol)-block-poly(ε-caprolactone) methyl ether PCL average Mn ~5,000, PEG average Mn ~5,000 | 52.8-56.1° C. | >12 months |
| Poly(ethylene glycol)-block-poly(ε-caprolactone) methyl ether PCL average Mn ~13,000, PEG average Mn ~5,000 | 58.8-60.7° C. | >12 months |
| * Poly(ethylene glycol)-block-poly(ε-caprolactone) methyl ether PEG average Mn ~5,000, PCL average Mn ~32,000 | 54.2-55.9° C. | >12 months |
| Poly(ethylene oxide)-block-polycaprolactone, 4-arm PEG average Mn ~2,500 | 53-55° C. (lit.) | >12 months |
| Pyridyl disulfide-poly(ethylene glycol)-b-poly(ε-caprolactone) PEG average Mn 5000, PCL average Mn 5000 | NA | NA |
| Thiol-poly(ethylene glycol)-b-poly(ε-caprolactone) PEG average Mn 5000, PCL average Mn 5000 | NA | NA |

* Listed as Biodegradeable Polymers for 3D Printing in Sigma Aldrich website

As used herein, a biodegradable polymer is a polymer susceptible to degradation (or biodegradation) after implantation into an organism, wherein the degradation is accompanied by lowering of the polymer's molar mass. The biodegradation can proceed, for example, by hydrolysis, by contact with nasal mucus, by catalytic activity of other enzymes, or by a combination of factors including a wide variety of biological activities. The support body encloses or contains a reservoir, i.e., an open space that can be filled with a polymer matrix, such as a hydrogel. The support body can include openings and/or pores connecting the reservoir with the environment outside the support body. The reservoir can be filled with a polymer network or matrix that contains a second biodegradable polymer which forms the polymer matrix.

Figure 20A:
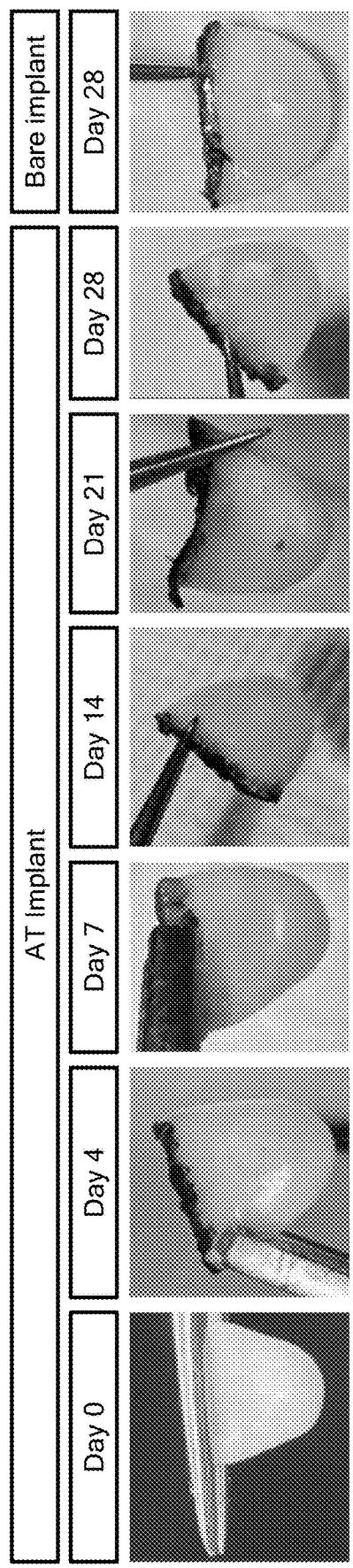
FIG. 20A shows images of AT implants explanted from rat submucosal space at different time points, and a bare implant explanted after day 28 is shown at far right.
Figure 20B:
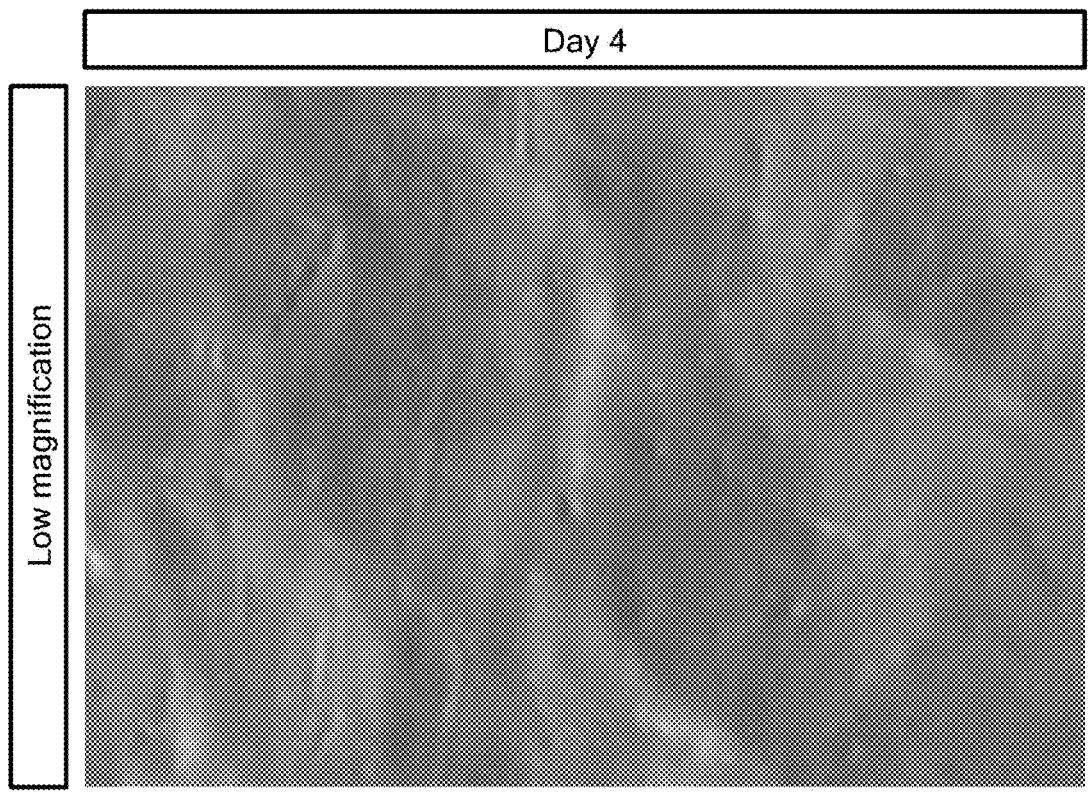
FIGS. 20B-20F show morphology changes of implants with time evaluated by FESEM analysis of explanted implants. The white arrows in FIG. 20F highlight the presence of cracks or crevices on the implant surface at the day 28 time-point.
Figure 20B:
Figure 20C:
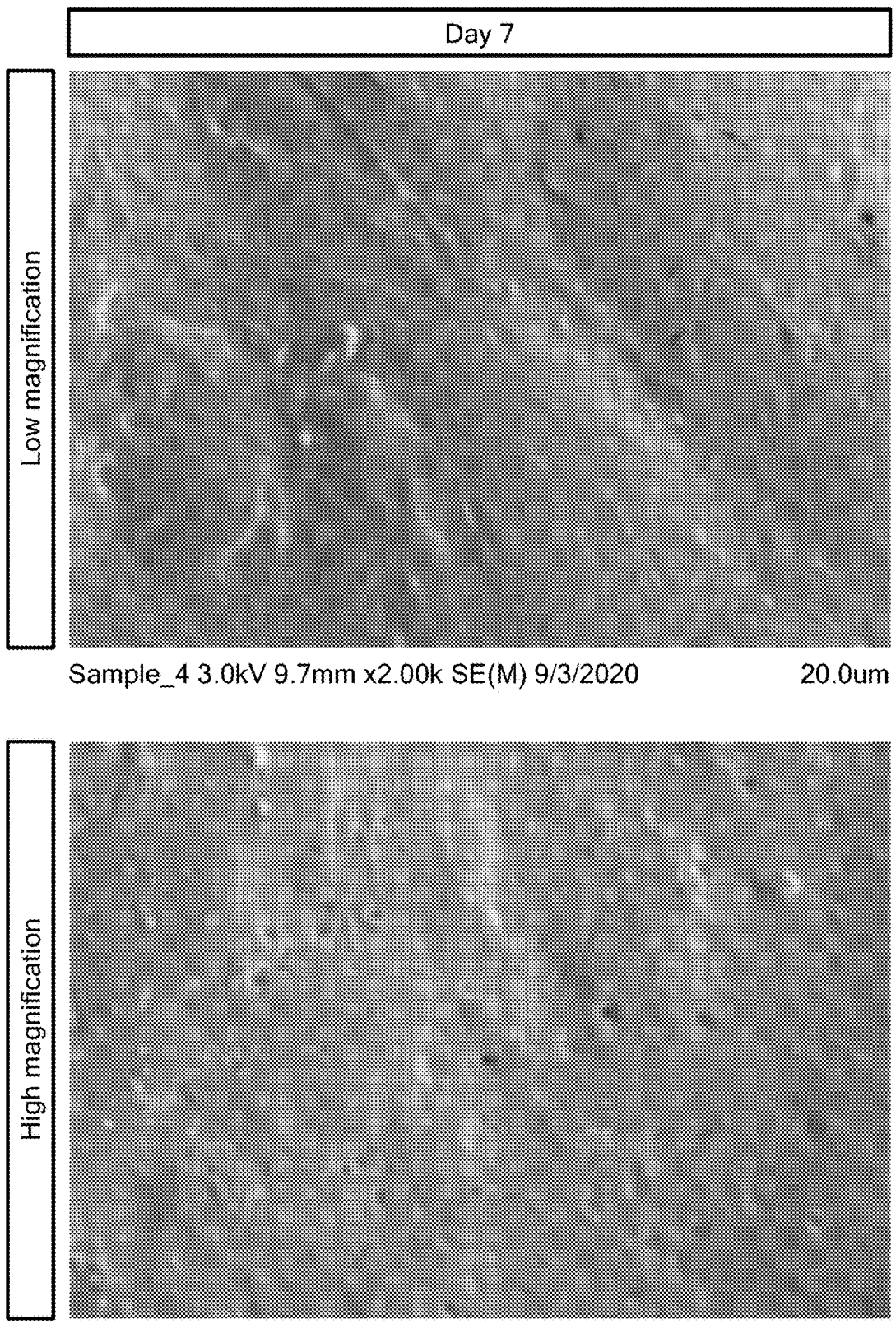
Figure 20D:
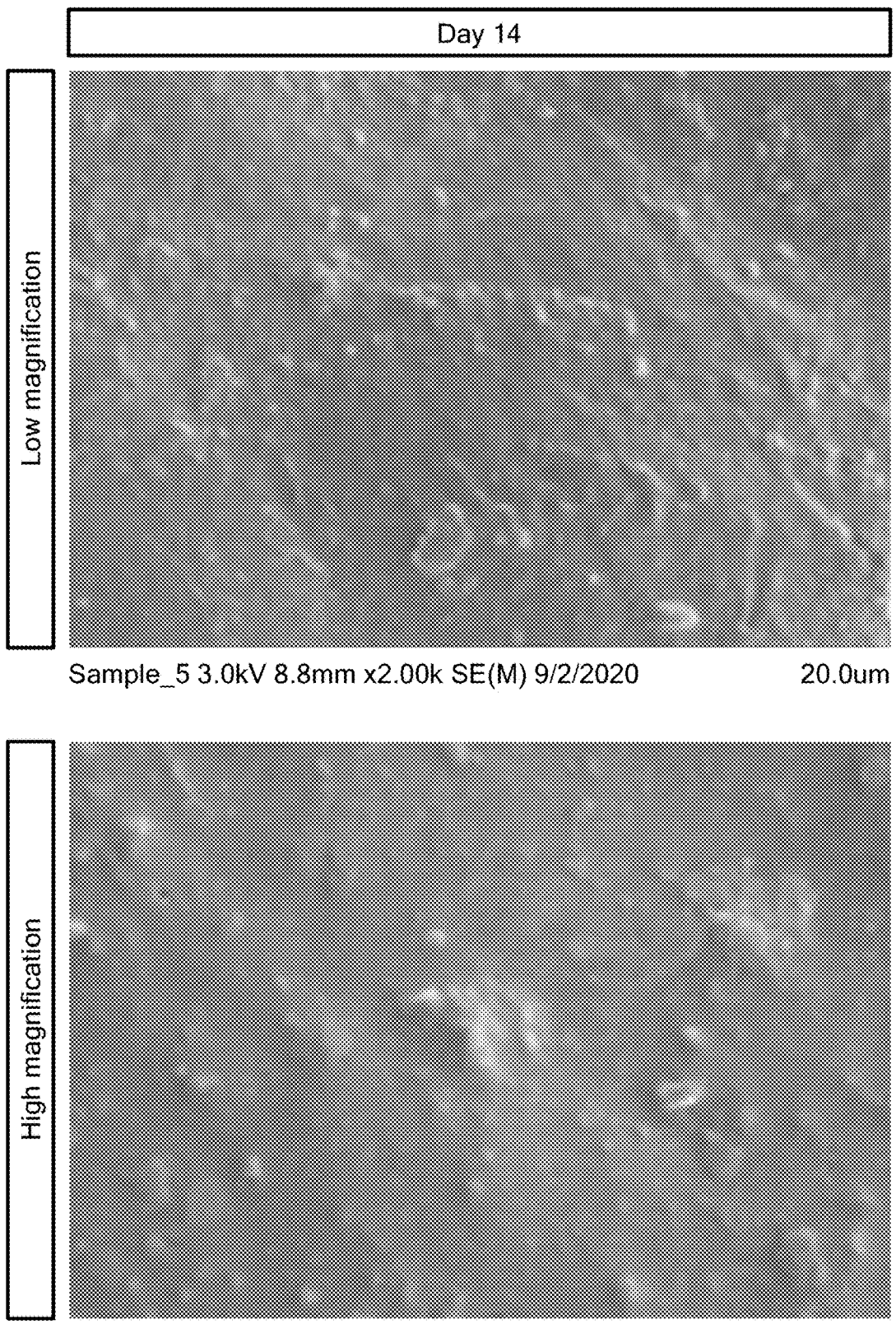
Figure 20E:
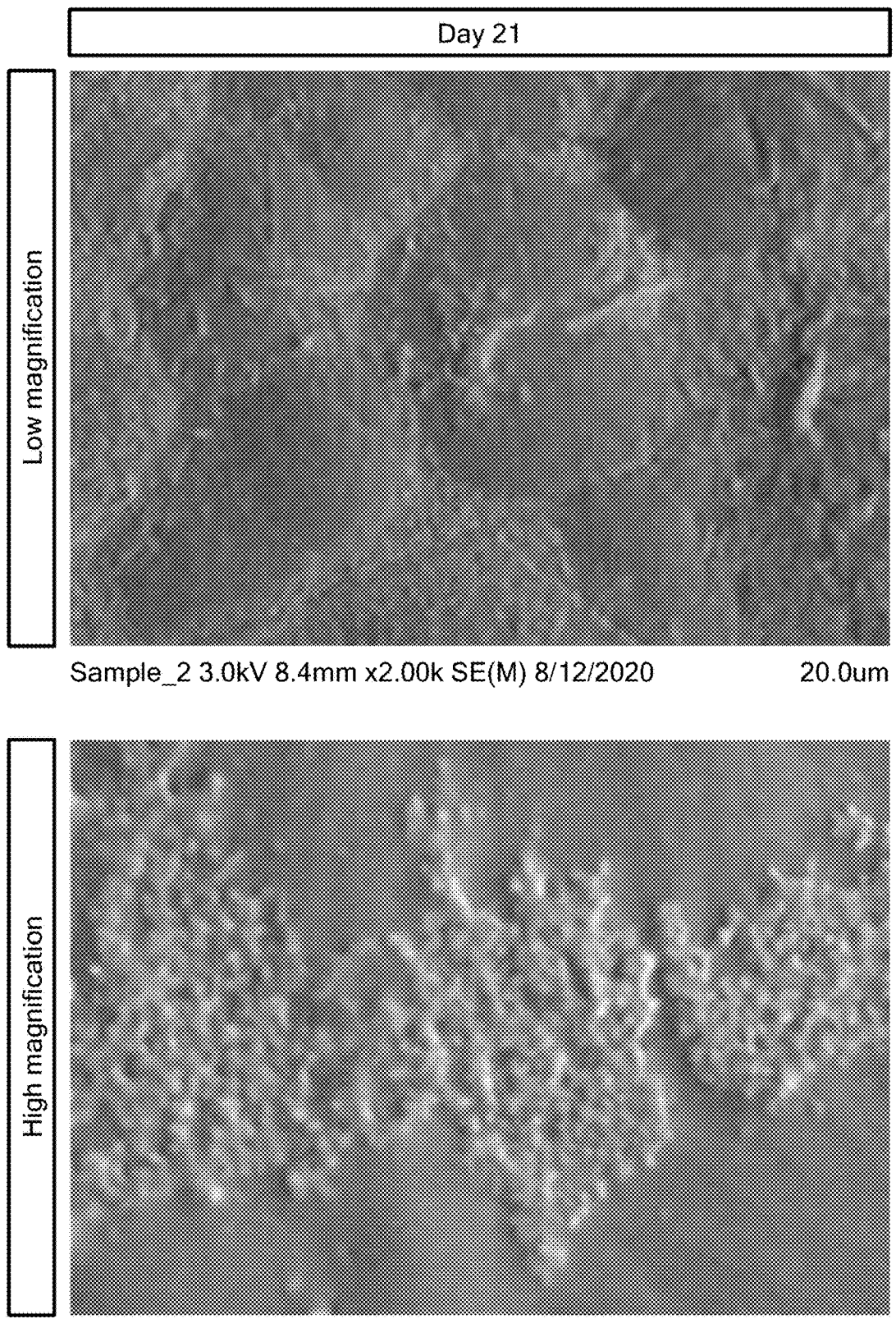
Figure 20F:
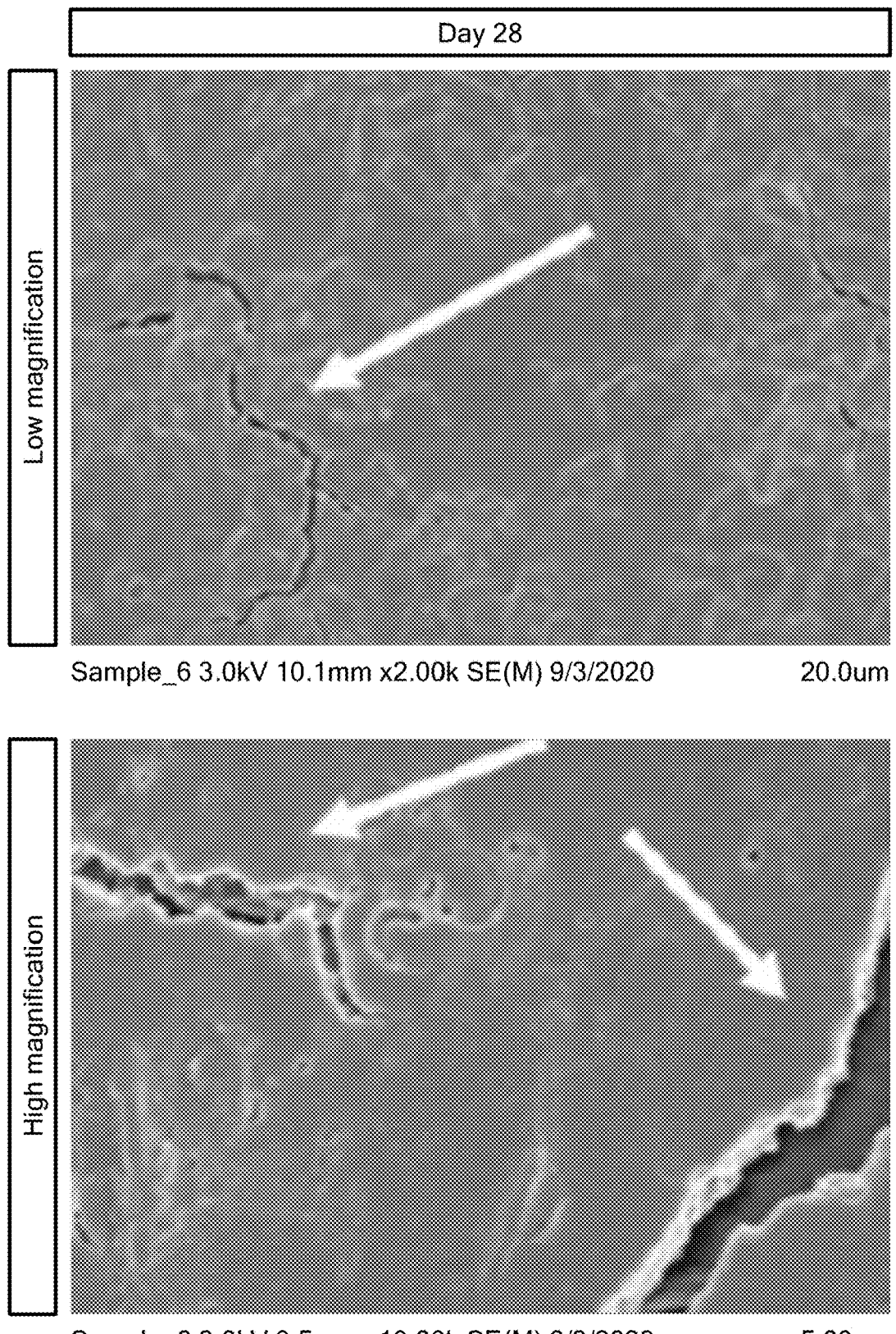
Figure 21A:
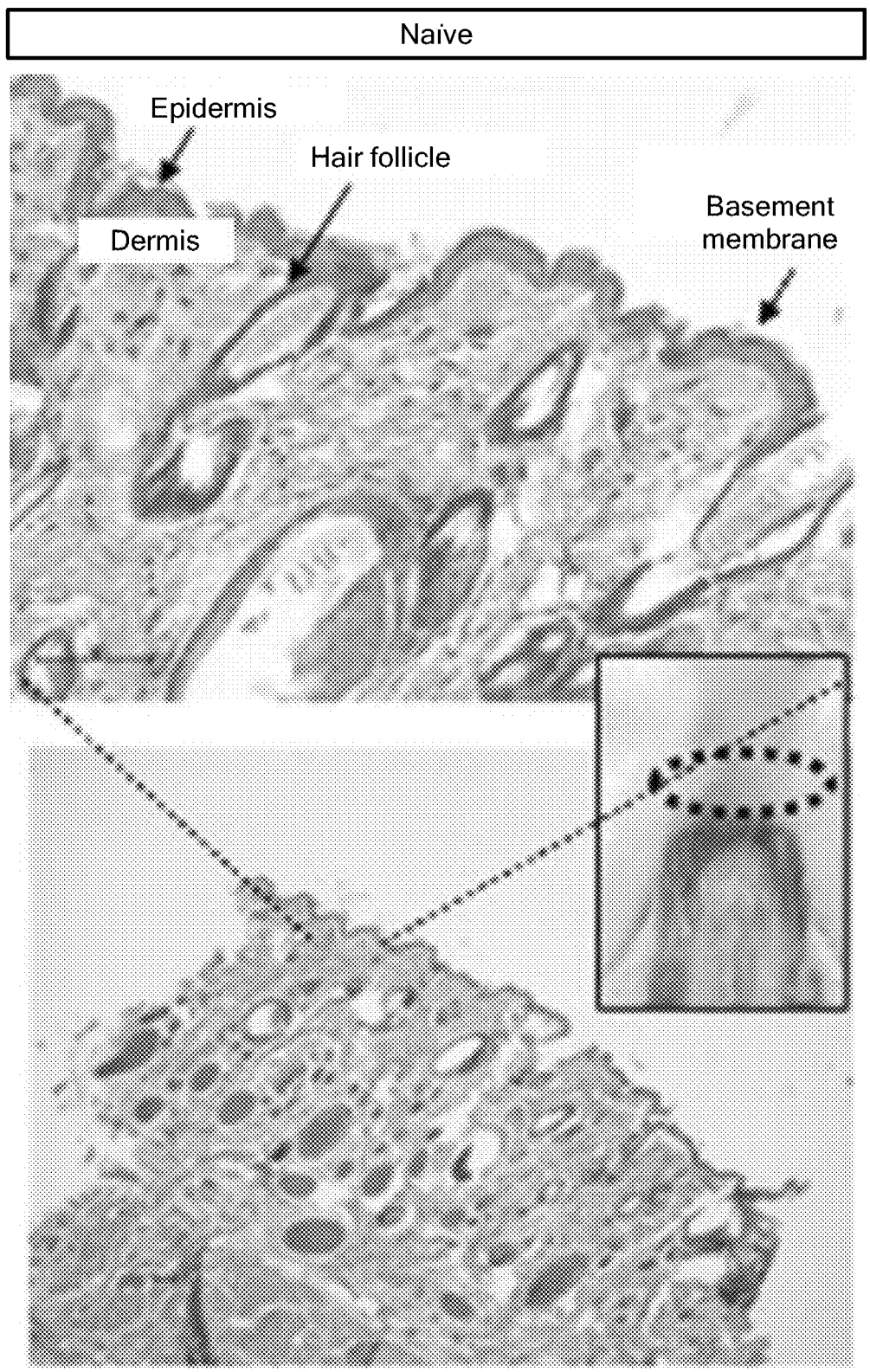
FIGS. 21A-21G show histological evaluation of nasal tissues retrieved from the MIND implantation site of rats after euthanasia at different timepoints (H & E stained images). The scale bar at lower left corresponds to 100 μm. The inset images show the photographs of tissue with the implants at different time points.
Figure 21B:
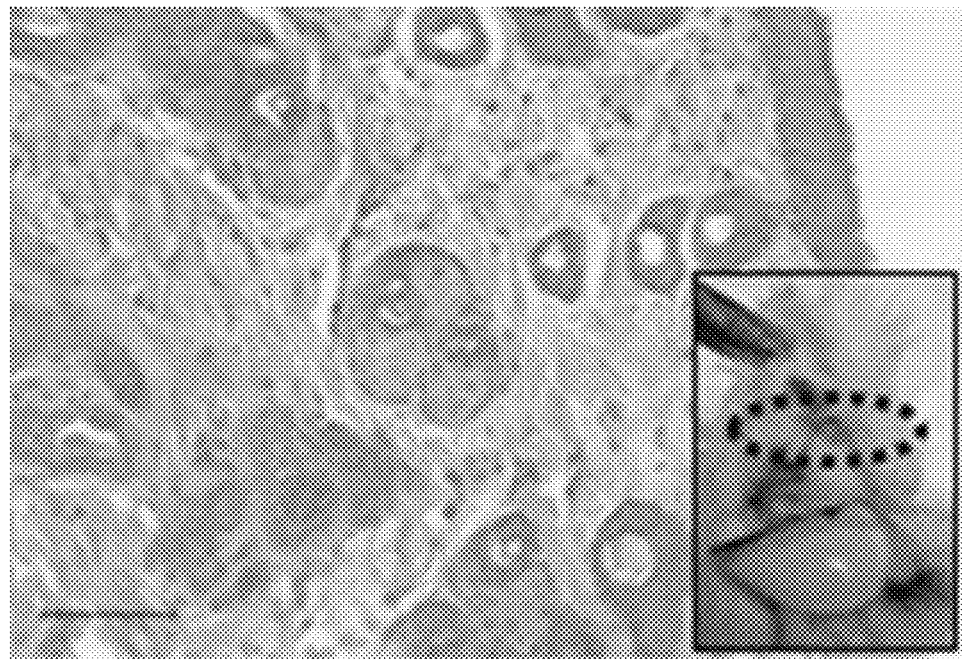
Figure 21C:
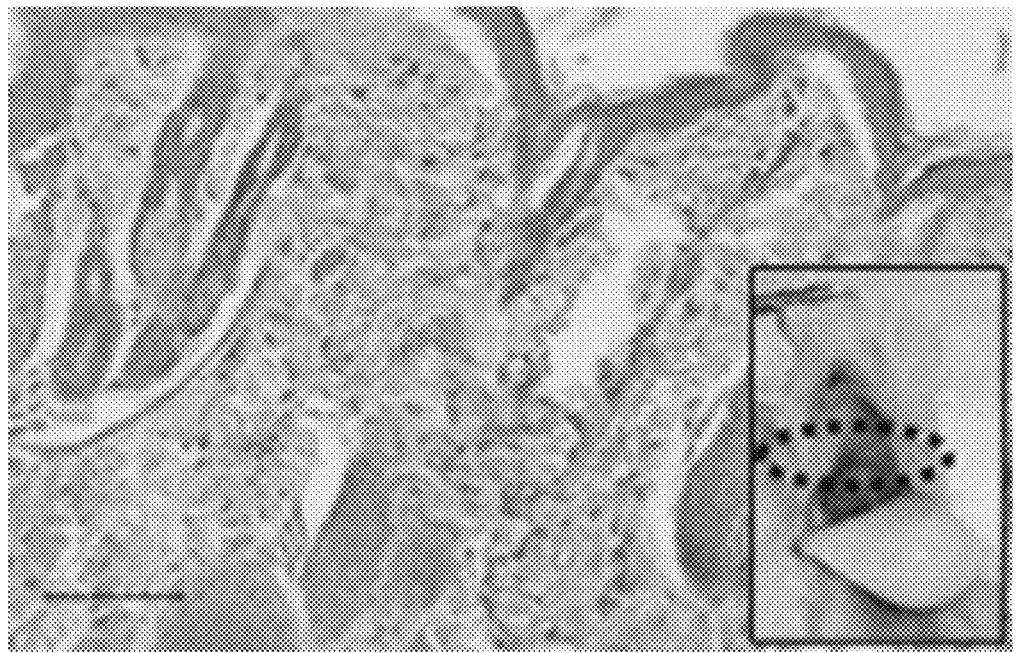
Figure 21D:
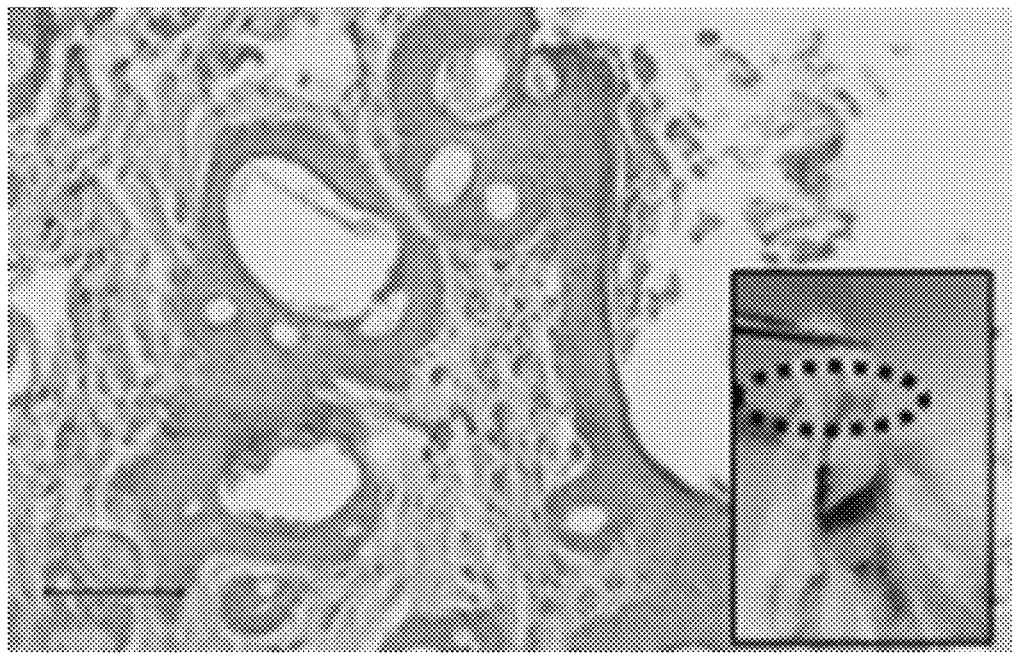
Figure 21E:
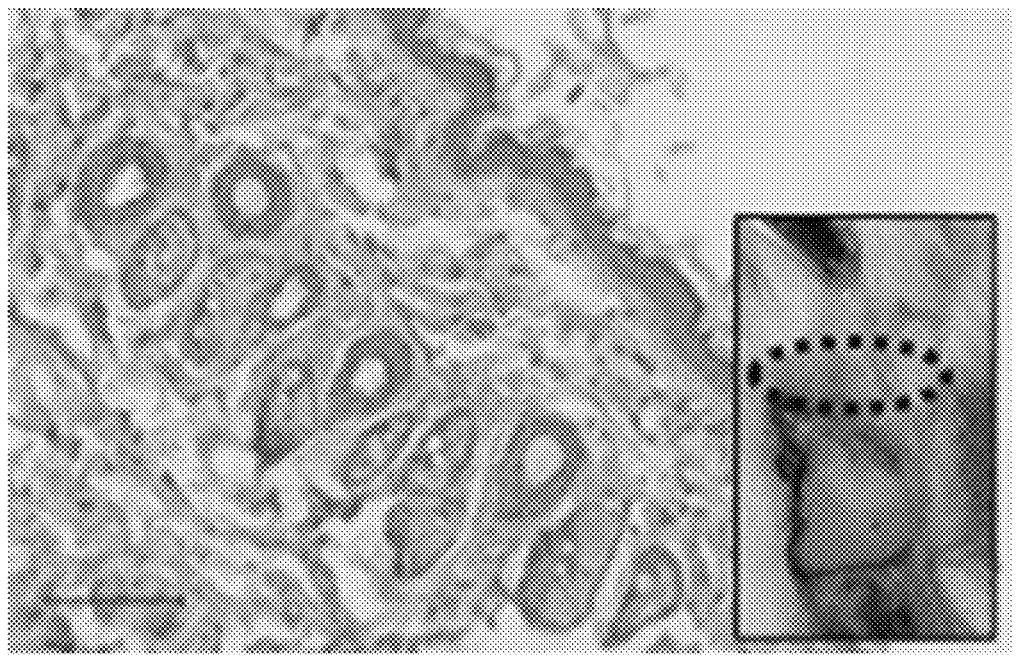
Figure 21F:
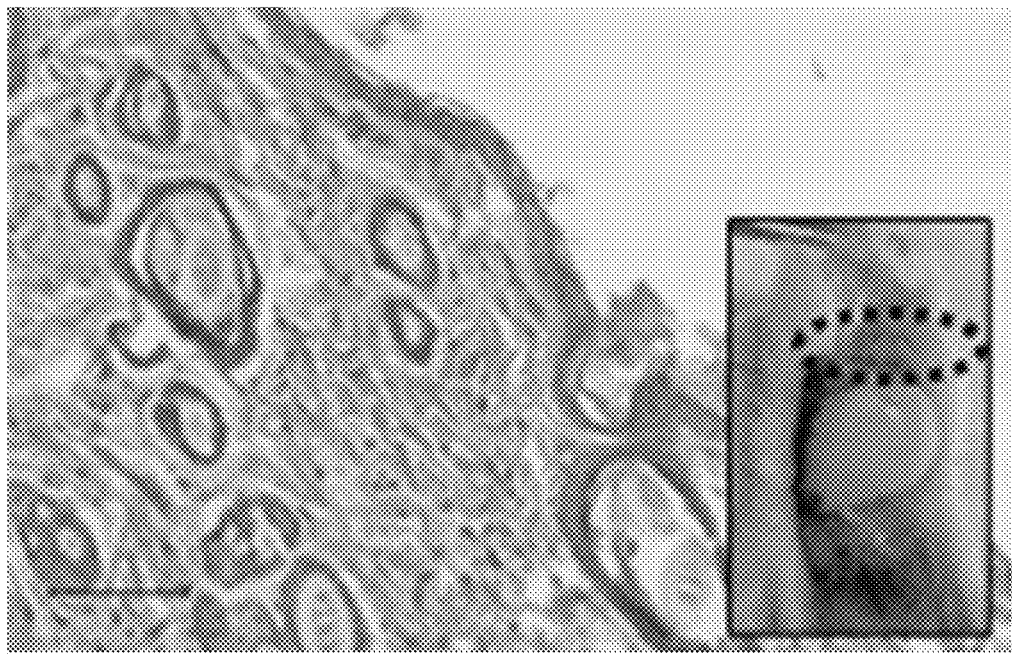
Figure 21G:
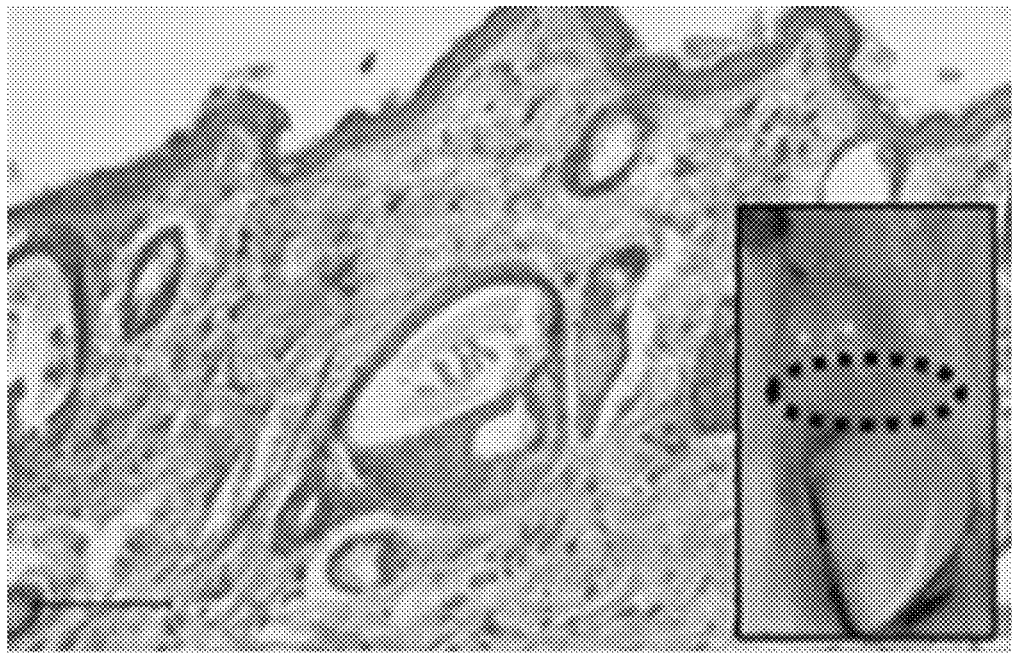

The biodegradable polymers disclosed herein are capable of controlled rates of degradation, for example, by selecting different copolymers, by changing pore size, by selecting a thickness of the polymer, or by utilizing layers (e.g., core-shell) of polymers of varying thicknesses. When a polymer is utilized as an outer shell or hollow sheath, the term "biodegrades" can refer to cracking of an outer shell as depicted by the arrows in FIG. 20F or pores as depicted in FIG. 20C.

In an example, a hydrophilic or hydrophobic outer sheath polymer can include pores and a core-shell configuration, wherein the polymeric outer sheath around the core acts as a barrier layer to delay and further control the release profile of a therapeutic agent. The size of the pores can be adjusted, for example, by utilizing different molecular weights of PEG with poly(ε-caprolactone) in an outer sheath polymer. The pores can allow diffusion of a therapeutic agent through the outer sheath polymer to contact the olfactory mucosal epithelium. Pores can increase or decrease in size after implantation. The size of the pores can be in the range from about 0.01 μm to about 100 μm, in the range from about 1 μm to about 100 μm, in the range from about 5 μm to about 50 μm, or in the range from about 10 μm to about 30 μm. In an example, an outer sheath polymer can have an average wall thickness in the range from about 0.1 mm to about 2 mm, or in the range from about 0.1 mm to about 1 mm, or in the range from about 0.1 mm to about 0.6 mm.

The therapeutic agent can be provided as dissolved or suspended as solid particles, such as nanoparticles or microparticles, within a hydrogel. The hydrogel can be an osmotic hydrogel that contains an osmotic core component, such as a dissolved or suspended osmolyte that attracts water from the biological environment to form a water-swollen polymer network that promotes the release of the therapeutic agent from the gel. The hydrogel can include a polymer network, a colloidal network, or a combination thereof. The hydrogel can encapsulate the payload (e.g., therapeutic agent) and modulate its release profile by hydrolytic swelling. Hydrogels are highly hydrophilic networks of polymer chains, sometimes found as colloidal gel networks in which water is the dispersion medium. The water-absorbing properties of the hydrogels can result from the presence of hydrophilic functional groups, for example, hydroxy (—OH), carboxylic (—COOH), amidic (—CONH—), primary amidic (—CONH$_2$), and sulfonic (—SO$_3$H), rather than from the osmotic pressure of the hydrogels. In hydrogel swelling, examples of relevant parameters are the swelling rate, swelling ratio, and swelling capacity, which can depend on several physiochemical factors such as the gel size, network porosity, network structure, cross-linking conditions, and cross-linking degree of the hydrogel. While typically not considered in higher molecular weight formulations, the osmolarity of hydrogels can also contribute to swelling or water uptake. The normal osmolarity of the human body is in the range from about 250 to about 350 milliosmoles. Optionally, the osmolarity of the hydrogel can be adjusted to change, for example, the swelling rate.

The technology contemplates combination therapies. A single implant may combine two or more therapeutic agents. Alternatively, single therapeutic agents can be provided separately in implants, with two or more implants implanted, each with different therapeutic agents. A therapy can include implantation of one implant at an initial time, monitoring of conditions, and implantation of another implant, at a later time, in response to conditions. Each therapeutic agent can be provided with additives that, for example, enhance stability, protect the therapeutic cargo in its active form, enhance its residence time in the CNS, adjust pH, adjust osmolarity, enable visualization or tracking of the therapeutic agent (e.g., radioisotopes, nanoparticles), or prevent movement of the therapeutic agent beyond a targeted area. While various combination therapies are envisioned, the technology can provide direct access across the BBB for one or more therapeutic agent.

The technology can use biodegradable polymers that, for example, do not evoke an immune response; do not evoke a sustained inflammatory response; have a degradation time applicable to releasing a therapeutic agent; have appropriate mechanical properties, physical size, or flexibility for their intended use; produce non-toxic degradation products that can be readily resorbed or excreted; and include appropriate permeability and processability for the designed application. Some naturally derived polymers such as collagen, as a sole biological protein, and collagen-derived gelatin alone can show issues, for example, instability, incompatible characteristics, immunogenicity, and poor biodegradability. In contrast, alginate, chitosan, and chitosan blends with, for example, PLA, PLGA, PEG, collagen, or γPGA can be formulated with desirable characteristics. Hydrolytically degradable polymers are materials that possess hydrolytically labile chemical bonds in their backbone and can be broken down without secondary influence. Enzymatically degradable polymers are materials that possess bonds that while can be hydrolytically sensitive, require catalysis to undergo meaningful degradation under physiological conditions. Many of these polymers contain ether or amide bonds which have hydrolytic degradation rates much lower than the polymers discussed above.

The technology can provide a reliable and less invasive strategy for trans-mucosal delivery of therapeutics for permanently bypassing the BBB, by utilizing the therapeutic uptake via olfactory mucosal epithelium. The technology can help to overcome the limitations of traditional topical intranasal dosing modalities owing to the variations of nasal surface and dosing limitations. Using the technology, a mucosal cavity space can be subjected to surgical implantation of polymeric implants encapsulating therapeutics such as drugs, growth factors, oligonucleotides, small molecules, peptides, or CNS disease therapeutics, such that the implants elute the payload continuously for prolonged periods of time, in some cases from weeks to months. The technology can offer a fine modulation and precise control over the release profiles of the payload entrapped with the implant by choosing the right polymer/polymers/copolymer with the required degradation profile and tuning of physical properties such as size, thickness, porosity and packing density of the implant. Implants of the desired dimensions (nano/micro/macro) can be fabricated in a commercial scale by using principles of microfabrication with a range of biodegradable polymers or copolymers, such as that the overall homogeneity with respect to dimensions, uniformity, and surface features can be retained.

The technology can provide several advantages. For example, currently employed clinical procedures for direct CNS administration of therapeutics are mostly invasive by nature, such as intraventricular, intrathecal, or intraparenchymal routes. Although clinically effective, these methods have been associated with device/catheter associated complications which have been classified as infectious and non-infectious issues (e.g., edema, intracerebral hemorrhage, catheter obstruction, subcutaneous CSF leak), and there has been a lack of standardized protocols. The technology described herein can provide a less invasive and more patient-compliant mode of delivering therapeutics to the CNS across the BBB.

Previously reported non-invasive methods of CNS delivery, which can include pharmacological strategies via lipid carriers, physiological methods exploiting intrinsic receptor mediated transport, and BBB permeabilization techniques, need extensive drug manipulation and limit the residence time of the therapeutic. The present technology can protect the therapeutic cargo in its active form and enhance its residence time in the CNS for extended delivery periods.

The technology can employ implants from a wide variety of biodegradable polymers and/or copolymers and can entrap a wide variety of therapeutics such as drugs, small molecules, nucleic acids, peptides, proteins, and prodrugs. The release rate of the therapeutics can be controlled and modulated based on tuning the degradation rate of polymers, which is dependent on choosing a combination of polymers or a single polymer having desirable release profile. The technology of using implants for trans-nasal CNS delivery can provide a delivery platform to combat different aspects of various CNS disorders for a desired period of treatment time, intended for therapy.

Techniques of microfabrication can be employed commercially to make implants of desired dimensions, such that they can be implanted within the mucosal cavity of humans. Miniaturization of implants also offers the feasibility of dose escalation by using a desired number of implants. The thickness, size, and shape of the implants can be designed to tailor release rates. The technology can provide uniformity and homogeneity of size, dimensions, morphology and surface features of implants, which can determine an implant degradation rate, which consequently controls the release rate of entrapped therapeutics.

The technology can be used for providing a sustained-release delivery vehicle for the treatment of brain diseases. The technology can be used for CNS delivery of biologically active molecules for the treatment of Parkinson's, Alzheimer's, and other neurodegenerative diseases. The technology can be used in the treatment of other neuropsychiatric disorders, brain tumors, or newly identified CNS disorders.

Neurodegeneration refers to the progressive atrophy or irreversible damage to the structure and/or function of specific subsets of neurons of brain and spinal cord which ultimately results in their death (Andreone, et al., 2020; Farooqui, 2018; Marilù Giacalone, et al., 2015). This leads to a large group of debilitating disorders manifesting heterogenous pathological characteristics that affect approximately 30 million people worldwide, while the treatment options still remain scarce (Sheikh, et al., 2013; Przedborski, et al., 2003; Duggan, et al., 2020). Aging is the primary risk factor for the escalating burden of such disorders, such as Alzheimer's disease or Parkinson's disease (Duggan, et al., 2020; Tanner & Goldman, 1996). Apart from being ineffective, the currently available drugs used for alleviating disease symptoms exert toxic side effects (Przedborski, et al., 2003; Duggan, et al., 2020).

Brain derived neurotrophic factor (BDNF) is a neurotrophin important for the survival, differentiation and maturation of neurons of the nervous system (Huang & Reichardt, 2001; Padmakumar, et al., 2020). BDNF protein and mRNA levels have been detected in the majority of adult brain sub-regions such as olfactory bulb, cortex, hippocampus, basal forebrain, hypothalamus, mesencephalon and brainstem (Bathina & Das, 2015; Miranda, et al., 2019). Reduced expression of BDNF in the nigrostriatal dopaminergic brain regions has been implicated in the pathogenesis of Parkinson's disease (Parain, et al., 1999; Palasz, et al., 2020; Mogi, et al., 1999; Murer, et al., 2001). Additionally, insufficient supply of neuronal BDNF leads to defects in synaptic plasticity, thereby leading to neurodegeneration (Palasz, et al., 2020). Therefore, there is a clear need for the development of therapeutic interventions aimed at increasing BDNF levels for neuroprotective as well as neurorestorative treatment arms (Zigova, et al., 1998; Modarresi, et al., 2012). On the other hand, there are several challenges that hinder the development and engineering of recombinant BDNF protein therapies: a complex synthetic process, the existence of multiple active BDNF isoforms binding to different receptors, the highly intricate structure of the BDNF gene, and the regulation of its expression at multiple levels (Kowiański, et al., 2018; Mitchelmore & Gede, 2014; Mercado, et al., 2018; Cattaneo, et al., 2016; Martínez-Levy & Cruz-Fuentes, 2014). Compounding these issues are the physico-chemical properties of neurotrophins that do not allow them to cross the BBB and further complicate CNS delivery (Khorkova & Wahlestedt, 2017).

Oligonucleotides are useful for neurodegenerative disease therapy owing to high target specificity and accessibility, wide CNS distribution, and negligible toxicity concerns (Khorkova & Wahlestedt, 2017; Smith, et al., 2017). In contrast to some recombinant proteins, oligonucleotides have a more straightforward path to clinical translation and large-scale commercial development, partly due to more defined constituent chemistry and precise synthetic processes. BDNF AntagoNATs are single stranded short synthetic oligonucleotide-based compounds possessing the ability to inhibit BDNF-AS, the conserved noncoding natural antisense transcript (NAT) which normally slows down BDNF sense RNA transcription and represses endogenous BDNF protein production. It has been previously reported that BDNF AntagoNAT (BDNF AT) treatment can induce BDNF mRNA and protein upregulation and in vitro differentiation and in vivo proliferation of neuronal cells (Modarresi, et al., 2012). Nevertheless, the BBB-impermeant nature of such ATs typically requires invasive modes of CNS delivery such as intrathecal (IT) or intracerebroventricular (ICV) routes wherein the BBB is physically breached (Khorkova & Wahlestedt, 2017). Such routes are associated with significant potential adverse effects such as brain edema, hemorrhage, seizures, cerebrospinal fluid (CSF) leak, catheter related complications, infections, and in rare cases death (Cohen-Pfeffer, et al., 2017; Slavc, et al., 2018).

Intranasal administration, one potential alternative to direct CNS administration, has been reported to bypass the BBB in a non-invasive manner and deliver therapeutics including both small and macromolecules to the brain within a short period of time (Hanson & Frey, 2008). However, it has not been successfully clinically adopted owing to the pitfalls associated with uniformity of delivered dose, poor drug distribution, limited mucosal retention, and restricted trans-epithelial diffusion (Padmakumar, et al., 2021). In this context, the present technology exploits the direct trans-nasal, trans-olfactory pathway to CNS through the direct submucosal implantation of a therapeutic depot. This Minimally Invasive Nasal Depot (MIND) technique can be based on a routine endoscopic guided intranasal procedure performed by otorhinolaryngologists and provides a direct route of access to the basolateral aspect of the olfactory epithelium (OE) thereby enabling direct CNS delivery. A previously reported rat model of MIND could recapitulate the anatomy of the proposed clinical depot delivery technique (Padmakumar, et al., 2021). The procedure is found to be well tolerated by animals while eliminating the need for invasive BBB penetrating techniques such as ICV administration. The administration of BDNF AT formulations (AT dispersed in thermosensitive Pluronic F-127 gel and AT liposomes-in gel suspension) to the submucosal compartment of rat OE by the MIND technique can provide efficient and consistent dose delivery within the tissue surrounding the olfactory neurons. MIND administration also provides high CNS uptake of the otherwise BBB impermeant BDNF AT with a relative delivery efficiency approaching 40% of the direct ICV route. It is demonstrated that a single intranasal dose significantly increased BDNF proteins levels in different subregions of brain up to 4 days post administration, confirming the therapeutic translational potential of this method (Padmakumar, et al., 2021). Significantly, the technology herein provides implantable formulations from biodegradable polymers to further extend the release profile of therapeutics. While BDNF AT is used as an example, the technology can be applied to a large variety of therapeutics to address the needs of patients as the availability of therapeutics grows.

In an example, the concept of custom-made core-shell implants can be utilized with a unique design of an "osmotically-active core" and a "biodegradable shell" with tailorable dimensions, shapes and properties specifically amenable for MIND implantation. Unlike other biodegradable polymer implants, an osmotic core-shell implant design is highly versatile from an engineering perspective, can accommodate a variety of payloads and can be custom-designed for different therapeutic indications.

The pharmacokinetic and pharmacodynamic advantages of sustained BDNF AT delivery and the in vivo safety profile of the 'MIND Implant' approach in healthy animals are discussed in detail herein. Fabrication of an osmotic core-shell implant specific for BDNF AT delivery using MIND is demonstrated. Polymeric implants having a unique core-shell architecture are candidates for prolonged delivery of different kinds of therapeutics to the CNS using the MIND technique. The advantages of the MIND technique for trans-nasal drug delivery directly to the brain via the basolateral aspect of olfactory epithelium are established (Padmakumar, et al., 2021). The biodegradable and biocompatible implants demonstrated herein can sustain-release an entrapped therapeutic payload for increased duration, ultimately yielding enhanced CNS uptake and efficacy, as a complimentary technology to MIND, for CNS delivery of drugs for treatment of various neurodegenerative diseases.

In order to guide the design strategy for implants, the approximate dimensions of the rat nasal cavity containing the submucosal space formed by the MIND technique are shown to be 1.186±0.08 cm length by 1.131±0.09 cm breadth in FIG. 14. A core-shell design can be ideal because (1) an osmotic core component encapsulates the payload (e.g., small molecule, biologic, oligonucleotide) and modulates its release profile by hydrolytic swelling and (2) a polymeric sheath around the core acts as a barrier layer to delay and further control the drug release profile. Poloxamers or Pluronics are non-toxic and FDA approved amphiphilic high molecular weight polyethylene oxide-polypropylene oxide-polyethylene oxide (PEO-PPO-PEO) triblock copolymers including hydrophilic PEO segments and hydrophobic PPO sections (Lv, et al., 2007; Falath, et al., 2016). Pluronic F-127-based hydrogels have properties of good water retention, reverse thermal gelation and can also provide controlled release of biomolecules/drugs incorporated within their hydrophilic networks making them good candidates as injectables for drug delivery (Tan & Marra, 2010; Gioffredi, et al., 2016; Gilbert, et al., 1986; Guzmán, et al., 1992). Several studies highlight the ability of poloxamer-based osmotic membranes to modulate the penetration rate and permeation flux of the corresponding coagulation medium (mostly water) (Lv, et al., 2007; Iwasaki, 2003; Ishihara, et al., 1995). Considering these properties, Pluronic F-127 can be utilized as a core component entrapping BDNF AT, as it can simultaneously behave as an osmotic hydrogel core (i.e., a hydrogel that swells in a physiological fluid), enhancing the water permeation rate, leading to hydrolytic swelling and thereby controlling the rate of AT release. This osmotic effect can be regulated with the amount of Pluronic F-127 entrapped in a designed implant. PCL, an aliphatic polyester, is an FDA approved biodegradable, biocompatible polymer extensively investigated in the fields of controlled drug delivery and regenerative medicine with a history of human use (Woodruff & Hutmacher, 2010; Manoukian, et al., 2019). Here, PCL is utilized as an example component for fabricating an outer sheath entrapping a Pluronic F-127 core, owing to its hydrophobicity and slower degradation profile using a simple dip-coating technique. The shell can be modular in its biodegradation profile and diffusional kinetics-based release which in turn, is based on the molecular weight of PCL (or other polymers) and the sheath thickness. Herein, an example of an engineered PCL shell can be designed specifically for diffusional release of the payload (not by degradation) based on the time scale of the overall study.

Figure 11:
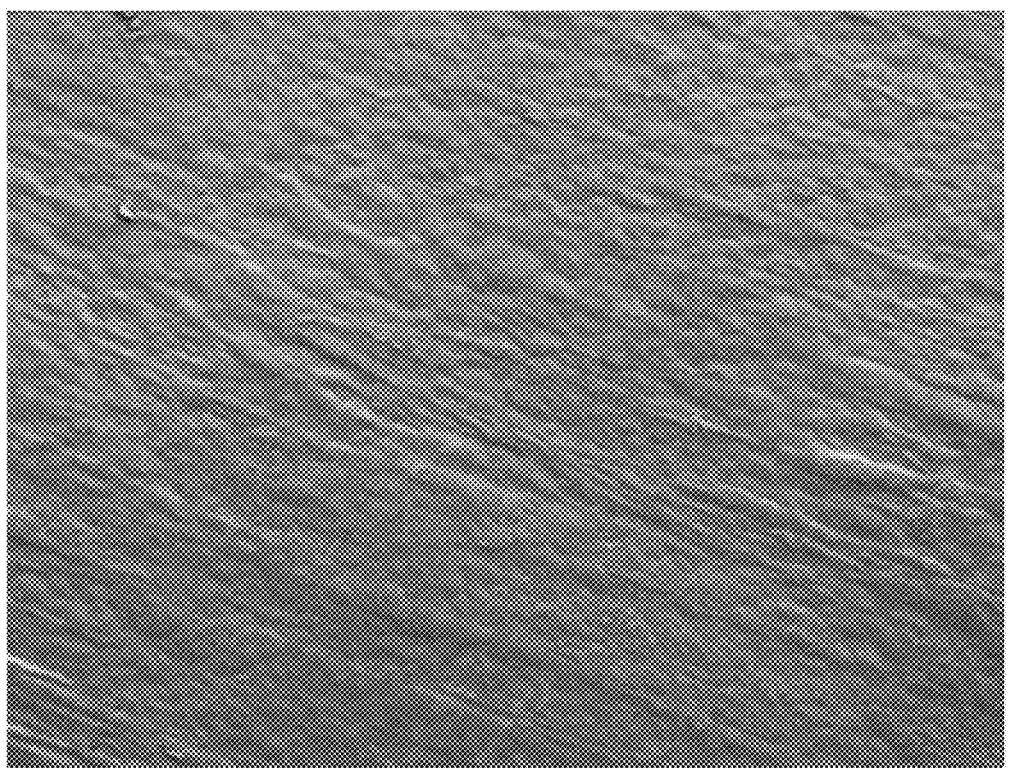
FIG. 11 shows surface morphology of a dip-coated PCL shell assessed by low magnification FESEM.
Figure 12:
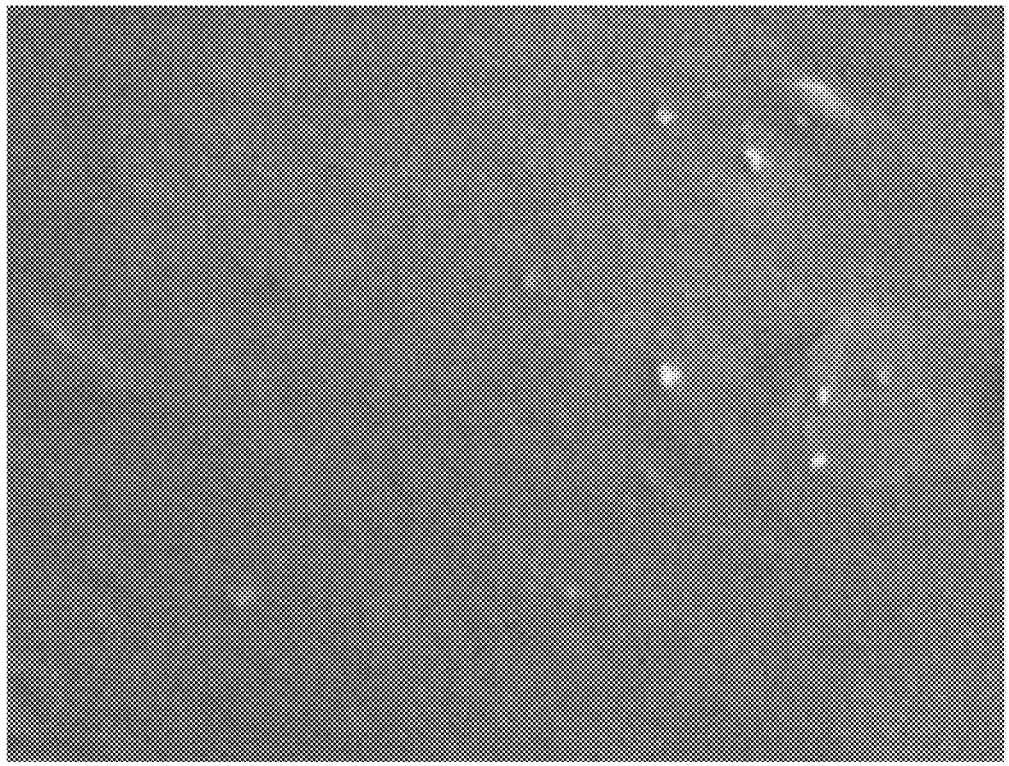
FIG. 12 shows surface morphology of a dip-coated PCL shell assessed by high magnification FESEM.

As shown at the left of FIG. 10, an optimized PCL solution concentration of 14% w/v and 9-10 dipping cycles of a glass rod can form a shell with an average thickness of about 0.54±0.05 mm and a diameter of approximately 5 mm. At the center of FIG. 10A, concentrated Pluronic F-127 gel with a BDNF AT payload can be added to this hollow PCL shell, and the open end of the reservoir can be subsequently sealed. The strategy offers flexibility with regard to several parameters such as selection of biodegradable polymers or copolymers with different degradation time frames, enabling incorporation of a variety of payloads with high loading and control of their release profiles. Processing parameters such as concentration of the polymeric solution, choice of the coating substrate and control of optimum dipping cycles aid in the modulation of dimensions and tailorability of shapes of the implants (e.g., FIG. 10B). For example, cylindrical PCL shells of different dimensions (about 5 mm and about 2 mm inner diameters) can be fabricated using glass rods as coating substrates with the corresponding diameters. A qualitative assessment of the surface of PCL coated shell with FESEM reveals a uniform homogenous morphology and texture as shown in FIG. 11 and FIG. 12.

Figure 13:
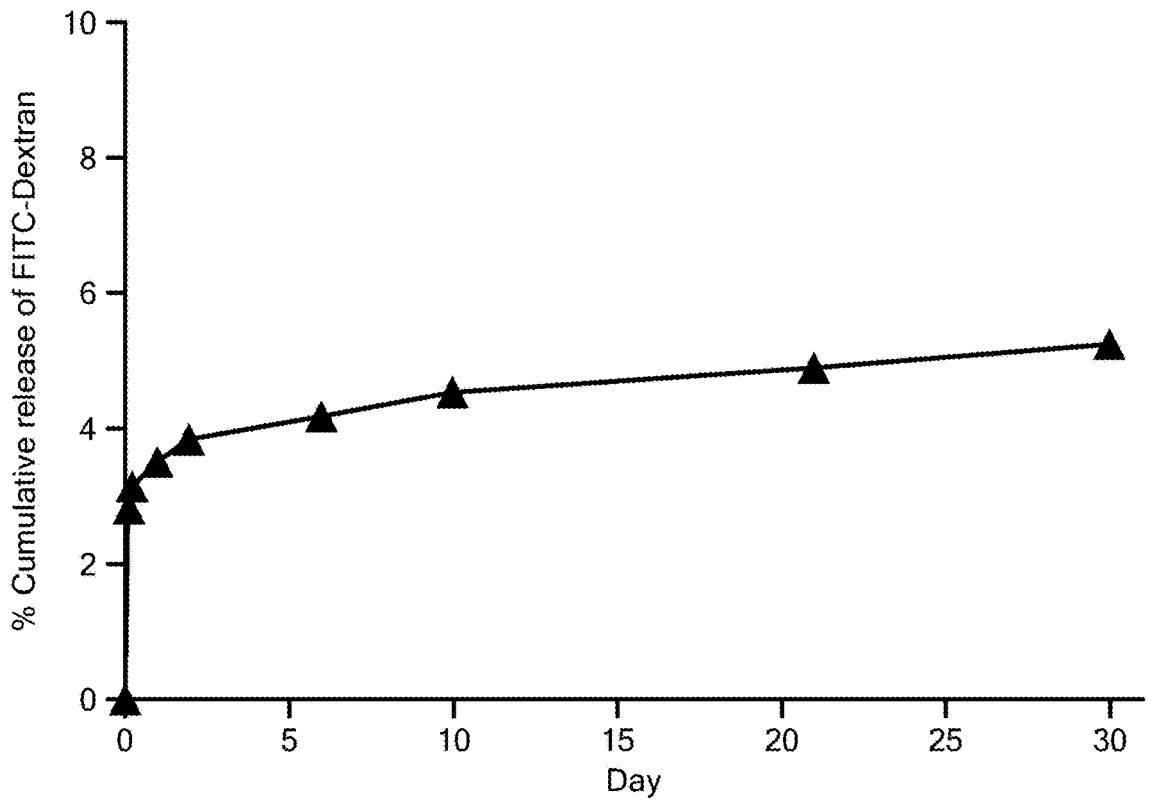
FIG. 13 shows a plot of in vitro cumulative release of FITC-dextran (fluorescent) dye (expressed as percent of the total payload) from an implant depicted at the right of FIG. 10A into PBS (37° C., pH 7.4, 100 rpm).

In FIG. 13, an initial in vitro release experiment conducted with implants entrapping the hydrophilic fluorescent dye, FITC-Dextran, demonstrates a biphasic slow-release profile, wherein ~3.8% of the payload is released within a day and ~6% within a period of 30 days. It is envisioned that such a release pattern can ideally mimic the clinical administration of an initial 'loading' bolus dose of a therapeutic payload in the beginning of a proposed treatment period in patients, followed by a trend of slower release for 'maintanence therapy' (Amjad, et al., 2019). Hence, the engineering of core-shell implants is shown as an example of a simple yet versatile approach offering flexible control over implant dimensions as well as an optimal drug release profile; which are two important characteristics for MIND implants.

Figure 24A:
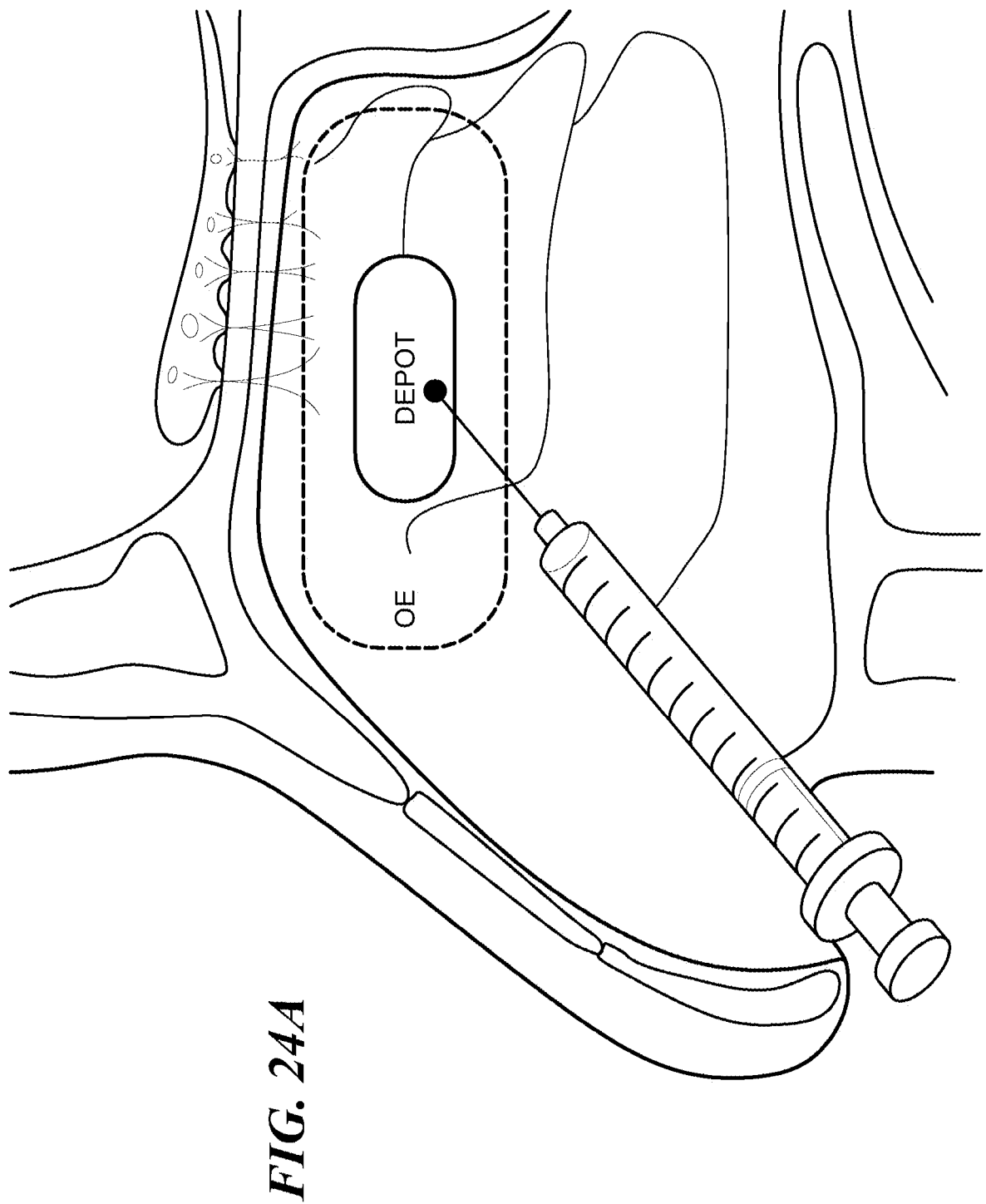
FIG. 24A shows an illustration of placement of a minimally invasive depot injection in a human nose within the submucosal space of the olfactory epithelium (OE, dotted line, adapted from Servier Medical Art).
Figure 24B:
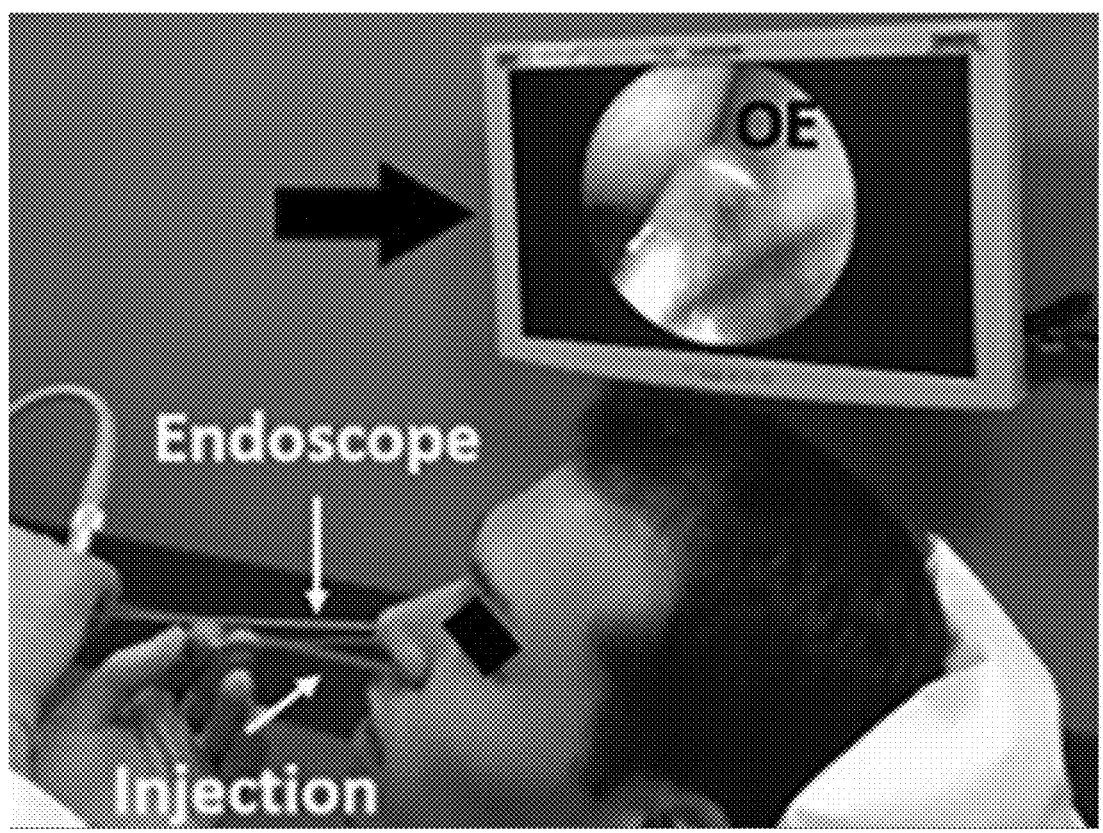
FIG. 24B shows performance of an intranasal procedure in an awake patient during an outpatient visit to the Otolaryngology (ENT) clinic, guided by a high-definition nasal endoscope with the image projected onto a real time high-definition monitor indicated by black arrow (OE labelled on screen as seen during an endoscopic exam).
Figure 24C:
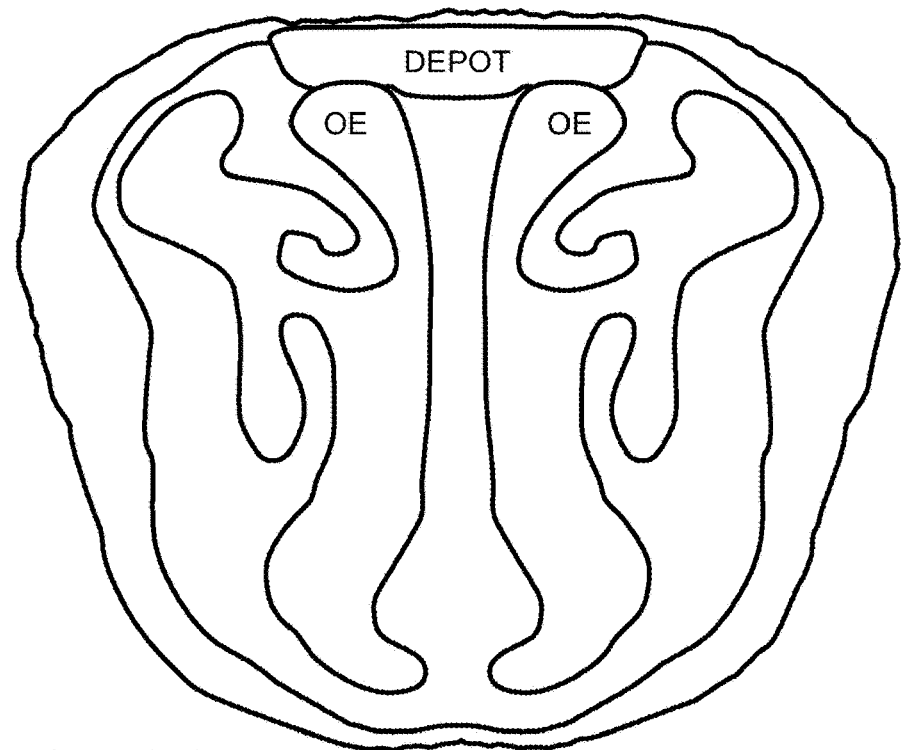
FIG. 24C shows a cross-sectional illustration of rat snout demonstrating location of the depot in contact with the basolateral aspect of the olfactory epithelium (OE).

For in vivo administration of BDNF AT core-shell implants using MIND, core-shell implants entrapping BDNF AT as payload are implanted within the submucosal space of healthy Sprague Dawley rats using the MIND technique as illustrated in FIGS. 15A-15D. The clinical MIND procedure in humans can require a simple endoscopy guided trans-nasal injection of drug within the olfactory sub-epithelium in awake, topically anesthetized patients (FIG. 24B). In adult humans, the olfactory epithelium typically measures about 9 cm² (about 3 cm by about 3 cm in size) and lies on the roof of the nasal cavity about 7 cm above and behind the nostrils. Placement of an implant or depot within the olfactory sub-epithelium is illustrated in the example of FIG. 24A. In contrast, the rat snout is too small to access this space trans-nasally, thereby necessitating an open surgical approach (Padmakumar, et al., 2021).

Figure 15A:
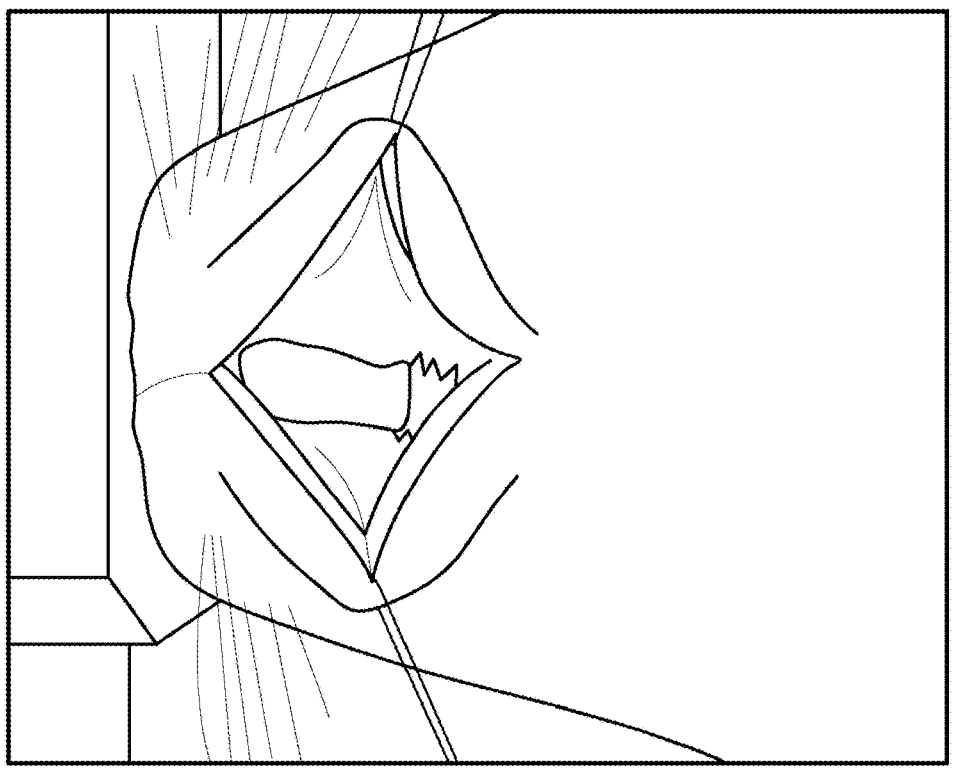
Figure 15D:
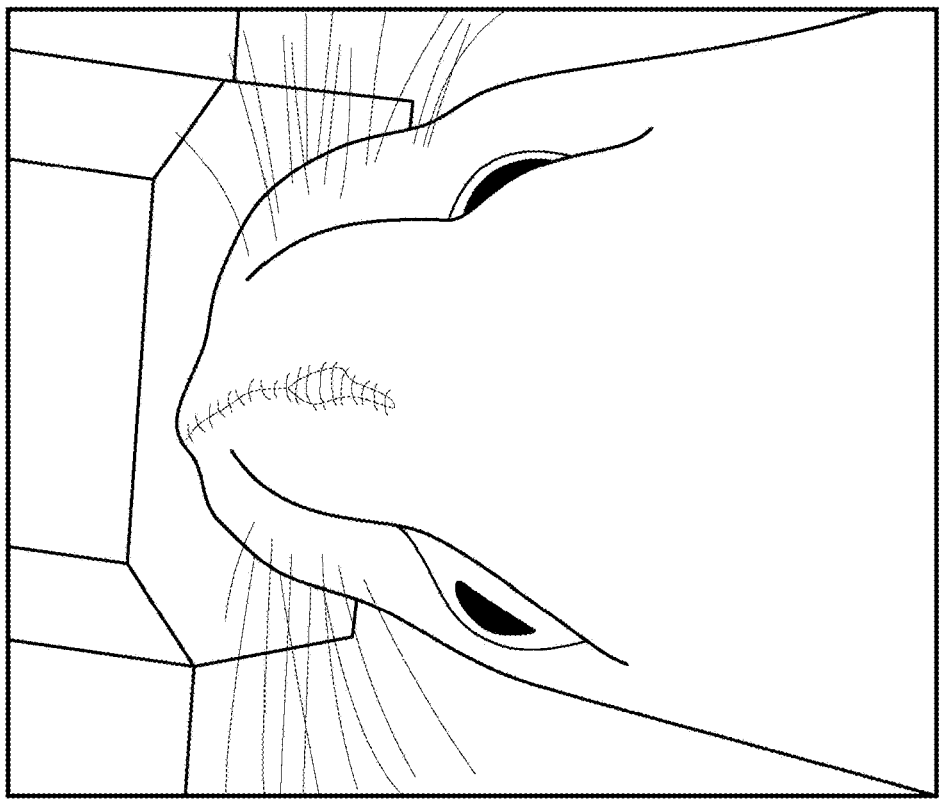
Figure 15C:
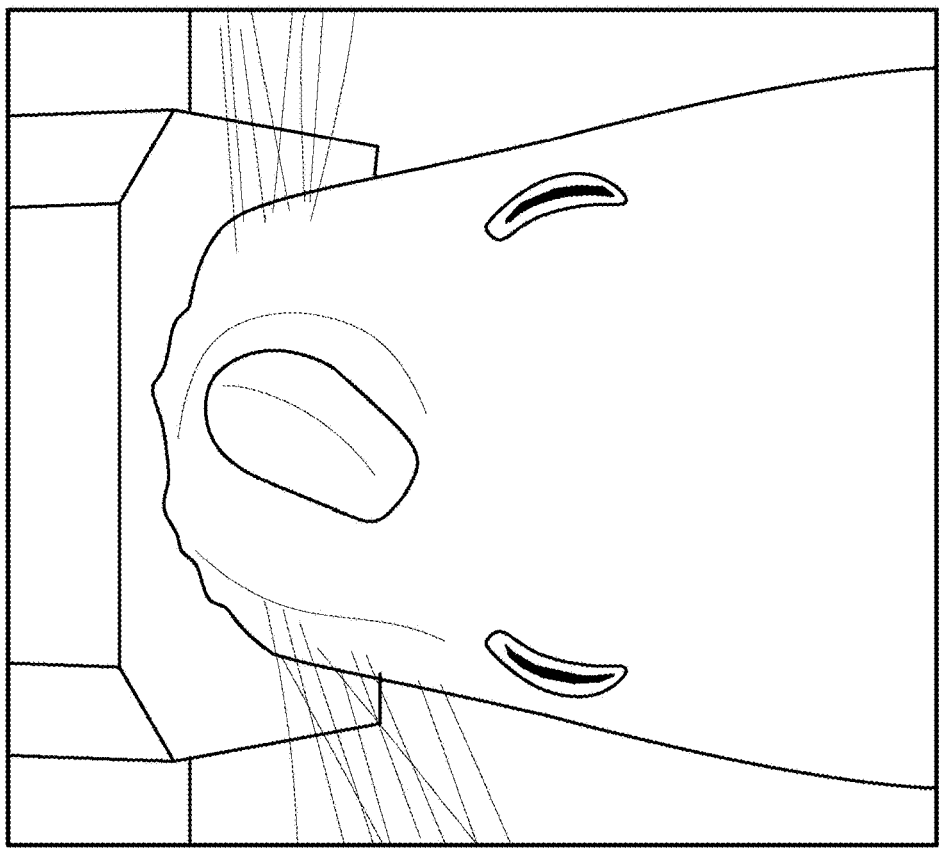
Figure 22:
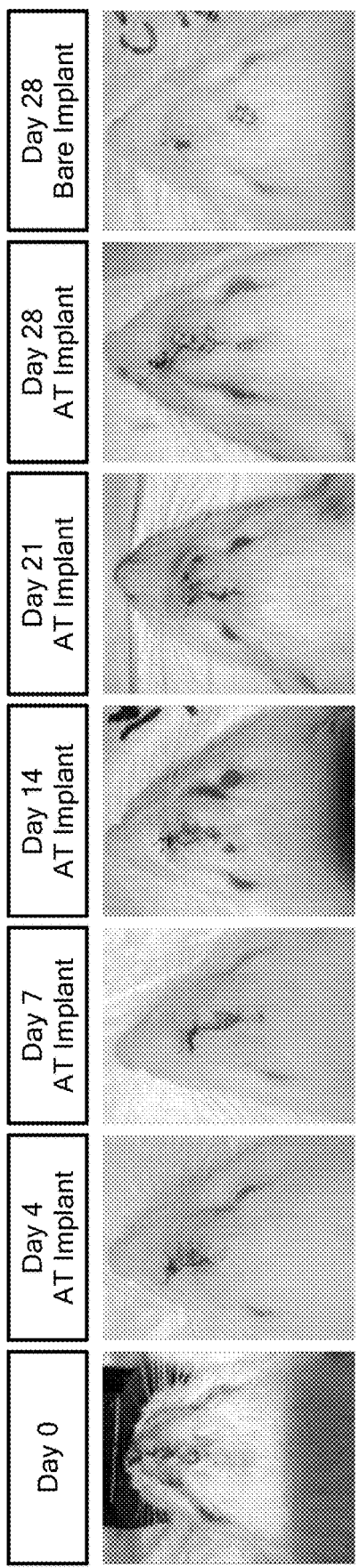
FIG. 22 shows images of visual inspection of snouts of rats subjected to MIND implantation surgery post euthanasia at different time points.

As shown in FIG. 15A, a sagittal midline skin incision simultaneously exposes the rat nasal bones while creating the subcutaneous pocket to accept the implant. Careful drilling of a segment of the nasal bones exposes the intact olfactory submucosa (FIG. 15B) onto which the core shell implant can be placed (FIG. 15C). The implant dimensions are designed to conform to this cavity without compressing the surrounding structures (e.g., FIG. 14, FIG. 15C). Primary closure of the surgical incision by continuous suturing (FIG. 15D) facilitates rapid wound closure without signs of infection or dehiscence over time as is illustrated in FIG. 22. The MIND implantation procedure is easily reproducible, and all experimental rats remained healthy throughout the study period of 4 weeks, without any signs of illness or lethargy.

Figure 16A:
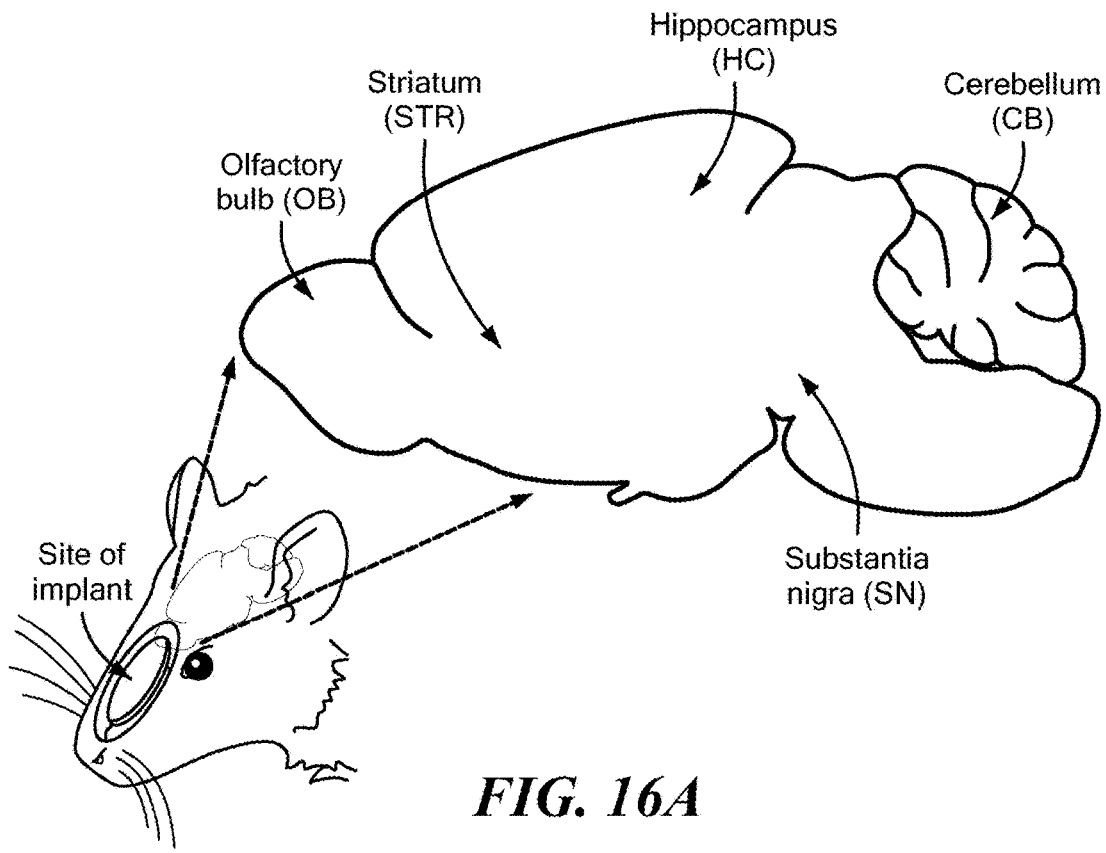
FIGS. 16A-16F show BDNF AntagoNAT (AT) levels in rat brain sub-regions at different time points post-MIND implantation.
Figure 16B:
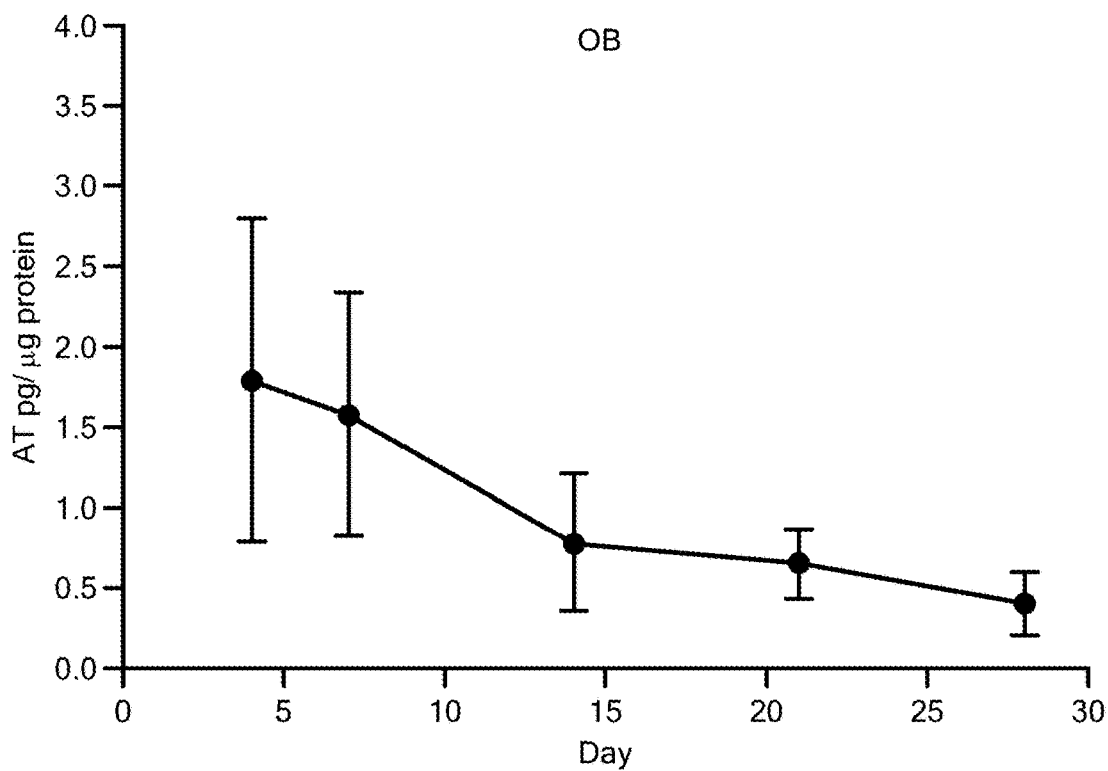

To study CNS delivery of BDNF AT via MIND implantation and pharmacokinetic analysis, an in vivo study is conducted over a time span of 4 weeks with example time points of 4, 7, 14, 21, and 28 days post implantation to assess the long term BDNF AT delivery potential of MIND implants. Animals are euthanized at each time point, and AT levels in different subregions of brain are quantified to analyse the CNS uptake and brain distribution of BDNF ATs. In this example, different subregions of the brain are located as illustrated in FIG. 16A. FIG. 16A shows the location of an implant with various sub-regions of interest in rat brain. The sustained AT distribution over different sub regions of brain over 28 days is plotted in FIGS. 16B-16F. In FIGS. 16B-16F, the BDNF AT levels in these tissues at different time points such as 4, 7, 14, 21 and 28 days, are quantified by BDNF AT hybridisation assay (n=4 rats/time point, AT levels represented as mean±SEM).

Figure 16C:
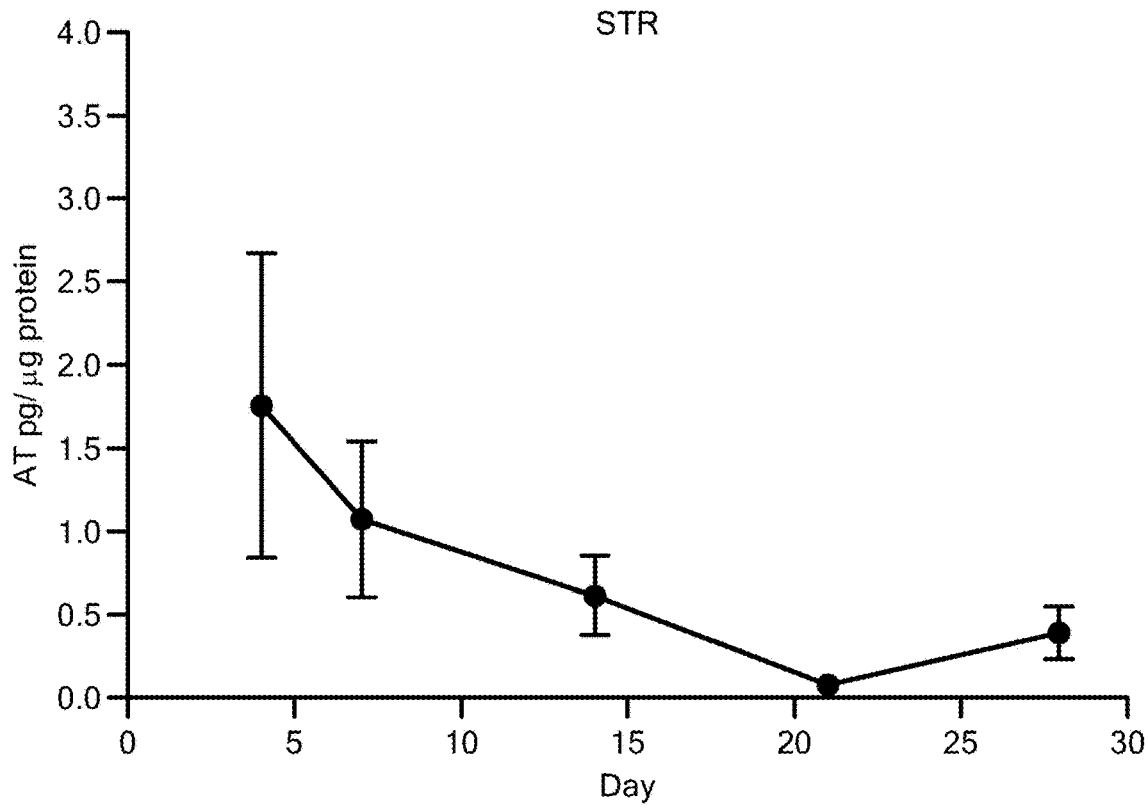
Figure 16D:
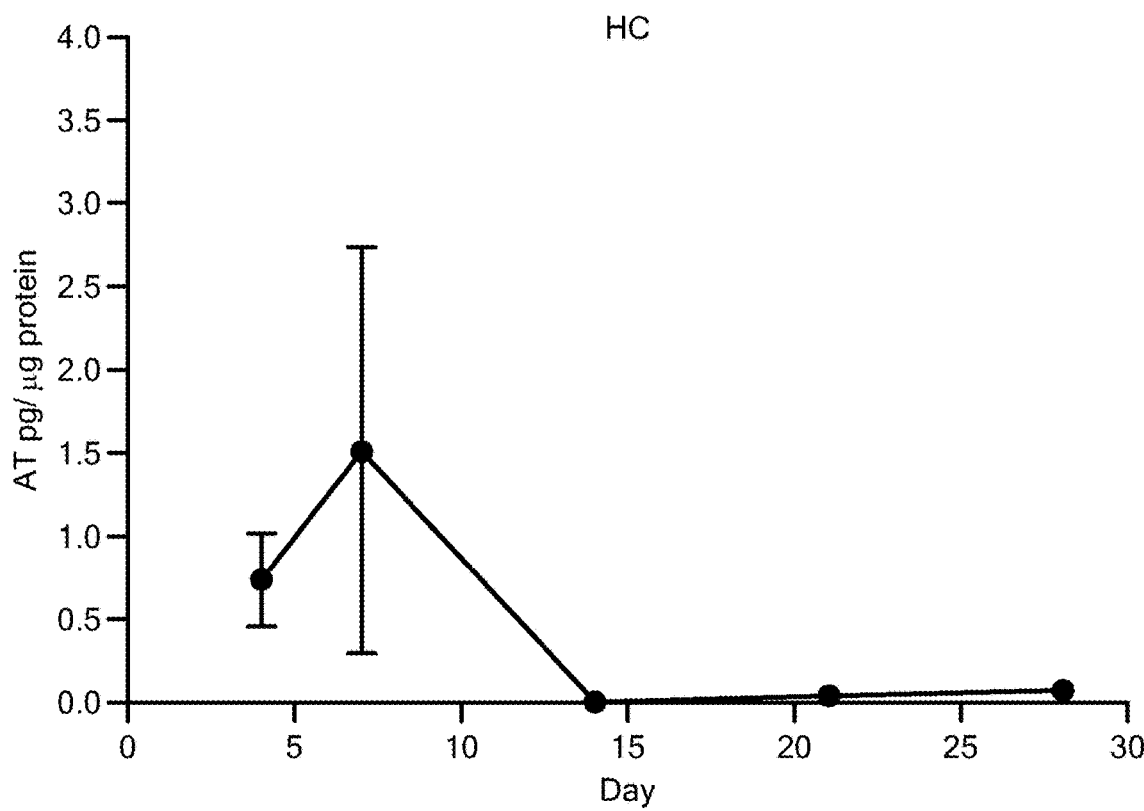
Figure 16E:
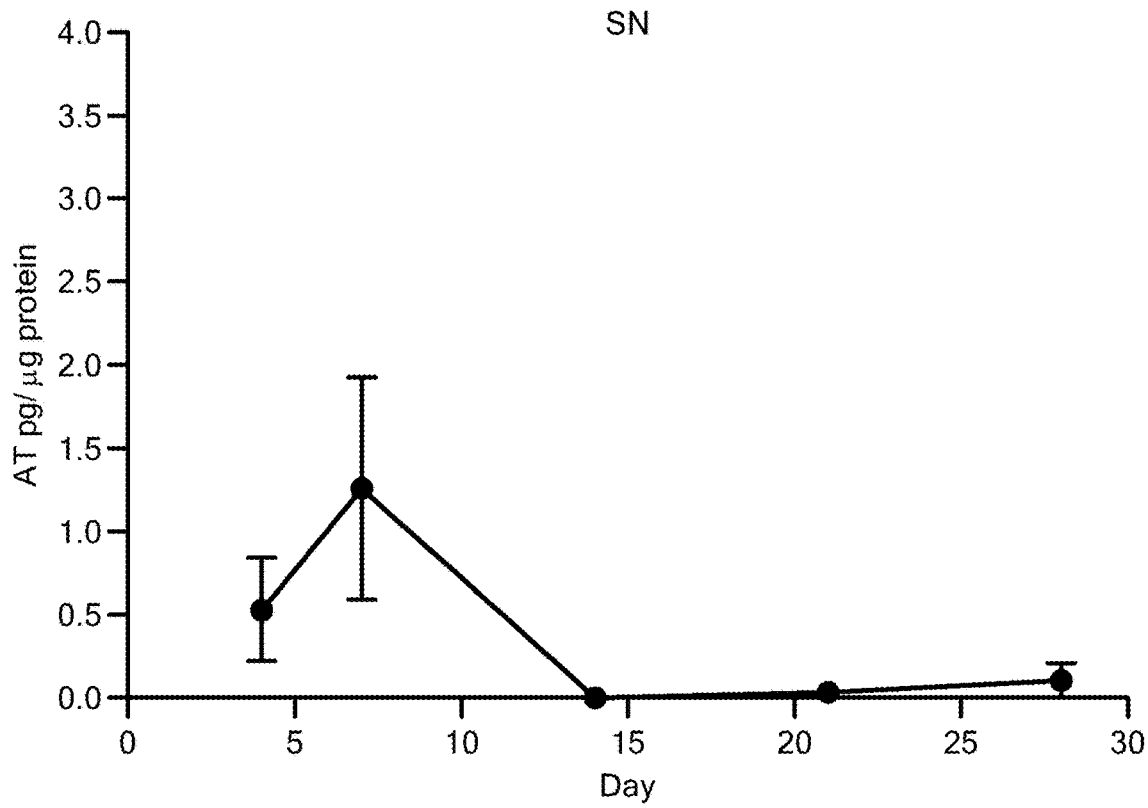
Figure 16F:
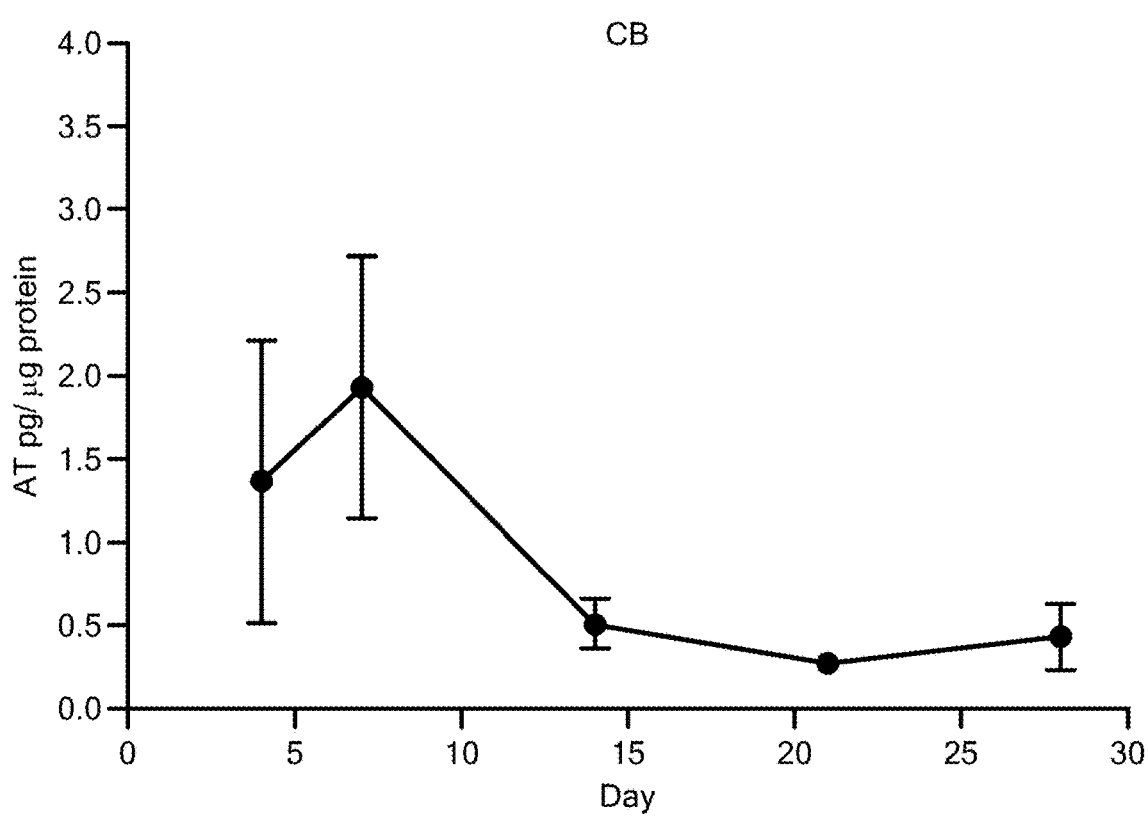

The observed trends in mean AT concentration over time indicate a tissue-specific AT distribution pattern, which is in line with observations for the CNS distribution of AT (Padmakumar, et al., 2021). For OB (olfactory bulb) shown in FIG. 16B, the highest mean AT concentrations are detected on day 4 (~1.8 pg/µg), which is then followed by a slow and steady decline in the AT levels over time. It is observed that the BDNF AT levels persist in the OB at detectable concentrations for the duration of the study. In FIG. 16C, a similar trend is also noted for the striatum (STR), wherein the mean AT levels decrease over time. However, the hippocampus (HC, FIG. 16D) and substantia nigra (SN, FIG. 16E) display a different trend, wherein high mean AT levels are observed on day 7 (1.25-1.5 pg/µg) which is then followed by a steep decline to negligible AT amounts. Although the cerebellum (CB, FIG. 16F) displays a similar trend in AT concentration to the HC and SN, the overall concentration is higher, and therefore appreciable AT levels are detectable at later timepoints. These data suggest that the midbrain and hindbrain sub-regions display comparable trends of AT distribution with a slower rise in mean AT levels and a subsequent decrease towards 2-4 weeks.

Furthermore, no AT is detected in plasma samples of all the animals subjected to the MIND implantation disclosed herein, which confirms the observation that MIND mediated CNS uptake occurs directly through the olfactory epithelium and not by a secondary peripheral distribution (Padmakumar, et al., 2021; Harkema, et al., 2006; Gänger & Schindowski, 2018).

The time course of BDNF AT tissue concentrations are further characterized using NCA (noncompartmental analysis) to evaluate pharmacokinetic parameters of the implant formulation, and these data are summarized in Table 4. These data also suggest tissue-specific distribution of AT within the CNS. The extent of distribution, as determined by AUC values, varies from 115-369 pg*mL$^{-1}$*day, with the least distribution in the HC and SN, and the most AT distributed to the OB (Table 4). Similar trends are observed for $C_{max}$, with a range of 13.4-19.4 pg*mL$^{-1}$ for deep brain tissues and 27.8 pg*mL$^{-1}$ for the OB. Interestingly, MRT values, which range from 7.27-10.8 days, are more uniform for all brain sub-regions, which indicates that on average, AT molecules stay in the brain for more than a week and are cleared from tissue sub-regions at similar rates. Collectively, these pharmacokinetic parameters suggest that the OB, which is the tissue closest to the implant site and also the first point of contact in the trans-olfactory route (Shantha, 2017), behaves distinctly from deeper brain tissues. In this example, the rate of AT diffusion partly enhanced by the swelling and osmotic action of Pluronic F127 gel core can also lead to high AT distribution into OB.

Figure 17A:
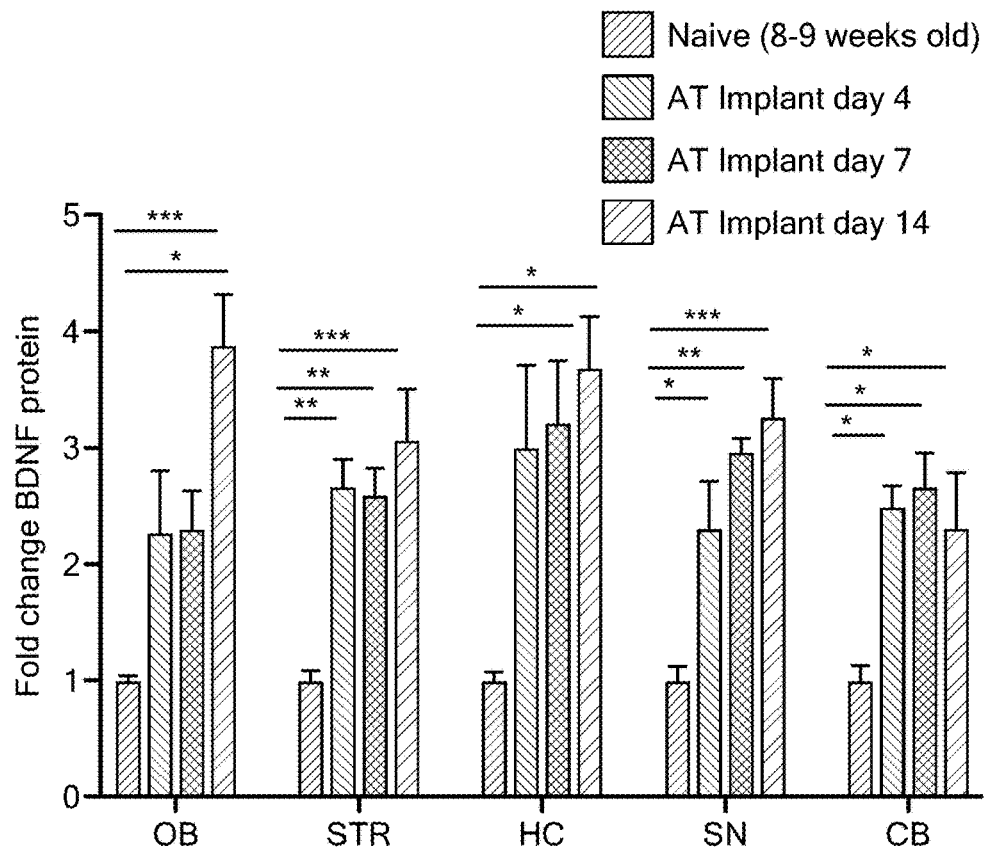
FIGS. 17A-17C shows BDNF protein levels in rat brain sub-regions at different time points post-MIND implantation. BDNF protein levels in brain sub-regions of rats administered via MIND implants at different time points such as (17A) 4, 7 and 14 days; (17B) 21 days and (17C) 28 days relative to protein levels of naïve animals of comparative ages, measured by BDNF ELISA (n=4 rats/group, fold change values represented as mean±SEM, *p<0.05, p<0.01, *p<0.001, One-way ANOVA with Tukey post-hoc test for multiple comparisons for (17A), student's t-test for 17B and 17C).
Figure 17A:
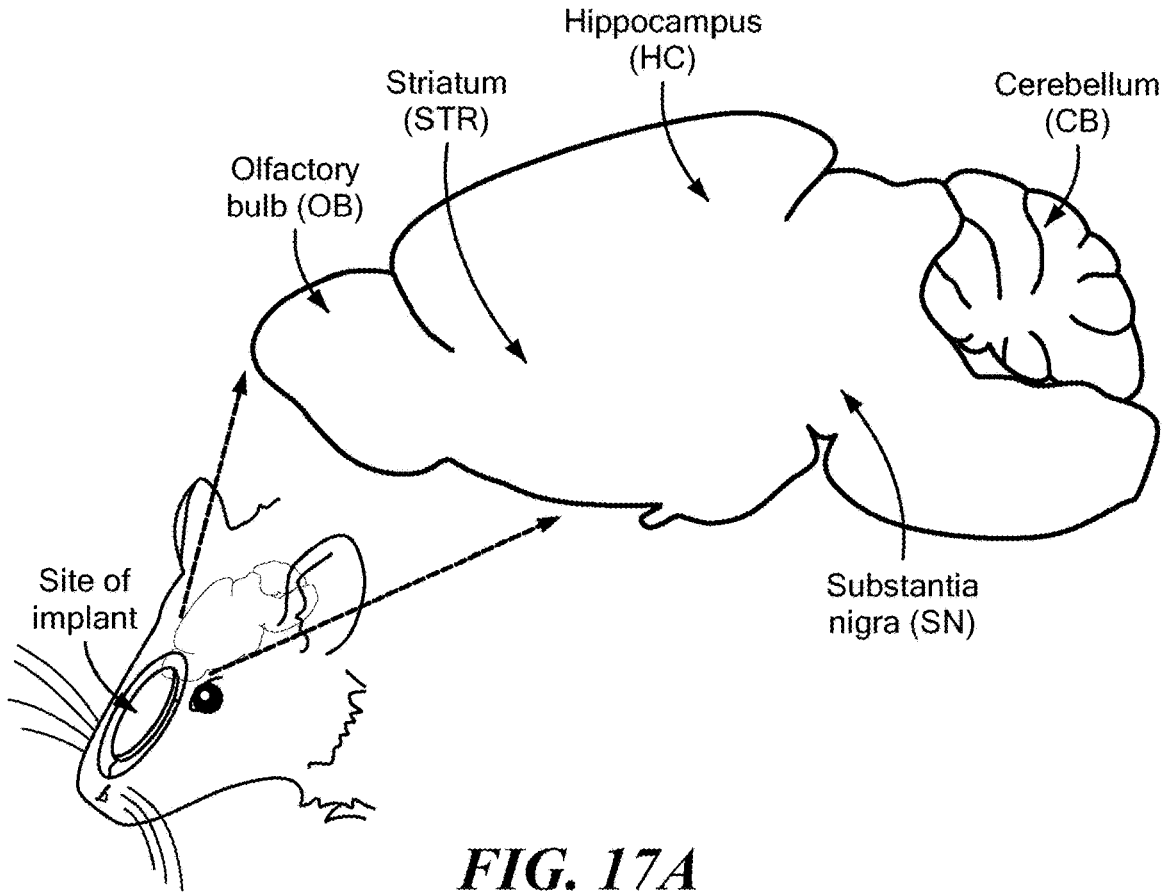
Figure 17B:
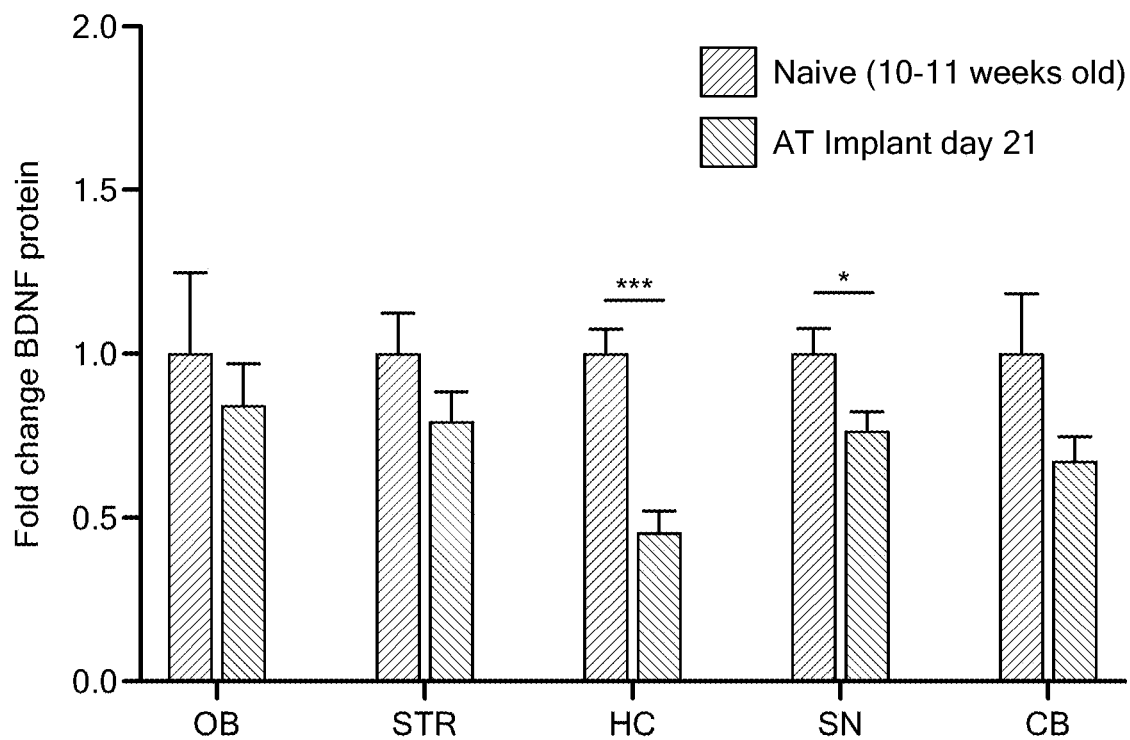
Figure 17C:
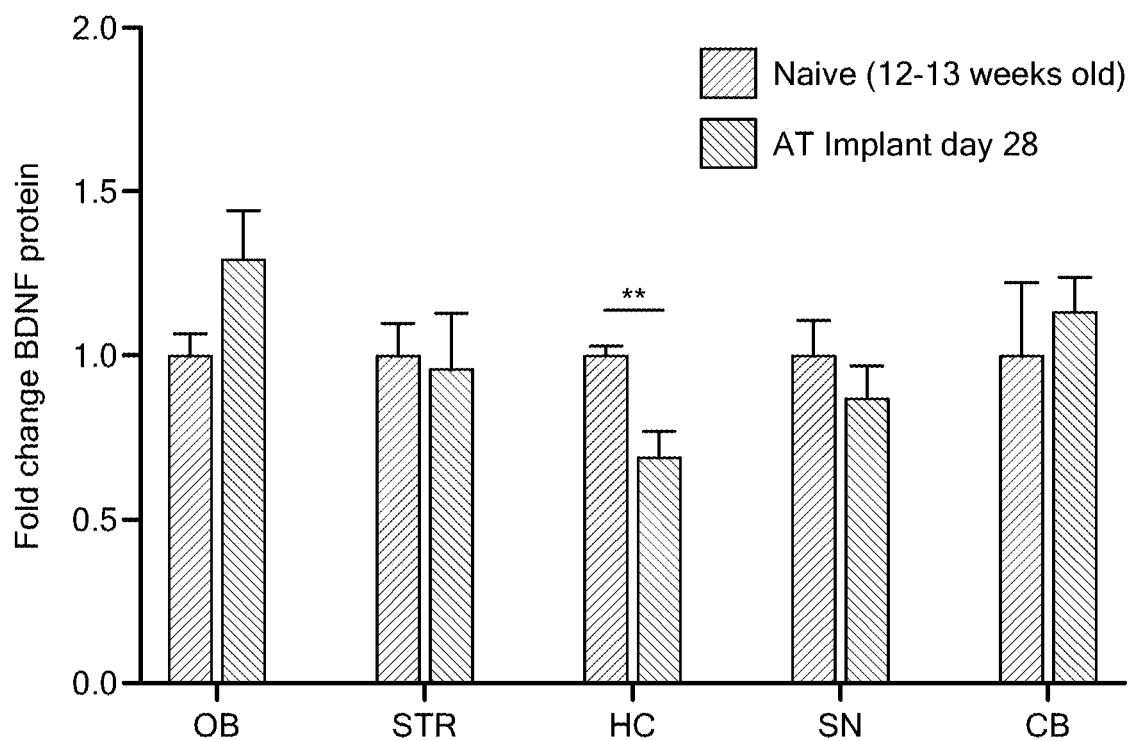

Overall the PK studies confirm that MIND implants can elute BDNF AT for prolonged durations, thereby successfully delivering the otherwise BBB-impermeant AT to deep brain sub regions and sustaining its concentrations for extended time periods.

increment in BDNF expression is observed at days 4 and 7 in OB relative to naïve BDNF levels. By day 14, BDNF levels in the OB are 4-fold higher than naïve animals, which is a statistically significant difference. Similarly, the STR, SN, and HC all demonstrate statistically significant increases in BDNF levels at 4, 7, and 14 days. There are tissue-specific BDNF level increases of 2.5-3.5 fold in STR and SN and 3-4 fold increases in the HC. The BDNF expression at day 14 is the highest in all of these tissues, compared to the levels attained at days 4 and 7. The CB is the only region wherein a slightly different trend is noted, with a plateau in BDNF levels from days 4-14. Upregulation of BDNF levels at day 21 is not noticed (FIG. 17B) or day 28 (FIG. 17C), relative to the corresponding naïve levels. This observation can be correlated to the extended period of very low BDNF AT levels noted in the majority of the brain sub-regions at these time points. Additionally, it can also be attributed to the reported fluctuations in BDNF levels in the course of rat brain development and aging. The BDNF protein levels in rat brain sub-regions at different time points post-MIND implantation are illustrated in FIGS. 17A-17C. BDNF protein levels in brain sub-regions of rats administered via MIND implants at different time points such as (FIG. 17A) 4, 7 and 14 days; (FIG. 17B) 21 days and (FIG.

TABLE 4

Pharmacokinetic parameters of BDNF AT following BDNF AT implant administration via MIND technique.

| Parameter | Unit | OB | STR | HC | SN | CB |
|---|---|---|---|---|---|---|
| $t_{max}$ | day | 4 | 4 | 7 | 7 | 7 |
| $C_{max}$ | pg*mL$^{-1}$ | 27.8 | 18.7 | 13.4 | 16.6 | 19.4 |
| AUC† | pg*mL$^{-1}$*day | 369 | 206 | 115 | 119 | 245 |
| AUMC† | pg*mL$^{-1}$*day$^2$ | 3.95E+03 | 2.14E+03 | 8.34E+02 | 8.85E+02 | 2.63E+03 |
| MRT† | day | 10.7 | 10.4 | 7.27 | 7.43 | 10.8 |

†Estimated from time zero to last time point

Having analyzed the PK profiles and CNS distribution of BDNF AT delivery by MIND implants, next are studied its biological effects by quantifying the BDNF protein levels in brain subregions as illustrated in FIGS. 17A-17C and assessing the response kinetics as summarized in Table 5. Previous studies have established the age-dependent significant variations in BDNF distribution and expression levels in different regions of rat brain (Silhol, et al., 2005; Katoh-Semba & Takeuchi, 1997; Coria-Lucero, et al., 2016). Therefore, it is crucial to consider aging of MIND implanted rats within the treatment frame of 28 days as a study parameter. Thus, naïve rats of appropriate ages and matched sexes were used as negative controls for this study (FIGS. 17A-17C).

TABLE 5

Pharmacokinetic parameters of BDNF response following BDNF AT implant administration via MIND technique

| Parameter | Unit | OB | STR | HC | SN | CB |
|---|---|---|---|---|---|---|
| $t_{max}$ | day | 14 | 14 | 14 | 14 | 7 |
| $C_{max}$ | pg*µg protein$^{-1}$ | 1.16 | 1.01 | 1.26 | 1.35 | 1.25 |
| AUEC† | pg*µg protein$^{-1}$*day | 15 | 13.8 | 17.4 | 18 | 18.9 |

†Estimated from time zero to last time point

Within 2 weeks post MIND implantation, significant BDNF upregulation in all tissues, in comparison to naïve BDNF levels is observed, as is shown in FIG. 17A. A 2-fold 17C) 28 days relative to protein levels of naïve animals of comparative ages, measured by BDNF ELISA (n=4 rats/group, fold change values represented as mean±SEM, *p<0.05, p<0.01, *p<0.001, One-way ANOVA with Tukey post-hoc test for multiple comparisons for FIG. 17A, student's t-test for FIG. 17B and FIG. 17C.

Figure 17D:
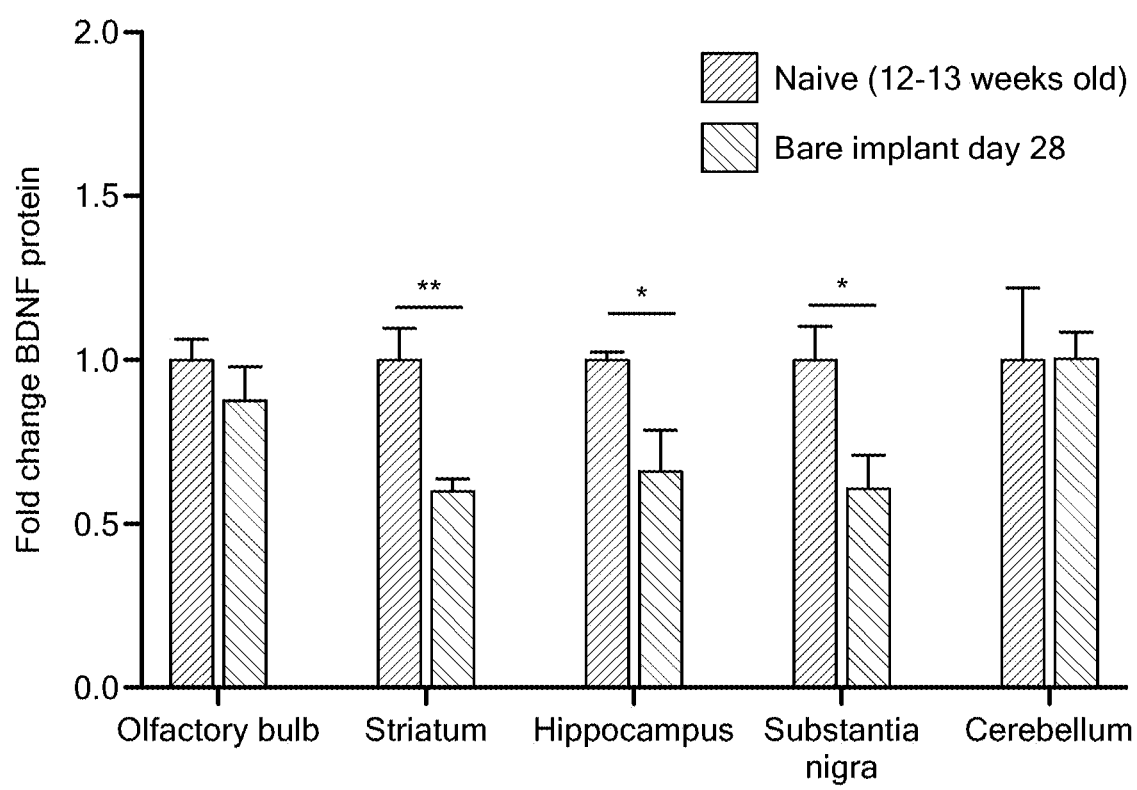
FIG. 17D shows BDNF protein levels in brain sub-regions of rats administered with bare or placebo implants via MIND for 28 days relative to the BDNF levels of naïve animals of comparative ages, measured by BDNF ELISA (n=4 rats/group, fold change values represented as mean±SEM, student's t-test, **p<0.01, *p<0.05).

Semba, et al. has previously quantified the specific changes in BDNF concentrations in different regions of rat brain in the course of its development and aging for ~6 months (Katoh-Semba & Takeuchi, 1997). While regions such as olfactory bulb, hippocampus and cerebellum clearly indicate a steady increase in BDNF levels in the course of aging until 60-120 days, regions such as cerebral cortex, hypothalamus and striatum exhibit an opposite oscillating trend of an increase followed by a steep decrease around the same time frame. These findings also underline the broad and differential expression of BDNF mRNA throughout the adult brain. This stands in contrast to other neurotrophins, such as NT-3, with much narrower and limited mRNA distribution, which makes BDNF more susceptible to intricate variations under different treatment conditions (Conner, et al., 1997; Castren, et al., 1995; Guthrie & Gall, 1991; Ceccatelli, et al., 1991; Phillips, et al., 1990). To further probe these findings, the studies herein also include animals implanted with bare or placebo core-shell implants (without BDNF-AT) as an additional negative control for the extended time point of 28 days, and their BDNF levels are compared to those of rats of comparable age group (FIG. 17D). It is noted that there is no increase in BDNF levels with the placebo implant. While there are no statistical differences between the BDNF levels of olfactory bulb and cerebellum of implant bearing rats relative to their respective controls, other tissues show a 0.2-0.3 fold decrease, further highlighting the need and importance of BDNF AT to induce BDNF protein upregulation.

To further evaluate the outcomes associated with the novel implant formulation, the kinetics of the BDNF response are also evaluated via NCA, and the data are summarized in Table 5. This analysis suggests that the BDNF response kinetics behave somewhat similarly amongst the brain tissues, irrespective of distance from the implant site. Indeed, $C_{max}$ values range from 1.01-1.35 pg*µg protein$^{-1}$ for all brain tissues (Table 5). Moreover, the AUEC values, which represent the extent of BDNF response over this timeframe, range from 13.8-18.9 pg*µg protein$^{-1}$*day.

Collectively, the kinetic parameters describing the BDNF response suggest that there are tissue-specific responses to BDNF-AT exposure that are not directly proportional to AT exposure. These findings re-affirm the previously observed lack of a direct PK/PD relationship for BDNF AT (Padmakumar, et al., 2021). The tissue-specific amounts of BDNF mRNA and variable BDNF NAT strongly influence the extent of BDNF upregulation induced by the inhibition of BDNF-AS by AT binding, mechanisms which support an indirect PK/PD response for the BDNF AT (Modarresi, et al., 2012; Mazur, et al., 2019). Moreover, these findings indicate that future PK/PD modeling of BDNF AT will require special considerations including region-, age-, and species-specific variations in response. These nuances of the BDNF response present a challenge for animal to human allometric scaling, and therefore extra care must be taken with model validation to account for the anticipated variabilities in response. Importantly, the technology disclosed herein enables flexibility in delivery to the CNS to meet these challenges.

Figure 18A:
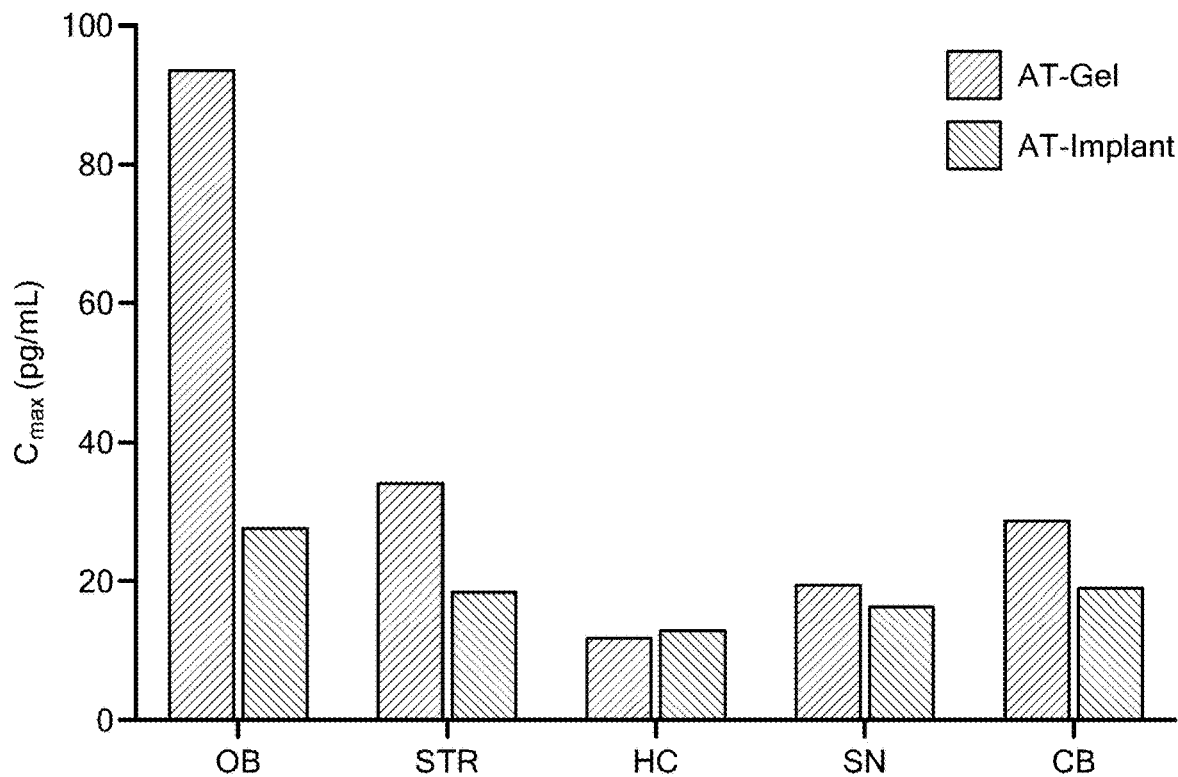
FIGS. 18A-18G show relative delivery efficiency of BDNF antagNAT (AT) using MIND implant as compared to a MIND AT-Gel depot reported (Padmakumar, et al., 2021). Comparisons are shown by kinetic analysis of the AT concentrations by noncompartmental analysis with respect to (18A) $C_{max}$; (18B) AUC; (18C) MRT; (18D) overall percent changes. Comparisons are shown by kinetic analysis of the actual BDNF protein concentrations by noncompartmental analysis with respect to (18E) $C_{max}$; (18F) AUEC; (18G) overall percent changes.
Figure 18B:
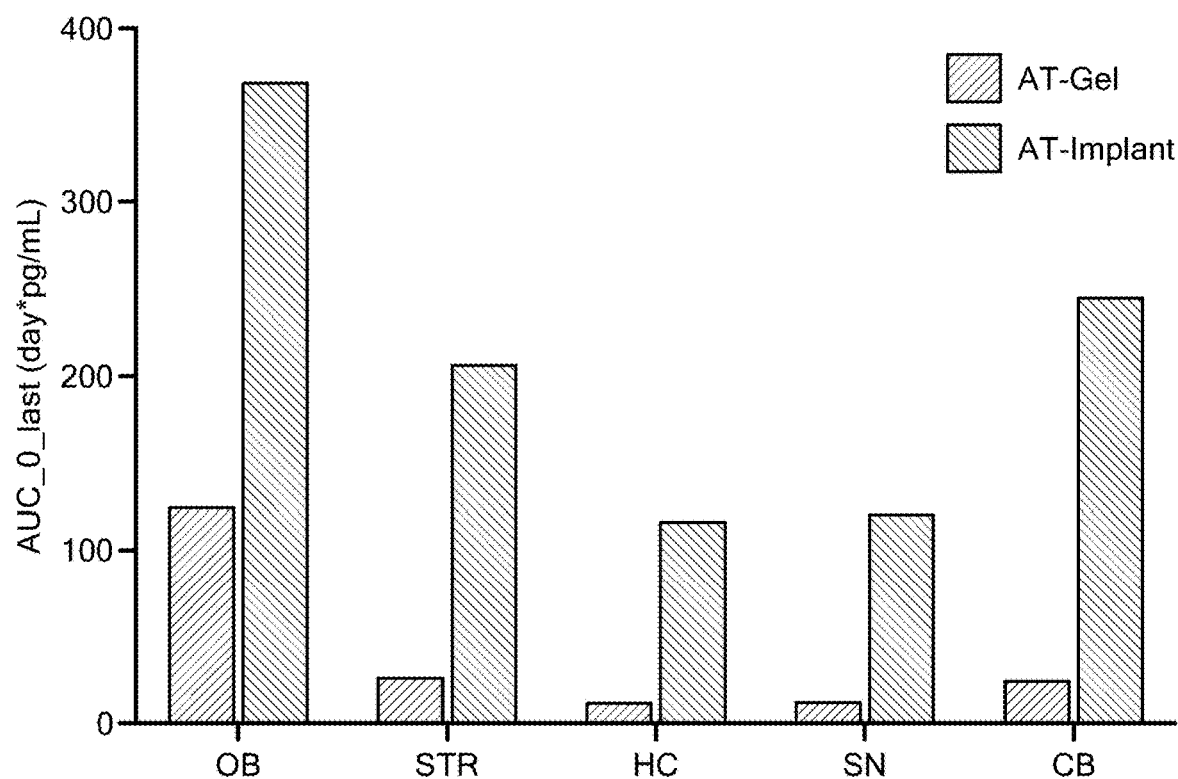
Figure 18C:
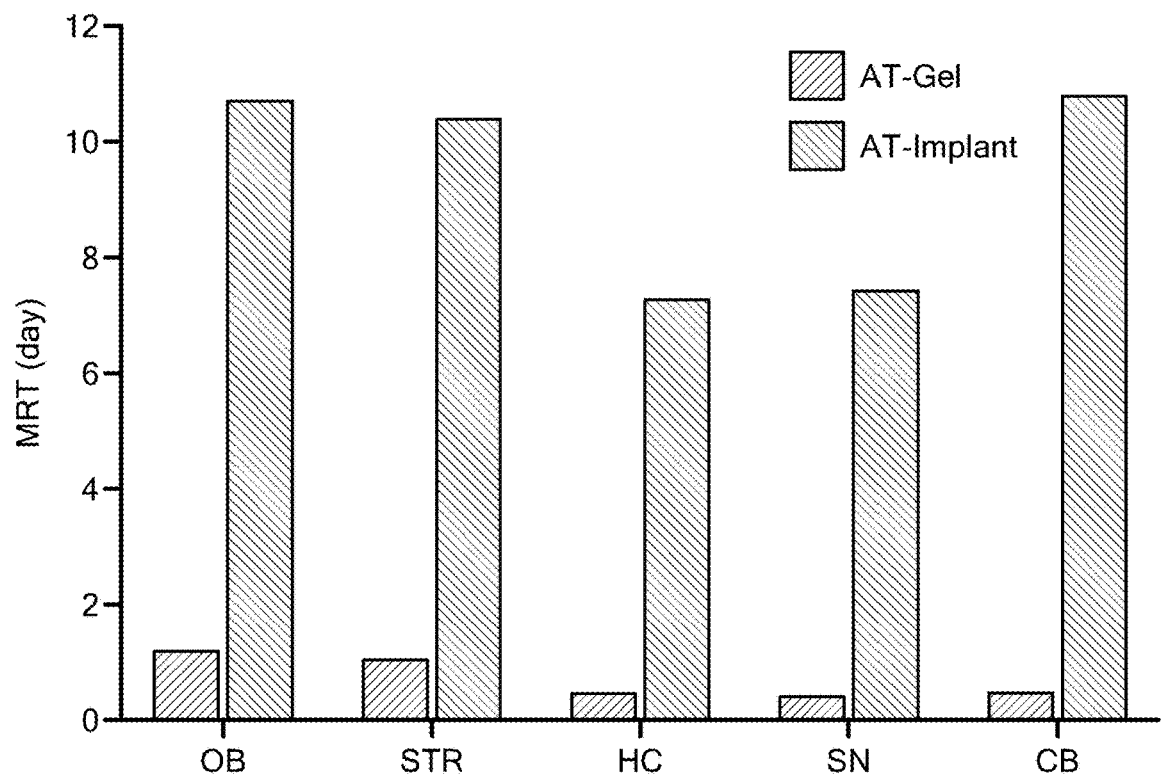
Figure 18D:
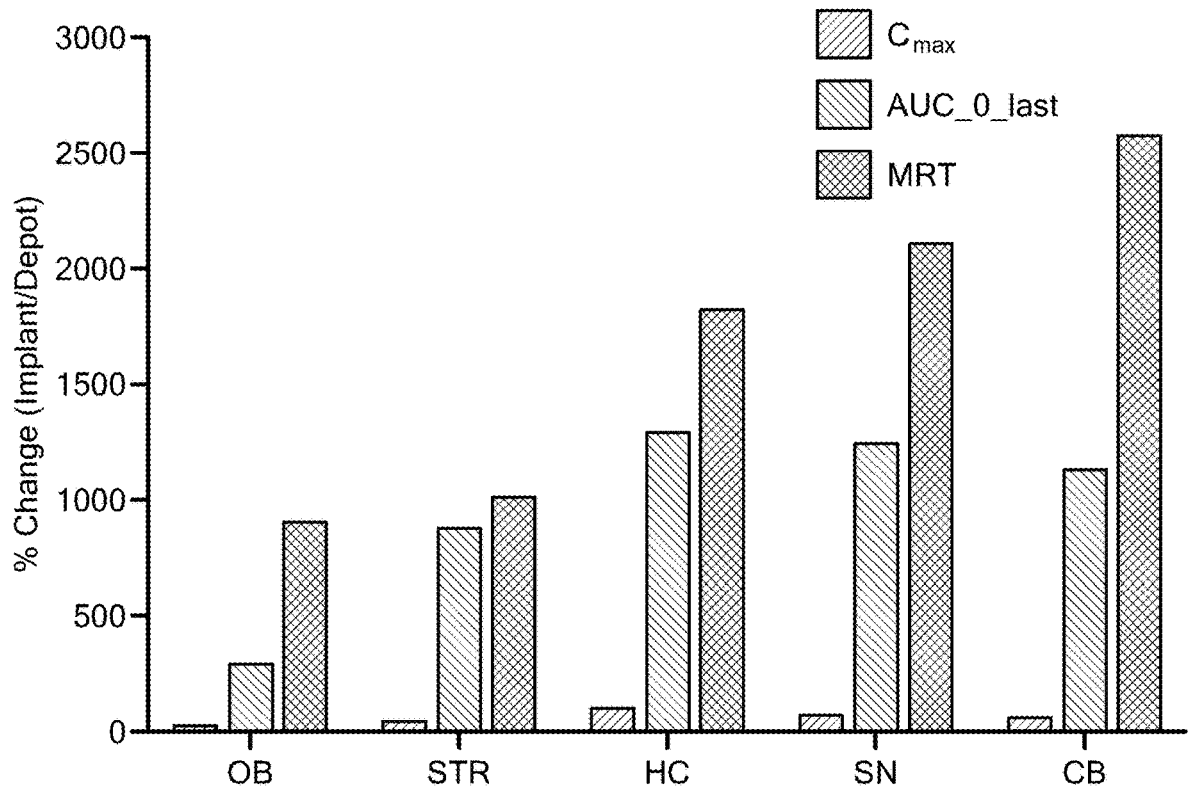
Figure 18E:
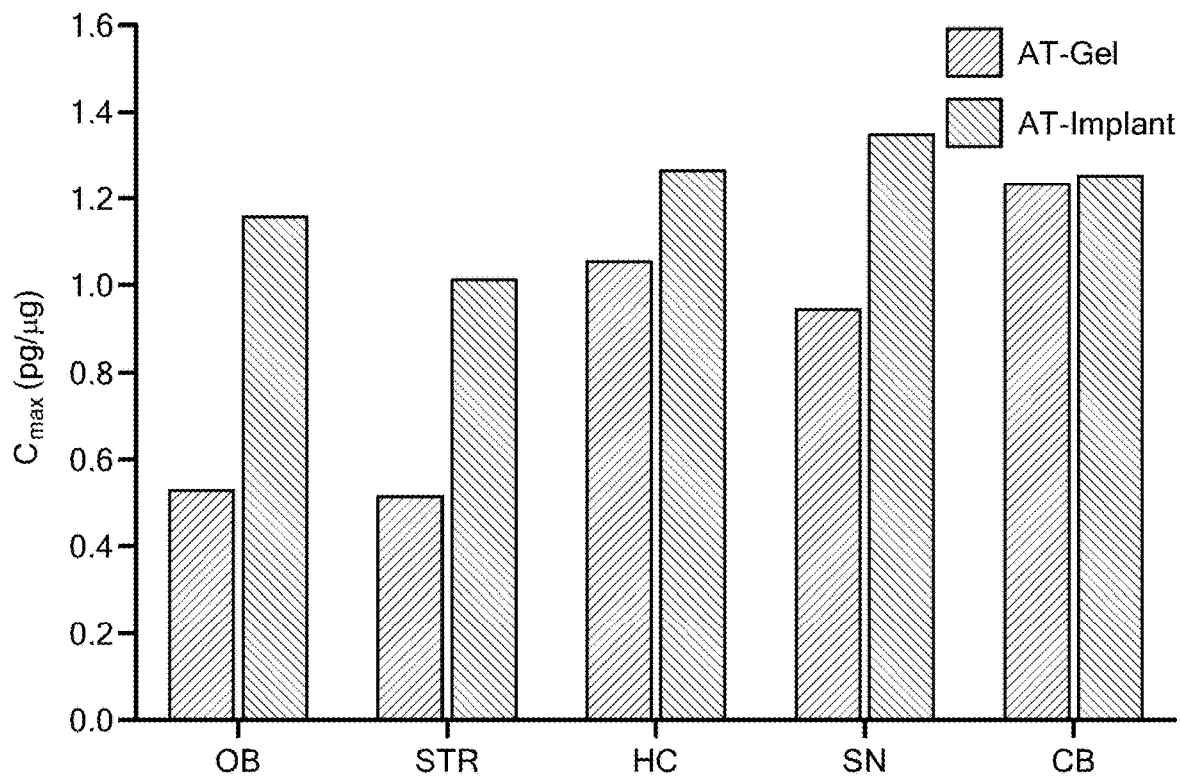
Figure 18F:
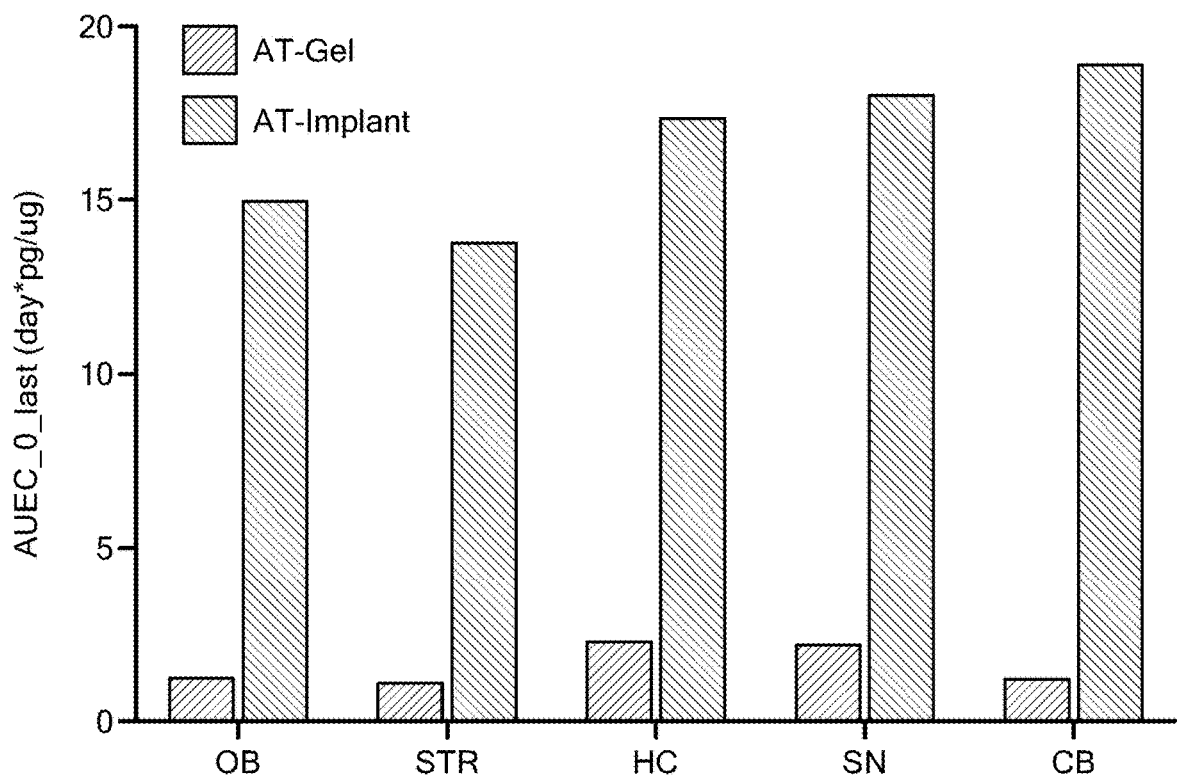
Figure 18G:
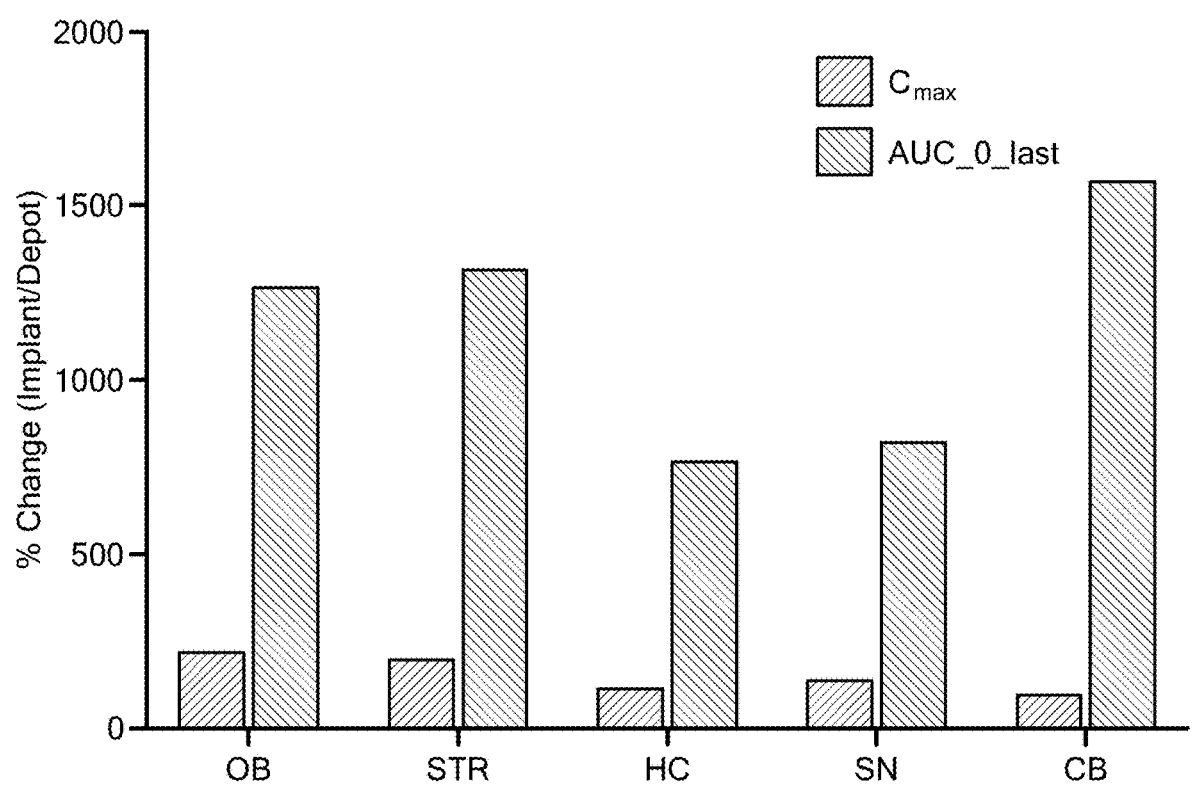

Having established the sustained AT delivery potential of core-shell implants, the performance of the implants is further evaluated by comparing the data with that of an AT-Gel (BDNF AT dispersed in Pluronic-F127 gel; same AT dose of 0.15 mg/kg) reported by Padmakumar, et al., and the comparisons are shown in FIGS. 18A-18G (Padmakumar, et al., 2021). Given the additional complexity of the example core-shell implant formulation, relative to the AT-Gel, it is critical to establish the relative delivery efficiency of the novel formulation and therefore discern the added value. The previously reported AT-Gel depot data from 0-96 hours (Padmakumar, et al., 2021) is utilized for this comparison since the terminal data points are at or under the limits of detection, and any later time points are expected to give non-quantitative results. Using NCA data for both formulations, the $C_{max}$, MRT and AUC or AUEC ratios are calculated for the MIND implant relative to the MIND depot, for both AT (FIGS. 18A-18D) and BDNF protein levels (FIGS. 18E-18G).

As shown in FIG. 18A, the AT-implant formulation substantially reduces the $C_{max}$ in the OB and reduces the tissue-to-tissue variability in $C_{max}$, relative to the depot ("AT-Gel", FIG. 18A) formulation. As shown in FIG. 18B, the AT-implant formulation substantially increases the exposure in all tissues, as measured by AUC, when compared to the AT-gel depot. Indeed, exposure in the deep brain tissues of interest, such as the HC, SN, and CB, shows a remarkable 1000% increase. Exposure in the OB is only increased by 300%, which suggests that the implant formulation increases the fraction of the dose reaching the end target regions in addition to increasing overall exposure relative to the AT-gel depot. In addition to increasing the extent of exposure, the example implant formulation greatly increases the duration of exposure as determined by MRT (FIG. 18C), with tissue-specific increases ranging from nearly 1000% in the OB and STR to over 2500% in the CB. Collectively, these changes in peak and cumulative exposure (FIG. 18D) suggest that the implant formulation is able to flatten and extend the AT concentration-time curve and thereby enhance the delivery efficiency of an equivalent AT dose when compared to the gel depot.

A comparison of the kinetics of the BDNF response shows that the implant formulation increases the BDNF $C_{max}$ relative to the depot (FIG. 18E), which stands in contrast to the effect seen on AT $C_{max}$. The maximum BDNF concentration in the OB increases by nearly 250% for animals treated with the implant formulation, which suggests that the BDNF response is not driven by the AT $C_{max}$. Interestingly, the $C_{max}$ of the BDNF response does not change substantially for deep brain tissues in animals implanted with MIND core-shell implants. As shown in FIG. 18F, treatment with MIND core-shell implants substantially increases the cumulative BDNF exposure, as determined by the AUEC, by nearly 1000% in all tissues when compared to the gel depot formulation. The changes in BDNF response kinetics for the implant relative to the gel depot (FIG. 18G) demonstrate that the novel formulation is able to substantially extend the cumulative BDNF exposure for the same dose of BDNF-AT. The observed differences in exposure to AT and BDNF suggest differences in the intrinsic tissue response to AT, likely due to tissue-specific differences in BDNF mRNA levels and/or BDNF NAT levels (Modarresi, et al., 2012; Mazur, et al., 2019). The comparisons are made by kinetic analyses of AT concentrations by noncompartmental analysis with respect to (FIG. 18A) $C_{max}$; (FIG. 18B) AUC; (FIG. 18C) MRT; (FIG. 18D) overall percent changes. The comparisons by kinetic analysis of BDNF protein concentrations by noncompartmental analysis are with respect to (FIG. 18E) $C_{max}$; (FIG. 18F) AUEC; and (FIG. 18G) overall percent changes.

Figure 19A:
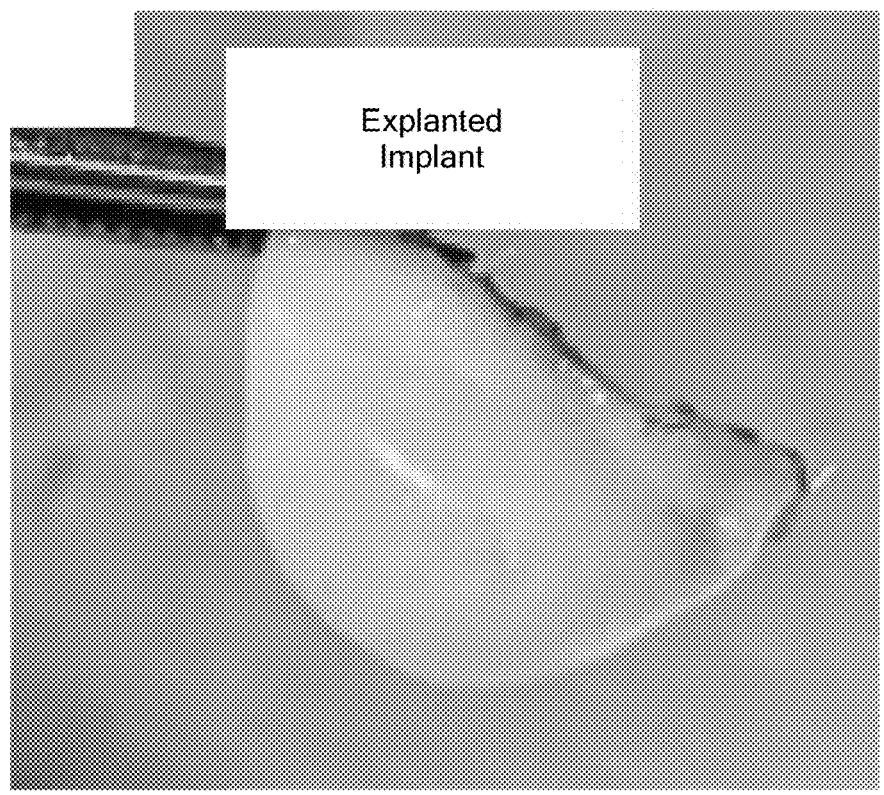
FIG. 19A shows an image of a MIND implant explanted from a rat submucosal space after euthanasia.
Figure 19B:
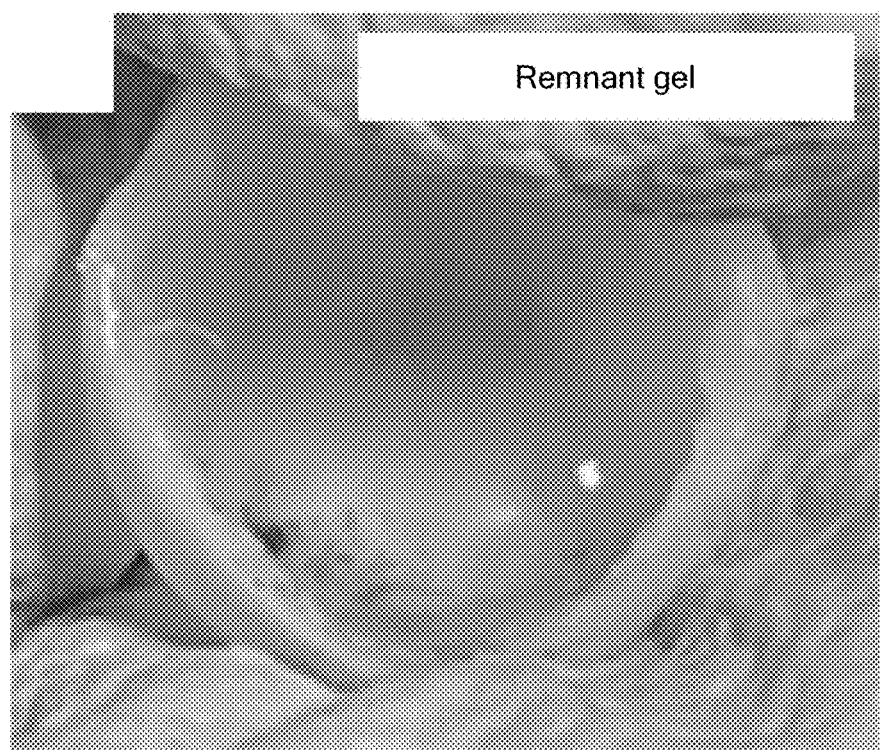
FIG. 19B shows an image of the explanted implant cut open to retrieve the remnant gel volume.
Figure 19C:
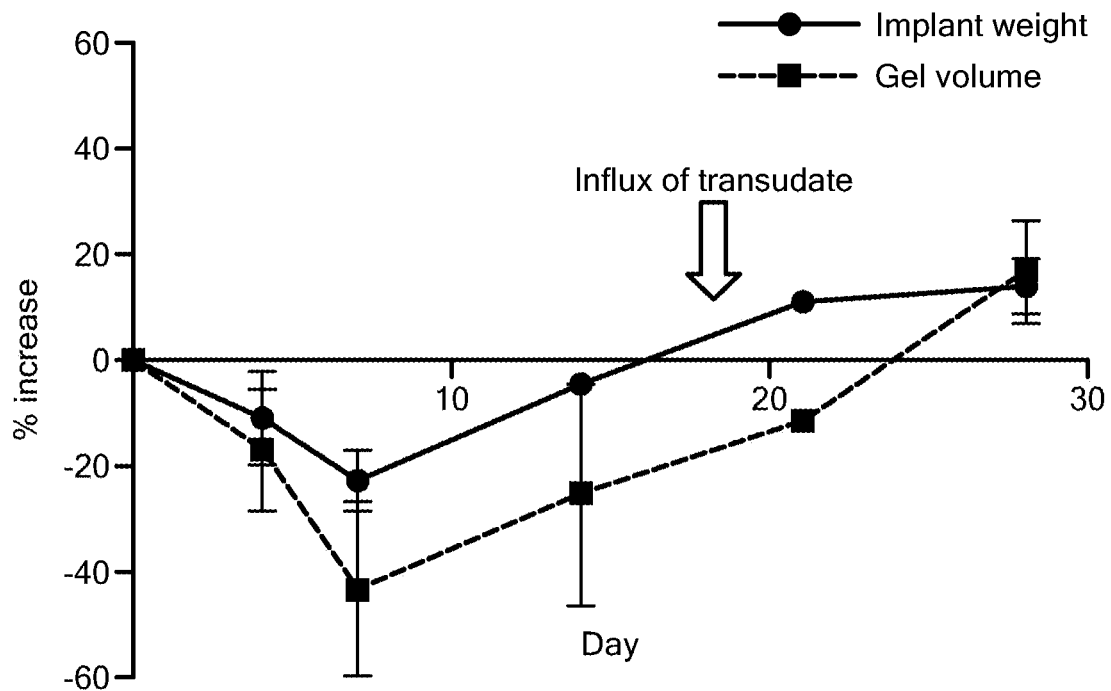
FIG. 19C shows plots illustrating quantification of changes in the weights of explanted implants and remnant gel volumes with respect to time.

During the studies herein, implants retrieved from the surgery sites upon rat sacrifice (e.g., FIG. 19A) at different time points (FIG. 20A) are weighed and thereafter cut open to withdraw the remnant gel volumes (FIG. 19B). As shown in FIG. 20A, all implants are found to preserve their original shape without distinct changes in morphology. In FIG. 20A, an increase in the volume of core is noted for implants retrieved at late time points. To further study this, FIG. 19C shows the percent change in implant weights and remnant gel volumes. As evident from FIG. 19C, implants of the initial time points display a slight decrease in weights which is then followed by an increase within 14 days, when compared to the weights of implants pre-implantation. A 20% increase in weight is noted around 21 and 28 days. Similarly, the remnant gel volume collected from implants at the initial time point is smaller than the remnant gel volume from longer time points such 21 and 28 days. This can be attributed to the mechanism of diffusion which favors the release of BDNF AT from the core to the rat submucosal space. However, with the progression of time, the Pluronic F-127 gel core also enhances the permeation rate of biological fluid present in the vicinity of the implant due to an osmotic action, and contributes to the increase in the weight of implant as well as the gel volume at longer time points (also seen in the implants of late time points shown in FIG. 20A).

Figure 19D:
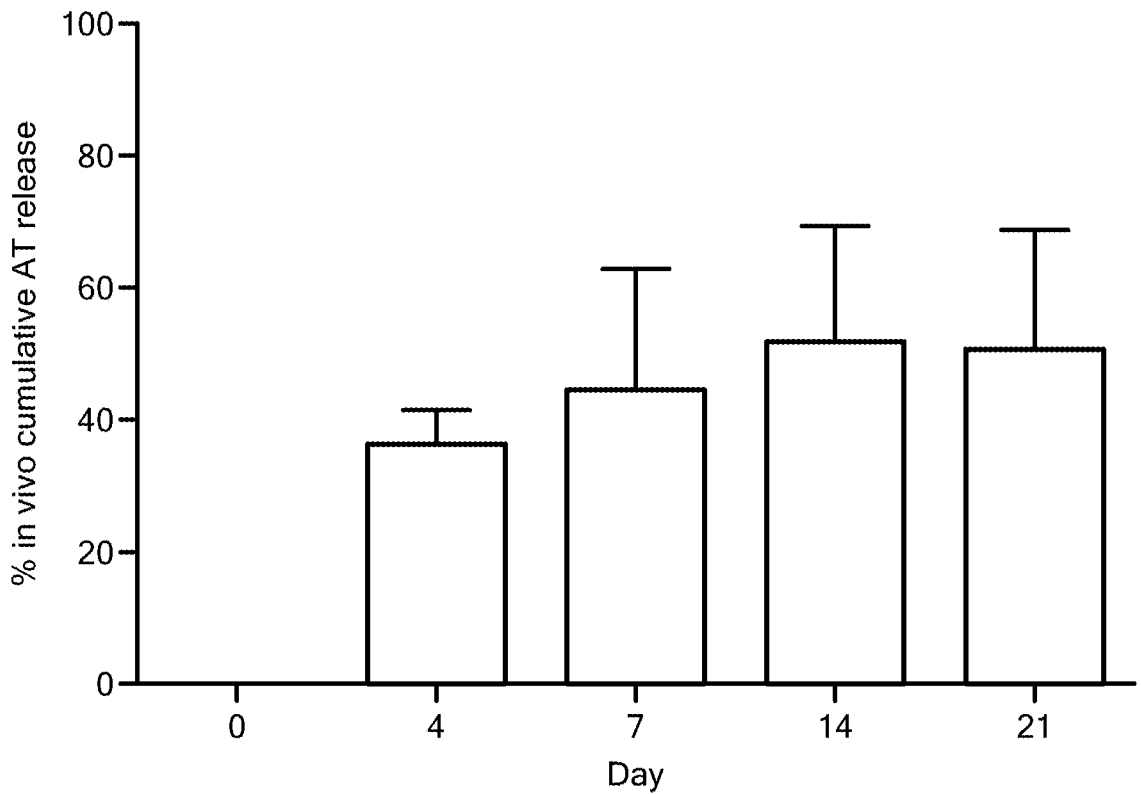
FIG. 19D shows in vivo cumulative release of BDNF AT from core-shell implants determined using a nanodrop spectrophotometer.

The remnant AT amounts in retrieved gel fractions were analyzed and compared to the initially loaded AT amounts to compute the in vivo cumulative AT release %. The in vivo cumulative AT release % is presented in FIG. 19D. It is observed that ~30% of BDNF AT is released from the implant in vivo within the first few days, which increases to ~45% by 1 week and 50% by week two. The slow release rate of AT after day 4 also emphasizes the role of diffusion as the prominent mechanism at the initial time points and can also be related to the higher BDNF AT levels detected in brain regions at these time points (FIGS. 16A-16F). However, the rate of AT release post 2 weeks could be slowed down due to the compounded effects of water permeation into the core matrix. A cumulative AT release of ~50-60% from implants explanted at week 3 is noted, which strongly indicates the possibility of further release (of the remaining 40%) gradually over time. However, during this work an accurate gel fraction from the $28^{th}$ day implants cannot be extracted, as there are higher amounts of transudates mixed with the gel which subsequently interferes with the sample processing and remnant AT analysis. The smaller fraction of BDNF AT released in the longer time points can also be correlated to the relatively lower amounts of BDNF AT detected in the deeper brain tissues at these timepoints (FIGS. 16A-16F). This also emphasizes the utility of the implants disclosed herein as drug delivery depots favoring slower yet sustained release profiles.

The surface morphology of all explanted implants is evaluated qualitatively by FESEM and is presented in FIGS. 20B-20F. The (outer) surface morphology of implants before implantation is evaluated qualitatively by FESEM and is presented in FIG. 11 and FIG. 12. The changes to the explanted implant morphology at day 4 (FIG. 20B) are minimal except for the coarse surface topography and enhanced roughness relative to pre-implanted ones, which is expected to happen in the course of contact with a biological fluid/surgery site. The implant surface at day 7 (FIG. 20C) shows small pore-like structures which can possibly form along the course of the matrix hydration. The surface at day 28 (FIG. 20F) shows the presence of small cracks or crevices, which are typical characteristics of the onset of polymer degradation or erosion (Visan, et al., 2020; Lyu, et al., 2019). These observations suggest the possibility of polymer degradation becoming the dominant release mechanism at later timepoints instead of diffusion. Although PCL has a slow biodegradation profile, the exposure to transudates, the surrounding biological milieu and enhanced rate of water permeation triggered by the osmotic core could accelerate its degradation profile.

Figure 23:
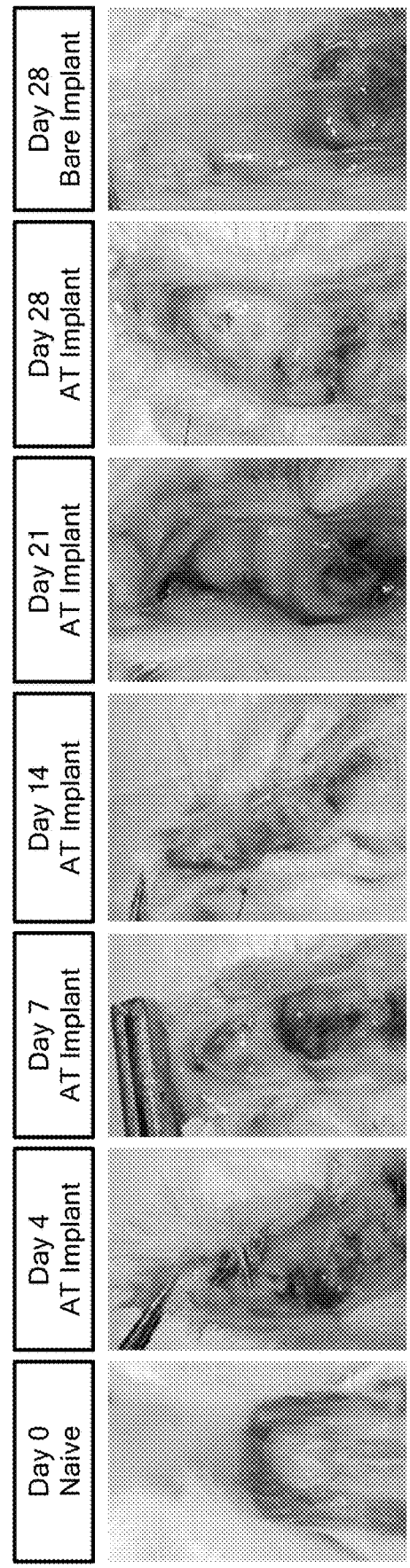
FIG. 23 shows images of rat submucosal space after removal of an AT implant post-euthanasia at day 0, day 4, day 7, day 14, day 21, day 28, and after removal of a bare implant at day 28 (far right).

The safety of the MIND approach in naïve Sprague Dawley rats has been established (Padmakumar, et al., 2021). The animals remained healthy throughout the treatment period of 28 days without any significant changes in their routine activities or behavior. Upon euthanasia at different time points, the implantation site within the rat submucosal space was carefully inspected (FIG. 23) to check for any visual signs of inflammation, tissue ingrowth or fibrous capsule formation around the implant, which are the commonly observed signs of foreign body reaction (Nayyer, et al., 2016; Atlan, et al., 2018). As illustrated in FIG. 23, there are no abnormalities in the rat nasal cavities or any prominent signs of infection or tissue ingrowth.

The technology contemplates that, for each specific application, it is imperative to evaluate the long-term safety of the procedure as well as biocompatibility of the core-shell implants. Further, the tissues from the interface of implant and nasal cavity are collected to qualitatively assess these signs by standard histological analysis as illustrated in FIGS. 21A-21G. FIGS. 21A-21G show the histological evaluation (H & E stained images, scale bar at lower left corresponds to 100 µm) of nasal tissues retrieved from the MIND implantation site of rats after euthanasia at different timepoints. The inset images in FIGS. 21A-21G show the photographs of tissue with the implants at different time points. Apart from a slightly thickened epidermis observed at the initial few time points, which is expected as the response to the surgical incision, there are no significant changes in the tissue histology of implanted animals relative to the intact histology of untreated animals. The absence of any prominent histological signs of adverse tissue reactions confirms the biocompatibility of the fabricated core-shell implants.

The present study demonstrates the development and application of biodegradable implants with a unique osmotic core and polymeric shell design as a potential strategy to prolong delivery of BBB impermeant biological therapeutics to the CNS via the MIND technique. Using a straightforward implant fabrication followed by MIND implantation procedure, evidence of sustained release and delivery of the therapeutic to specific regions in Sprague-Dawley rat brain is demonstrated. The implant composition and dimensions can be tailored for specific therapeutic payloads and indications.

In the context of BDNF AT delivery, an osmotic Pluronic F-127 gel core entrapping BDNF AT and a PCL dip-coated sheath enables the modulation and optimal control of the release of AT over sustained duration as compared to the previously reported gel depot (Padmakumar, et al., 2021). The example implants herein result in a more efficient and prolonged CNS uptake of BDNF AT relative to previously reported gel formulations of BDNF AT. A substantial 1000% enhancement in the cumulative BDNF exposure for animals administered with the MIND implant is observed, particularly in regions such as hippocampus and substantia nigra, which are important for Alzheimer's disease and Parkinson's disease therapies. Therefore, the core shell implant technology coupled with MIND approach can synergistically serve to improve the CNS uptake and prolonged delivery of therapeutics to the brain for extended time periods. The MIND dechnique is directly derived from routine, minimally invasive, non-surgical Ear, Nose and Throat (ENT) clinic procedures, and the implant fabrication can be kept fairly simple and flexible. As shown in FIG. 24B, performance of an intranasal procedure can be accomplished with an awake patient during an outpatient visit to the Otolaryngology (ENT) clinic. The implants disclosed herein can be placed in a human nose within the submucosal space of the olfactory epithelium (FIG. 24A). For example, a catheter can be introduced into a nostril and utilized to contact the submucosal tissue. A dilation balloon, extended from the catheter, can be utilized to define a space in the olfactory epithelium (OE) for the implant, and the implant is subsequently deposited into the defined space of the OE within the submucosal tissue. The human OE includes only about 3-5% of human nasal surface area and is positioned within a narrow cleft facilitating only smaller volumes of drug administration and limited topical drug distribution (Padmakumar, et al., 2021). A drug contacting the OE has an effective residence time of only about 15-20 minutes before it is cleared by mucociliary action. During this period, the nasal mucus can further exert a degradatory effect through an array of secreted proteases and nucleases. The residual drug must diffuse through the semipermeable epithelial cell layer in order to gain access to the olfactory nerve sheaths (Padmakumar, et al., 2021). By utilizing an implant, a direct anatomic conduit into the brain via the olfactory neurons which innervate the olfactory epithelium is utilized over time. Using this conduit, the implants disclosed herein can provide long-term delivery of a therapeutic agent. Consequently, the resulting combined MIND Implant approach can be directly clinically translated for the treatment of chronic age-related neurodegenerative diseases, for example, Alzheimer's and Parkinson's disease.

The present technology has been described in conjunction with certain preferred embodiments and aspects. It is to be understood that the technology is not limited to the exact details of construction, operation, exact materials or embodiments or aspects shown and described, and that various modifications, substitution of equivalents, alterations to the compositions, and other changes to the embodiments and aspects disclosed herein will be apparent to one of skill in the art.

EXAMPLES

Example 1. Materials and Analysis

Poly (ε-caprolactone) (PCL, molecular weight of 50 kDa) and the organic solvent 2,2,2-trifluoroethanol (2,2,2-TFE) were purchased from Polysciences Inc. (Warrington, PA) and Acros Organics (Fair Lawn, NJ), respectively. Pluronic F-127 was obtained from BASF Corp. (Florham Park, NJ). BDNF expressing AntagoNAT was provided by Opko Health (Miami, FL). The dye, fluorescein isothiocyanate (FITC)-Dextran (average molecular weight 3-5 kDa) used for in vitro release studies and EDTA-free Protease Inhibitor tablet used for making the tissue homogenization buffer were procured from Sigma Aldrich (St. Louis, MO). The Pierce BCA assay kit for protein quantification, ELISA Femto Solution Mix, and 96 well white Nunc™ plates used for the BDNF AT hybridization assay were obtained from Thermo Fisher Scientific (Waltham, MA). The capture and detection probes used for hybridization assay were designed by Qiagen Inc. (Germantown, MD). 4×SSC/0.5% sarkosyl, 10% (v/v) neutral buffered formalin and histoplast paraffin wax were bought from Fisher Scientific (Fair Lawn, NJ). Streptavidin-HRP conjugate used for the hybridization assay was procured from Jackson Immuno-Research (West Grove, PA). ChemiKine Brain Derived Neurotrophic Factor sandwich ELISA kit for BDNF level quantification was purchased from Millipore Sigma (Burlington, MA). The drill used for the in vivo surgery protocol was obtained from Dremel (Mt. Prospect, IL) and 5-0 nylon sutures used for incision closures were purchased from Med-Vet International (Mettawa, IL).

GraphPad Prism (version 6.01) was used for all statistical analyses with significance set at $p<0.05$. Average of experimental read out values were collected from all independent experiments and final data were represented as mean±SEM. Student's t-tests and one way ANOVA with post-hoc Tukey tests were used for comparisons to determine the statistical significance.

Example 2. Fabrication of BDNF AT-Loaded Osmotic Core-Shell Implants

BDNF AT loaded osmotic core-shell implants were fabricated in a step-wise manner. The biodegradable polycaprolactone (PCL) shell was fabricated using the conventional technique of dip-coating. For this, PCL solutions of different concentrations in the range of 10-14 w/v % were pre-formed by dissolving the polymer in the organic solvent 2,2,2-trifluoroethanol (TFE). A lubricated cylindrical glass rod of ~5 mm diameter (coating substrate) was then dipped into the PCL-TFE solution of optimized concentration for ~1 minute. The dipped rod was then pulled out of the solution and air-dried. The number of dipping-drying cycles was optimized so as to obtain a thick polymeric sheath. Formation of the polymeric sheath is illustrated at the left of FIG. 10A. The fabricated PCL shells were subjected to overnight vacuum drying in a desiccator to facilitate the removal of residual organic solvent. PCL shells were thereafter carefully peeled off from the substrate rods thereby forming hollow reservoirs as illustrated in FIG. 10B. The shell wall thickness was measured using a micrometer screw gauge (Eisco, Victor, NY).

To fabricate the BDNF AT-loaded osmotic core, the osmotic core component of the implant included thermosensitive Pluronic F-127 gel. A 30 w/v % solution was pre-formed by dissolving Pluronic F-127 in 1×PBS at 4° C. upon continuous stirring. BDNF AT pre-aliquoted in water (2 mg/mL concentration) was added to 300 μL of the homogenous Pluronic F-127 solution under stirring. The thermogelling property of Pluronic F-127 was exploited to formulate a gel-based osmotic core at room temperature (about 25° C.).

The assemble the final core-shell implant, the volume of Pluronic F-127 gel entrapping BDNF AT corresponding to the in vivo therapeutic BDNF AT dose for rats (0.15 mg/kg) or the gel alone without BDNF AT was added into the fabricated biodegradable PCL shell reservoir, keeping the shell in a vertical position (FIG. 10A, center). After this step, the remnant length of shell was shortened and its open end was sealed with heat using a cautery pen as is illustrated in FIG. 10A.

The characterize the PCL shell morphology (e.g., FIG. 11, FIG. 12), the morphology of PCL shell surface was qualitatively assessed by field emission scanning electron microscopy (FESEM) (Hitachi S-4800 FESEM, Tokyo, Japan). The samples were sputter coated with 5 nm of platinum using a sputter-coater (Cressington 208HR, Watford, UK) and imaged with an accelerating voltage of 3 kV.

Example 3. In Vitro Release of FITC Dextran from Core-Shell Implant

Implants were fabricated according to the above-described procedure with fluorescein isothiocyanate (FITC)-Dextran dye (2 mg/mL) as the payload. They were then immersed in Phosphate Buffered Saline (PBS) reservoir (pH 7.4, 37° C., 100 rpm shaking). At time points such as 0, 3, 6, 24, 48 hours, 6, 11, 21 and 29 days, a definite volume was retrieved from the PBS reservoir and thereafter replenished with the same volume of fresh PBS to facilitate sink conditions. FITC fluorescence intensity of the collected aliquots were measured using a plate reader (Biotek, Winooski, VT) at excitation and emission wavelengths of 490 and 520 nm respectively. Cumulative FITC-dextran release was calculated and plotted as a function of time, and the data is presented in FIG. 13.

Example 4. In Vivo Administration of the Implants Using MIND Approach in Sprague Dawley Rats The guidelines developed by the Institutional Animal Care and Use Committee (IACUC) of Northeastern University were followed for designing the animal experiments. Sprague Dawley rats (males, 250-300 g weight) were procured from Charles River Laboratories (Wilmington, MA) for the study. All animals were provided with drinking water and diet ad libitum, and they were maintained under standard conditions of 12 h light cycle/12 h dark cycle.

The in vivo surgical implantation of core-shell implants in naïve rats was carried out with the MIND protocol developed in Padmakumar, et al., 2021. Rats anesthetized with 2% isoflurane were placed on a stereotactic apparatus equipped with ear bars, and body temperatures were maintained at 37° C. The surgical site located at the snout was prepped aseptically with povidone iodine and alcohol. A 1 cm long midline sagittal incision was made with a sterile scalpel blade followed by the elevation of bilateral skin flaps to expose the underlying paired nasal bones (FIG. 15A). These nasal bones were removed using a high speed surgical drill, without disturbing the deep layer of basolateral olfactory mucoperiosteum. This exposure provided for a subcutaneous cavity in direct contact with the basolateral olfactory epithelium (FIG. 15B). The implant, including BDNF AT entrapped in gel osmotic core and PCL shell (pre-sterilized by UV irradiation), was inserted into this cavity (FIG. 15C) followed by closure of the skin incision using 5-0 nylon suture (FIG. 15D). Animals were randomly assigned to five groups and sacrificed at day 4, 7, 14, 21 or 28 (n=4 rats/group) post-surgery. Control groups consisted of both age and sex matched untreated naïve animals as well as animals treated with placebo implants containing the Pluronic F-127 gel core without any BDNF AT payload. All animals subjected to the MIND procedure were monitored daily for any signs of health deterioration or changes in normal behavior throughout the study period of 28 days.

Example 5. In Vivo Distribution of BDNF AT Levels in Rat Brain Sub-Regions

Rats implanted with BDNF AT core-shell implants via MIND approach were sacrificed at the above-mentioned time points post-surgery. Blood samples were collected by cardiac puncture prior to euthanasia so as to quantify the BDNF AT levels in plasma collected as supernatants upon centrifugation for 10 minutes at 2000 g and 4° C. Following the sacrifice procedure, rat brains were harvested and various sub-regions of interest were isolated based on rat brain atlas co-ordinates along with the olfactory bulb. Samples from striatum, hippocampus, substantia nigra and cerebellum were retrieved using 3 mm tissue biopsy punches, which were thereafter homogenized with ice-cold tissue lysis buffer constituted by dissolving 10 mM Tris-HCl at pH 7, 0.4 mM EDTA, 100 mM NaCl, 2 g BSA, 1.54 mM sodium azide and 2% Triton X-100 in 100 ml of water added with EDTA-free Protease Inhibitor tablet. Total protein samples from tissue homogenates were collected as supernatants after a 20 min centrifugation at 20000 g and protein content was quantified with standard BCA assay. The BDNF AT levels in these tissue extracts as well as plasma samples were quantified by AT hybridization assay described previously (Padmakumar, et al., 2021).

The BDNF AT sequence contains phosphorothioate bonds represented by '*'. 5'-C*A*T*A*G*G*A* G*A*C*C*C*T*C*C*G*C*A*A*C-3' (SEQ ID NO. 1) was of interest for design of capture probes, detection, and quantitative studies (CATAGGAGACCC TCCGCAAC=SEQ ID NO. 1). For the BDNF AT sequence: 5'-C*A*T*A*G*G*A*G*A*C*C*C*T*C*C*G*C*A* A*C-3' (SEQ ID NO. 1) capture probe and detection probes were designed with sequences given below, such that they were complementary to the 3' and 5' ends of BDNF AT respectively. Capture probe sequence: 5AmMC12//iSp18/ iSp18//G*+T*+T*+G*+C*+G*+G*+A*+G. Detection probe sequence: +G*+G*+T*+C*+T*+C*+C*+T*+A*+ T*+G/iSp18//iSp18//iBiodT//3BioTEG (GGTCTCCTATG=SEQ ID NO. 2); wherein * refers to phosphorothioate bond, + to LNA (locked nucleic acid) modifications, iSp18 to internal 18-mer spacer, 5AMmc12 to 5'-amino modifier C12m, 3BioTEG to 3' biotin-TEG and iBiodT to internal biotin-dT.

A 96-well white Nunc™ plate was coated with a solution made by dissolving 40 μL of 5000 pmole/mL capture probe to 19.96 mL of capture probe buffer. BSA blocking was performed as the next step followed by thermal annealing of samples added with detection probe. The detection probe solution was made by adding 200 μL of 5000 pmole/mL detection probe in 19.8 mL of buffer constituted by 4×SSC/ 0.5% sarkosyl. A streptavidin-HRP conjugate diluted at 1:50,000 ratio was subsequently added to the washed plate. An incubation step at 37° C. for 30 minutes was then followed by washes. Finally, the wells were added with 150 μL of the ELISA Femto Solution Mix and luminescence read outs were taken immediately with a plate reader (Biotek, Winooski, VT).

The calculated BDNF AT levels were normalized to the amount of protein in each sample and expressed as pg AT/μg protein.

To perform the pharmacokinetic analysis of BDNF AT concentration in rat brain sub-regions, antagoNAT amounts per gram tissue were converted to concentration (i.e., pg/mL) using reported values for rat brain density (DiResta, et al., 1990) in order to facilitate future modeling and simulation. Noncompartmental analysis (NCA) of the concentration-time data was performed using the SimBiology application within MATLAB software (version #2020a) (Noncompartmental Analysis, 2017). The maximum concentration ($C_{max}$) and time of maximum concentration ($t_{max}$) were determined using SimBiology and verified graphically. The area under the tissue concentration-time curve (AUC) from time zero to the last measured time (AUC0-last) was determined using the linear trapezoidal method. The area under the first moment concentration-time curve was calculated from time zero to the last measured time (AUMC0-last) using the linear trapezoidal method. Due to the lack of reliable terminal data points, namely in deep brain tissues, terminal slope analysis was not performed, and consequently AUC or AUMC analysis was not extended to time infinity. Mean residence time (MRT) was calculated as the ratio of AUMC and AUC (i.e., MRT=AUMC/AUC).

To perform quantification of BDNF protein levels in brain sub-regions, BDNF protein de-repression levels in each extracted protein sample were analyzed using BDNF sandwich ELISA kits according to the manufacturer's protocol. The calculated BDNF protein concentration values were normalized to the amount of total protein in each sample and expressed as pg of BDNF per μg of protein.

To perform the pharmacokinetic analysis of in vivo BDNF response, the tissue levels of BDNF in treated animals were baseline corrected using BDNF levels from naïve animals. NCA of the concentration-time curve of BDNF protein was performed using SimBiology/MATLAB. The maximal concentration ($C_{max}$) and time of maximal concentration ($t_{max}$) were determined with SimBiology and verified graphically. The area under the effect curve was determined via the linear trapezoidal method, and the analysis was restricted from time zero to the last measured time (AUEC0-last) due to inconsistent terminal data.

The performance of the implant formulation was evaluated in comparison to the previously reported AT-Gel depot formulation (Padmakumar, et al., 2021). As previously reported, kinetic parameters for the depot were determined from 0 to 96 hours and not extended to time infinity due to unreliable terminal data points. Subsequently, the kinetic parameters such as $C_{max}$ and AUC of MIND core-shell implants were compared relative to those for depot and the percent changes were determined.

Example 6. Analysis of Explanted Osmotic Implants for Residual BDNF AT

The implants were explanted from the olfactory submucosal space of animals upon euthanasia. The weights were recorded and compared to the weight of the exact implant measured prior to MIND administration. The implants were then cut open to retrieve the remaining gel which was subjected to nanodrop quantification of BDNF AT. These values subtracted from the initially loaded BDNF AT amount gave the amount of AT released from the implant at that time-point. The cumulative AT release was then calculated to plot the in vivo AT release profile over time. The surface features of explanted implants were qualitatively assessed by FESEM in order to study the morphological alterations over time.

To perform the histological analysis of explanted osmotic implants, the surgical sites of all animals subjected to MIND implantation were closely monitored throughout the study frame for any signs of infection, edema or inflammation. Examples are presented in FIG. 22. After sacrifice, the rat nasal cavities were opened and visually inspected for any signs of infection around the implant. Examples are shown in FIG. 23. Nasal tissues at the implant-nasal cavity interface were collected from the snouts of animals subjected to MIND implantation upon sacrifice at different time points. The tissue samples were fixed in 10% (v/v) neutral buffered formalin, embedded in paraffin wax and sectioned by microtome at a thickness of 5 μm for standard histology analysis. Staining was done with hematoxylin and eosin (H&E) and slides were imaged with a camera-equipped microscope (Keyence BZ-X710 All-in-One Fluorescence Microscope, Itasca, IL) for the qualitative analysis of the gross morphology of tissues at the interface of implant and nasal cavity.

REFERENCES

Güney A, Gardiner C, McCormack A, Malda J, Grijpma D W. Thermoplastic PCL-b-PEG-b-PCL and HDI Polyurethanes for Extrusion-Based 3D-Printing of Tough Hydrogels. *Bioengineering (Basel).* 2018 Nov. 14; 5(4):99. doi: 10.3390/bioengineering5040099. PMID: 30441879; PMCID: PMC6316089.

Shaukat, Ali, Karl Kolter, and Karl Matthias, Evaluation of Different Polymers in 3D Printing, BASF Corporation (2019).

Andreone, B. J., Larhammar, M. & Lewcock, J. W. Cell Death and Neurodegeneration. 19.

Farooqui, A. A. Chapter 1-Classification and Molecular Aspects of Neurotraumatic Diseases: Similarities and Differences With Neurodegenerative and Neuropsychiatric Diseases. in *Ischemic and Traumatic Brain and Spinal Cord Injuries; Farooqui, A A, Ed,* 1-40 (Academic Press., 2018).

Marilù Giacalone, Filippo Di Sacco, Ippolito Traupe, Nicola Pagnucci, Francesco Forfori, Francesco Giunta. Chapter 2—Blueberry Polyphenols and Neuroprotection. in *Bioactive Nutraceuticals and Dietary Supplements in Neurological and Brain Disease, Editor(s): Ronald Ross Watson, Victor R. Preedy* 17-28 (Academic Press, 2015).

Sheikh, S., Safia, Hague, E. & Mir, S. S. Neurodegenerative Diseases: Multifactorial Conformational Diseases and Their Therapeutic Interventions. *J Neurodegener. Dis.* 2013, 1-8 (2013).

Przedborski, S., Vila, M. & Jackson-Lewis, V. Neurodegeneration: What is it and where are we? *J. Clin. Invest.* 111, 8 (2003).

Duggan, M., Torkzaban, B., Ahooyi, T. M., Khalili, K. & Gordon, J. Age-related neurodegenerative diseases. *J. Cell. Physiol.* 235, 3131-3141 (2020).

Tanner, C. M. & Goldman, S. M. Epidemiology of Parkinson's disease. 20 (1996).

Huang, E. J. & Reichardt, L. F. Neurotrophins: Roles in Neuronal Development and Function. *Annu. Rev. Neurosci.* 24, 677-736 (2001).

Padmakumar, S., Taha, M. S., Kadakia, E., Bleier, B. S. & Amiji, M. M. Delivery of neurotrophic factors in the treatment of age-related chronic neurodegenerative diseases. *Expert Opin. Drug Deliv.* 17, 323-340 (2020).

Bathina, S. & Das, U. N. Brain-derived neurotrophic factor and its clinical implications. *Arch. Med. Sci.* 6, 1164-1178 (2015).

Miranda, M., Morici, J. F., Zanoni, M. B. & Bekinschtein, P. Brain-Derived Neurotrophic Factor: A Key Molecule for Memory in the Healthy and the Pathological Brain. *Front. Cell. Neurosci.* 13, 363 (2019).

Parain, K. et al. Reduced expression of brain-derived neurotrophic factor protein in Parkinson's disease substantia nigra. 5, 1999.

Palasz, E. et al. BDNF as a Promising Therapeutic Agent in Parkinson's Disease. *Int J Mol Sci* 23 (2020).

Mogi, M. et al. Brain-derived growth factor and nerve growth factor concentrations are decreased in the substantia nigra in Parkinson's disease. *Neurosci. Lett.* 4 (1999).

Murer, M. G., Yan, Q. & Raisman-Vozari, R. Brain-derived neurotrophic factor in the control human brain, and in Alzheimer's disease and Parkinson's disease. *Prog. Neurobiol.* 63, 71-124 (2001).

Zigova, T., Pencea, V., Wiegand, S. J. & Luskin, M. B. Intraventricular Administration of BDNF Increases the Number of Newly Generated Neurons in the Adult Olfactory Bulb. *Mol. Cell. Neurosci.* 11, 234-245 (1998).

Modarresi, F. et al. Inhibition of natural antisense transcripts in vivo results in gene-specific transcriptional upregulation. *Nat. Biotechnol.* 30, 453-459 (2012).

Kowiański, P. et al. BDNF: A Key Factor with Multipotent Impact on Brain Signaling and Synaptic Plasticity. *Cell. Mol. Neurobiol.* 38, 579-593 (2018).

Mitchelmore, C. & Gede, L. Brain derived neurotrophic factor: Epigenetic regulation in psychiatric disorders. *Brain Res.* 1586, 162-172 (2014).

Mercado, N., Collier, T., Sortwell, C. & Steece-Collier, K. BDNF in the Aged Brain: Translational Implications for Parkinson's Disease. 18 (2018).

Cattaneo, A., Cattane, N., Begni, V., Pariante, C. M. & Riva, M. A. The human BDNF gene: peripheral gene expression and protein levels as biomarkers for psychiatric disorders. *Transl. Psychiatry* 6, e958-e958 (2016).

Martínez-Levy, G. A. & Cruz-Fuentes, C. S. Genetic and Epigenetic Regulation of the Brain-Derived Neurotrophic Factor in the Central Nervous System. 2014.

Khorkova, O. & Wahlestedt, C. Oligonucleotide therapies for disorders of the nervous system. *Nat. Biotechnol.* 35, 249-263 (2017).

Smith, R. A. et al. Antisense oligonucleotide therapy for neurodegenerative disease. 8.

Cohen-Pfeffer, J. L. et al. Intracerebroventricular Delivery as a Safe, *Long-Term Route of Drug* Administration. *Pediatr. Neurol.* 67, 23-35 (2017).

Slavc, I. et al. Best practices for the use of intracerebroventricular drug delivery devices. *Mol. Genet. Metab.* 124, 184-188 (2018).

Hanson, L. R. & Frey, W. H. Intranasal delivery bypasses the blood-brain barrier to target therapeutic agents to the central nervous system and treat neurodegenerative disease. *BMC Neurosci.* 9, S5 (2008).

Padmakumar, S. et al. *Minimally Invasive Nasal Depot (MIND) technique for direct BDNF* AntagoNAT delivery to the brain. *J. Controlled Release* 331, 176-186 (2021).

DiResta, G. R. et al. Measurement of Brain Tissue Density Using Pycnometry. in *Brain Edema VIII* (eds. Reulen, H.-J., Baethmann, A., Fenstermacher, J., Marmarou, A. & Spatz, M.) 34-36 (Springer Vienna, 1990). doi:10.1007/978-3-7091-9115-6_12.

Noncompartmental Analysis—MATLAB & Simulink. (2017).

Lv, C. et al. Enhanced permeation performance of cellulose acetate ultrafiltration membrane by incorporation of Pluronic F127. *J. Membr. Sci.* 7 (2007).

Falath, W., Sabir, A. & Jacob, K. I. Highly improved reverse osmosis performance of novel PVA/DGEBA cross-linked membranes by incorporation of Pluronic F-127 and MWCNTs for water desalination. 14 (2016).

Tan, H. & Marra, K. G. Injectable, Biodegradable Hydrogels for Tissue Engineering Applications. *Materials* 3, 1746-1767 (2010).

Gioffredi, E. et al. *Pluronic F*127 Hydrogel Characterization and Biofabrication in Cellularized Constructs for Tissue Engineering Applications. *Procedia CIRP* 49, 125-132 (2016).

Gilbert, J. C., Hadgraft, J., Bye, A. & Brookes, L. G. Drug release from Pluronic F-127 gels. *Int. I Pharm.* 32, 223-228 (1986).

Guzmán, M., Garcia, F. F., Molpeceres, J. & Aberturas, M. R. Polyoxyethylene-polyoxypropylene block copolymer gels as sustained release vehicles for subcutaneous drug administration. *Int. J. Pharm.* 80, 119-127 (1992).

Iwasaki, Y. Platelet compatible blood filtration fabrics using a phosphorylcholine polymer having high surface mobility. *Biomaterials* 24, 3599-3604 (2003).

Ishihara, K., Hanyuda, H. & Nakabayashi, N. Synthesis of phospholipid polymers having a urethane bond in the side chain as coating material on segmented polyurethane and their platelet adhesion-resistant properties. 7, (1995).

Woodruff, M. A. & Hutmacher, D. W. The return of a forgotten polymer—Polycaprolactone in the 21st century. 40 (2010).

Manoukian, O. S. et al. Biodegradable Polymeric Injectable Implants for Long-Term Delivery of Contraceptive Drugs. 23 (2019).

Amjad, F. et al. Current Practices for Outpatient Initiation of Levodopa-Carbidopa Intestinal Gel for Management of Advanced Parkinson's Disease in the United States. *Adv. Ther.* 36, 2233-2246 (2019).

Harkema, J. R., Carey, S. A. & Wagner, J. G. The Nose Revisited: A Brief Review of the Comparative Structure, Function, and Toxicologic Pathology of the Nasal Epithelium. *Toxicol. Pathol.* 34, 252-269 (2006).

Gänger, S. & Schindowski, K. Tailoring Formulations for Intranasal Nose-to-Brain Delivery: A Review on Architecture, Physico-Chemical Characteristics and Mucociliary Clearance of the Nasal Olfactory Mucosa. *Pharmaceutics* 10, 116 (2018).

T. R. Shantha. CNS Delivery—Bypassing the BBB: Drug delivery from the olfactory mucosa to the CNS. *Drug Dev. Deliv.* 17, 32-37 (2017).

Silhol, M., Bonnichon, V., Rage, F. & Tapia-Arancibia, L. Age-related changes in brain-derived neurotrophic factor and tyrosine kinase receptor isoforms in the hippocampus and hypothalamus in male rats. *Neuroscience* 132, 613-624 (2005).

Katoh-Semba, R. & Takeuchi, I. K. Distribution of Brain—Derived Neurotrophic Factor in Rats and Its Changes with Development in the Brain. 9, (1997).

Coria-Lucero, C. D., et al., Rhythmic Bdnf and TrkB expression patterns in the prefrontal cortex are lost in aged rats. *Brain Res.* 8, (2016).

Conner, J. M., Lauterborn, J. C., Yan, Q., Gall, C. M. & Varon, S. Distribution of Brain-Derived Neurotrophic Factor (BDNF) Protein and mRNA in the Normal Adult Rat CNS: Evidence for Anterograde Axonal Transport. 19, (1997).

Castren, E., Thoenen, H., & Lindholm, D. Brain-derived neurotrophic factor messenger RNA is expressed in the septum, hypothalamus and in adrenergic brain stem nuclei of adult rat brain and is increased by osmotic stimulation in the paraventricular nucleus. *Neuroscience* 64, 71-80 (1995).

Guthrie, K. M. & Gall, C. M. Differential expression of mRNAs for the NGF family of neurotrophic factors in the adult rat central olfactory system. *J. Comp. Neurol.* 313, 95-102 (1991).

Ceccatelli, S., Ernfors, P., Villar, M. J., Persson, H. & Hokfelt, T. Expanded distribution of mRNA for nerve growth factor, brain-derived neurotrophic factor, and neurotrophin 3 in the rat brain after colchicine treatment. *Proc. Natl. Acad. Sci.* 88, 10352-10356 (1991).

Phillips, H., Hains, J., Laramee, G., Rosenthal, A. & Winslow, J. Widespread expression of BDNF but not NT3 by target areas of basal forebrain cholinergic neurons. *Science* 250, 290-294 (1990).

Mazur, C. et al. Brain pharmacology of intrathecal antisense oligonucleotides revealed through multimodal imaging. *JCI Insight* 4, e129240 (2019).

Visan, A. I. et al. Long-Term Evaluation of Dip-Coated PCL-Blend-PEG Coatings in Simulated Conditions. *Polymers* 12, 717 (2020).

Lyu, J. S., Lee, J.-S. & Han, J. Development of a biodegradable polycaprolactone film incorporated with an antimicrobial agent via an extrusion process, *Scientific Reports,* 11, (2019).

Nayyer, L., Jell, G., Esmaeili, A., Birchall, M. & Seifalian, A. M. A Biodesigned Nanocomposite Biomaterial for Auricular Cartilage Reconstruction. *Adv. Healthc. Mater.* 5, 1203-1212 (2016).

Atlan, Michael, Gina Nuti, Hongpeng Wang, Sherri Decker, and TracyAnn Perry. Breast implant surface texture impacts host tissue response. *Journal of the mechanical behavior of biomedical materials* 377-385 (2018).

What is claimed is:

1. An osmotic core-shell implant for trans-nasal delivery of one or more therapeutic agents, the implant comprising:
a shell comprising a first biodegradable polymer, the shell surrounding a reservoir; and
an osmotic core comprising an osmotic hydrogel containing a second biodegradable polymer and a therapeutic agent, the osmotic core disposed in the reservoir.

2. The implant of claim 1, wherein the first biodegradable polymer is a natural or synthetic polymer selected from the group consisting of gelatin, chitosan, cellulose or cellulose derivatives, poly(s-caprolactone) (PCL), polyethylene glycol (PEG), poly(lactic-co-glycolic acid) (PLGA), polylactic acid (PLA), polyglycolide, PEG-PLA diblock copolymer, PEG-PLGA diblock copolymer, PEG-PCL diblock copolymer, PCL-b-PEG-b-PCL co-polymer, and combinations thereof.

3. The implant of claim 1, wherein the second biodegradable polymer is a polyethylene oxide-polypropylene oxide-polyethylene oxide (PEO-PPO-PEO) triblock copolymer.

4. The implant of claim 3, wherein the PEO-PPO-PEO triblock copolymer is present at a concentration of 30 w/v %.

5. The implant of claim 1, wherein the shell comprises one or more openings or pores through which the osmotic core is exposed to a fluid outside the implant when the implant is placed in a subject.

6. The implant of claim 5, wherein the shell comprises pores and the pores have an average diameter in the range from about 0.1 µm to about 100 µm.

7. The implant of claim 1, wherein the first biodegradable polymer is hydrophobic.

8. The implant of claim 1, wherein the second biodegradable polymer is PEG having an average molecular weight (Mn) in the range from about 750 Da to about 14000 Da.

9. The implant of claim 1, wherein the therapeutic agent is a small molecule drug, a growth factor, a natural antisense transcript inhibitor, mRNA, a nutrient, a memory enhancing agent, a stimulant, an oligopeptide, a protein, an oligonucleotide, a tumor-targeting ligand, an antibody, an aptamer, a cell adhesion molecule, or a combination thereof.

10. The implant of claim 1 that is configured for implantation in a human subject within an olfactory sub-epithelium of the subject or within a submucosal space of an olfactory epithelium of the subject.

11. The implant of claim 1 that is capable of releasing the therapeutic agent into a central nervous system of a human subject.

12. The implant of claim 1, wherein the first biodegradable polymer biodegrades after an implantation into a nasal cavity of a subject for a duration in the range from about 1 day to about 365 days.

13. A method of sustained delivery of a therapeutic agent to a central nervous system (CNS) of a subject in need thereof, the method comprising:
(a) providing an osmotic core-shell implant comprising:
a shell comprising a first biodegradable polymer, the shell surrounding a reservoir; and
an osmotic core comprising an osmotic hydrogel containing a second biodegradable polymer and a therapeutic agent, the osmotic core disposed in the reservoir; and
(b) placing the implant into a submucosal space of an olfactory epithelium of the subject;
whereby the therapeutic agent is released from the implant and enters the CNS of the subject over a period of time.

14. The method of claim 13, wherein the osmotic hydrogel swells when the implant is implanted in the subject.

15. The method of claim 13, wherein step (b) comprises performing a surgical procedure on the subject.

16. The method of claim 13, wherein the method aids in treatment of a disease or disorder of the CNS of the subject.

17. A kit for delivering a therapeutic agent to the CNS of a subject, the kit comprising:
an osmotic core-shell implant comprising:
a shell comprising a first biodegradable polymer, the shell surrounding a reservoir; and
an osmotic core comprising an osmotic hydrogel containing a second biodegradable polymer and a therapeutic agent, the osmotic core disposed in the reservoir,
instructions for implanting the implant into a region of an olfactory epithelium of a subject, and
optionally one or more solutions, reagents, or devices for use during implantation of the implant.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: BDNF AT sequence

<400> SEQUENCE: 1
cataggagac cctccgcaac                                               20

<210> SEQ ID NO 2
<211> LENGTH: 11
<212> TYPE: DNA
<213> ORGANISM: Artificial Sequence
<220> FEATURE:
<223> OTHER INFORMATION: Detection probe

<400> SEQUENCE: 2
ggtctcctat g                                                        11